（12) United States Patent
Takhi et al.

(10) Patent No.: US 9,062,075 B2
(45) Date of Patent: Jun. 23, 2015

(54) TETRAHYDROPYRIDINE DERIVATIVES AS FABI INHIBITORS

(71) Applicants: Aurigene Discovery Technologies Limited, Bangalore (IN); UM Pharmauji Sdn. BHD, Kuala Lumpur (MY)

(72) Inventors: Mohamed Takhi, Hyderabad (IN); Subramanya Hosahalli, Bangalore (IN); Sunil Kumar Panigrahi, Kantamal (IN)

(73) Assignees: Aurigene Discovery Technologies Limited, Bangalore (IN); UM Pharmauji Sdn. BHD, Kuala Lumpur (MY)

( * ) Notice: Subject to any disclaimer, the term of this patent is extended or adjusted under 35 U.S.C. 154(b) by 0 days.

(21) Appl. No.: 14/294,576

(22) Filed: Jun. 3, 2014

(65) Prior Publication Data

US 2014/0275019 A1    Sep. 18, 2014

Related U.S. Application Data

(63) Continuation-in-part of application No. 14/361,171, filed as application No. PCT/IN2012/000776 on Nov. 29, 2012.

(30) Foreign Application Priority Data

Dec. 2, 2011 (IN) ............................ 4176/CHE/2011
Jun. 4, 2013 (IN) ............................ 2444/CHE/2013

(51) Int. Cl.
| | |
|---|---|
| C07D 471/04 | (2006.01) |
| C07D 491/20 | (2006.01) |
| C07D 471/20 | (2006.01) |
| A61K 31/4375 | (2006.01) |
| A61K 31/5377 | (2006.01) |
| A61K 31/55 | (2006.01) |
| A61K 31/551 | (2006.01) |
| A61K 45/06 | (2006.01) |

(52) U.S. Cl.
CPC ............ *C07D 491/20* (2013.01); *C07D 471/20* (2013.01); *A61K 31/4375* (2013.01); *C07D 471/04* (2013.01); *A61K 31/5377* (2013.01); *A61K 31/55* (2013.01); *A61K 31/551* (2013.01); *A61K 45/06* (2013.01)

(58) Field of Classification Search
CPC .. C07D 471/04; C07D 491/20; C07D 471/20; A61K 31/4375; A61K 31/5377
USPC ................... 514/210.18, 212.02, 278, 232.8, 514/212.06, 221, 220, 300; 546/18, 122; 540/524, 521, 501, 496; 544/70
See application file for complete search history.

(56) References Cited

U.S. PATENT DOCUMENTS

| | | | |
|---|---|---|---|
| 5,506,261 A * | 4/1996 | Brooks et al. ................. | 514/438 |
| 6,326,381 B1 | 12/2001 | Kelly et al. | |
| 6,503,903 B1 | 1/2003 | Miller et al. | |
| 6,730,684 B1 | 5/2004 | Miller et al. | |
| 6,762,201 B1 | 7/2004 | Miller et al. | |
| 6,765,005 B2 | 7/2004 | Miller et al. | |
| 6,846,819 B1 | 1/2005 | Miller et al. | |
| 7,049,310 B2 | 5/2006 | Burgess et al. | |
| 7,250,424 B2 | 7/2007 | Burgess et al. | |
| 7,524,843 B2 | 4/2009 | Miller et al. | |
| 7,557,125 B2 | 7/2009 | Miller et al. | |
| 7,741,339 B2 | 6/2010 | Burgess et al. | |
| 7,790,716 B2 | 9/2010 | Miller et al. | |

FOREIGN PATENT DOCUMENTS

| | | |
|---|---|---|
| WO | 2011061214 | 5/2011 |
| WO | 2013021051 | 2/2013 |
| WO | 2013021052 | 2/2013 |

OTHER PUBLICATIONS

Bergler et al. "Protein EnvM Is the NADH-dependent Enoyl-ACP Reductase (FabI) of *Escherichia coli*", Journal of Biological Chemistry, vol. 269, No. 8, pp. 5493-5496, Feb. 25, 1994.
Heath et al. "Regulation of Fatty Acid Elongation and Initiation by Acyl-Acyl Carrier Protein in *Escherichia coli*", Journal of Biological Chemistry, vol. 271, No. 4, pp. 1833-1836, Jan. 26, 1996.
Grassberger et al. "Preparation and Antibacterial Activities of New 1,2,3-Diazaborine Derivatives and Analogues", Journal of Medicinal Chemistry, vol. 27, pp. 947-953, Aug. 1984.
McMurry et al. "Triclosan targets lipid synthesis", Nature, vol. 394, pp. 531-532, Aug. 6, 1998.
International Search Report for priority PCT Application No. PCT/IN2012/000776, mailed Apr. 25, 2013 (3 pages).
Miller, W.H. "Discovery of aminopyridine-based inhibitors of bacterial enoyl-ACP reductase (FabI)", Journal of Medicinal Chemistry, vol. 45, No. 15, pp. 3246-3256, Jun. 19, 2002.

* cited by examiner

*Primary Examiner* — Niloofar Rahmani
(74) *Attorney, Agent, or Firm* — Winthrop & Weinstine, P.A.

(57) ABSTRACT

The present invention relates to tetrahydropyridine derivatives of formula (1) which may be therapeutically useful as anti-bacterial agents, more particularly FabI inhibitors.

(1)

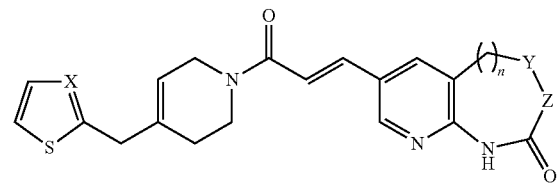

in which X, Y, Z and "n" have the same meanings given in the specification, and pharmaceutically acceptable salts and pharmaceutically acceptable stereoisomers thereof that are useful in the treatment and prevention in diseases or disorder, in particular their use in diseases or disorder where there is an advantage in inhibiting Enoyl-ACP reductase enzyme (FabI) activity.
The present invention also provides methods for synthesizing and administering the FabI inhibitory compounds. The present invention also provides pharmaceutical formulations comprising at least one of the FabI inhibitory compounds together with a pharmaceutically acceptable carrier, diluent or excipient therefor.

19 Claims, No Drawings

TETRAHYDROPYRIDINE DERIVATIVES AS FABI INHIBITORS

FIELD OF INVENTION

The present invention relates to tetrahydropyridine derivatives of formula (I) which are useful as anti-bacterial agents. The present invention also relates to the preparation of compounds of formula (I) and their use for the treatment and prevention in diseases or disorder, in particular their use in diseases or disorder associated where there is an advantage in inhibiting Enoyl-ACP reductase enzyme (FabI) activity.

BACKGROUND AND PRIOR ART

Fatty acid biosynthesis (or FAB) is an important metabolic process for all living organisms and is used to produce the metabolic precursors for membrane phospholipids in the cell wall. Fatty acids are produced by mammals (using enzyme FAS I) and bacteria (using enzyme FAS II) via substantially different biosynthetic mechanisms, thus improving the possibility of bacteria-specific drug targeting. Indeed, inhibitors that are targeting the several stages of the fatty acid biosynthetic pathway have been investigated as anti-bacterial agents. Broadly, the biological pathway of saturated fatty acid biosynthesis (FAB) is more or less similar in all organisms, however, the enzymatic biosynthesis systems of fatty acid synthase (FAS) vary considerably with respect to their structural organization. Mammalian fatty acid synthesis (FAS-I) employs a multifunctional enzyme complex in which all enzymatic activities reside on a single polypeptide. In contrast, bacterial fatty acid synthesis (FAS-II) elongation cycle utilizes various distinct monofunctional enzymes with activity related to respective enzyme peptides effecting fatty acid chain elongation and ultimately cell membrane production. Enoyl acyl carrier protein reductase (FabI) is the component of FAS-II which catalyzes the final reaction in the enzymatic sequence. Therefore, there is a considerable scope for the selective inhibition of the bacterial FAS system enzymes by exploring newer anti-bacterial agents.

FabI (a protein enzyme encoded by EnVM gene) acts as an enoyl-ACP reductase (Bergler, et al, *J. Biol. Chem.* 269, 1994, 5493-5496) in the final step of the reactions which are involved in each cycle of bacterial fatty acid biosynthesis. Further rounds of this cycle, adding two carbon atoms per cycle, eventually lead to palmitoyl-ACP (16-Carbon), and subsequently the feedback inhibition of FabI by palmitoyl-ACP largely blocks the cycle (Heath et al, *J. Biol. Chem.* 271, 1996, 1833-1836).

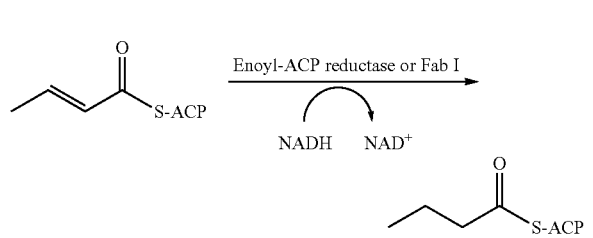

Thus, FabI is one among the major biosynthetic enzyme and appears to be a key moderator in the overall bacterial fatty acid biosynthetic pathway. Therefore, FabI may be one of the meaningful target for acquiring anti-bacterial role.

Though there is plethora of literature on FabI, which provides different inhibitors, however, among promising literature, it reveals that diazaborine (an antibiotics) inhibit fatty acid, phospholipid and lipopolysaccharide (LPS) biosynthesis via Fab I as one of the anti-bacterial target. Grassberger et al, in *J. Med. Chem.* 27, 1984, 947-953 reported derivative of 2b18 (a peptide) possessing non-competitive inhibitory activity of FabI (Bergler et al, *J. Biol. Chem.* 269, 1994, 5493-5496). Bergler et al, in *J. Biol. Chem.* 269, 1994, 5493-5496 reported that inhibition of FabI either by diazaborine or by raising the temperature in a FabI temperature sensitive mutant is lethal. These results demonstrate that FabI appears to be essential for the survival of the organism. McMurry et al, in *Nature* 394, 1998, 531-532 have shown that FabI is also the target for the well known broad spectrum anti-bacterial agent triclosan. Miller W H et al, in *J Med Chem.*; 45(15), 2002, 3246-56 disclosed aminopyridine-based inhibitors of bacterial enoyl-ACP reductase (FabI). Recent literature including U.S. Pat. No. 7,790,716; U.S. Pat. No. 7,741,339; U.S. Pat. No. 7,557,125; U.S. Pat. No. 7,524,843; U.S. Pat. No. 7,250,424; U.S. Pat. No. 7,049,310; U.S. Pat. No. 6,846,819; U.S. Pat. No. 6,765,005; U.S. Pat. No. 6,762,201; U.S. Pat. No. 6,730,684 and U.S. Pat. No. 6,503,903 also reveals that diverse compounds are known to possess FabI inhibitory activity and have anti-bacterial role, and, therefore, may be useful for the treatment of bacterial infections in mammals, particularly in man.

International patent application WO2013/021051 disclosed piperidinyl substituted 3,4-dihydro-1H-[1,8]-naphthyridinone derivatives as FabI inhibitors.

Further antimicrobial resistances among clinical isolates have been observed as one of the major problem in recent years. Of particular concern has been the increasing incidence of methicillin-resistant *Staphylococcus* spp., vancomycin-resistant *Enterococcus* spp., and penicillin-resistant *Streptococcus pneumoniae*.

With the rise in number of patients affected by diverse bacterial and related microbial diseases and drug resistance, there appears to be unmet need for newer drugs that can treat such diseases more effectively. There is still need for newer anti-bacterial agents, which may be further useful in a wide variety of bacterial infections and possessing broader spectrum.

SUMMARY OF INVENTION

The present invention relates to tetrahydropyridine derivatives of formula (I) useful as anti-bacterial agents.

In one aspect of the present invention, it relates to compound of formula (I):

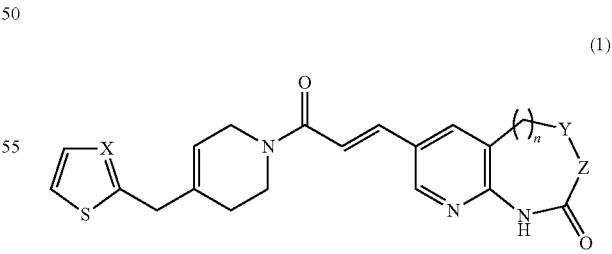

or a pharmaceutically acceptable salt or a pharmaceutically acceptable stereoisomer thereof,
wherein,
X represents N or CH;
Y represents $NR_1$ or $CHR_1$;
Z represents $CR_2R_3$;
$R_1$ represents hydrogen or alkyl;

$R_2$ and $R_3$ are independently selected from hydrogen and alkyl;

alternatively, $R_2$ and $R_3$ may be taken together with the carbon atoms to which they are attached to form an optionally substituted 3-7 membered ring containing 0-3 hetero atoms or groups; wherein the optional substituent is $R_4$ and the heteroatoms are independently selected from N, O, NH and CO in any stable combination;

alternatively, $R_1$ and $R_2$ may be taken together with the carbon or nitrogen atom to which they are attached to form 5-membered fused ring;

$R_4$ at each occurrence is selected from alkyl, —COOR$_5$, —COR$_5$, —CONR$_5$R$_5$, —SO$_2$R$_5$, —COCH$_2$OR$_5$, —CO(CH$_2$)$_2$COOR$_5$, —COCH$_2$NR$_5$R$_5$ and cycloalkyl;

$R_5$ at each occurrence is selected from hydrogen, alkyl, cycloalkyl and heterocyclyl; and 'n' is selected from an integer 0 or 1.

In a further aspect of the present invention, it relates to the pharmaceutical composition comprising tetrahydropyridine derivatives of formula (I) and processes for preparing thereof.

In yet further another aspect of the present invention, it relates to the use of novel tetrahydropyridine derivatives of formula (I) and their pharmaceutically acceptable salts and pharmaceutically acceptable stereoisomers thereof, including mixtures thereof in all suitable ratios wherever applicable as a medicament for the treatment and prevention of disorder or diseases by inhibitory action on enzymes—FabI or FabK or both.

DETAILED DESCRIPTION OF THE INVENTION

Embodiments of the present application provides novel tetrahydropyridine derivatives of formula (I) useful as antibacterial agents.

One of the embodiment of the present invention provides compound of formula (I):

(1)

or a pharmaceutically acceptable salt or a pharmaceutically acceptable stereoisomer thereof,
wherein,
X represents N or CH;
Y represents NR$_1$ or CHR$_1$,
Z represents CR$_2$R$_3$;
R$_1$ represents hydrogen or alkyl;
R$_2$ and R$_3$ are independently selected from hydrogen and alkyl;

alternatively, R$_2$ and R$_3$ may be taken together with the carbon atoms to which they are attached to form an optionally substituted 3-7 membered ring containing 0-3 hetero atoms or groups; wherein the optional substituent is R$_4$ and the heteroatoms are independently selected from N, O, NH and CO in any stable combination;

alternatively, R$_1$ and R$_2$ may be taken together with the carbon or nitrogen atom to which they are attached to form 5-membered fused ring;

R$_4$ at each occurrence is selected from alkyl, —COOR$_5$, —COR$_5$, —CONR$_5$R$_5$, —SO$_2$R$_5$, —COCH$_2$OR$_5$, —CO(CH$_2$)$_2$COOR$_5$, —COCH$_2$NR$_5$R$_5$ and cycloalkyl;

R$_5$ at each occurrence is selected from hydrogen, alkyl, cycloalkyl and heterocyclyl; and 'n' is selected from an integer 0 or 1.

The embodiments below are illustrative of the present invention and are not intended to limit the claims to the specific embodiments exemplified.

According to one particular embodiment of formula (1), the present invention comprises particular series of compound of formula (1a)

(1a)

or a pharmaceutically acceptable salt or a pharmaceutically acceptable stereoisomer thereof,
wherein;
X represents N or CH;
R$_2$ and R$_3$ are alkyl;
alternatively, R$_2$ and R$_3$ can be taken together with the carbon atom to which they are attached to form an 3-6 membered cycloalkyl ring;

According to one embodiment, specifically provided are compounds of formula (1a); wherein alkyl is methyl and ethyl.

According to another embodiment, specifically provided are compounds of formula (1a); wherein cycloalkyl ring is cyclopropyl, cyclobutyl and cyclohexyl.

According to yet another embodiment, compound of formula (1a) is a compound of formula (1b)

(1b)

wherein,
R$_2$ and R$_3$ are alkyl.

According to another particular embodiment of formula (1), specifically provided are compounds of formula (1c)

(1c)

wherein, W represents CH$_2$ or C(O);
X and R$_4$ are same as defined in formula (1).

According to one embodiment, specifically provided are compounds of formula (1c), wherein R$_4$ is selected from alkyl, —COOR₅, —COR₅, —CONR₅R₅, —SO₂R₅, —COCH₂OR₅, —CO(CH₂)₂COOR₅, —COCH₂NR₅R₅ and cycloalkyl; particular alkyl is methyl and cycloalkyl is cyclopropyl.

According to another embodiment, specifically provided are compounds of formula (1c), wherein R₅ at each occurrence is independently selected from hydrogen, alkyl, cycloalkyl and heterocyclyl; in particular alkyl is methyl and tert-butyl, cycloalkyl is cyclopropyl and cyclopentyl, and heterocyclyl is azetidine, furan and morpholine.

According to yet another particular embodiment of formula (1), specifically provided are compounds of formula (1d)

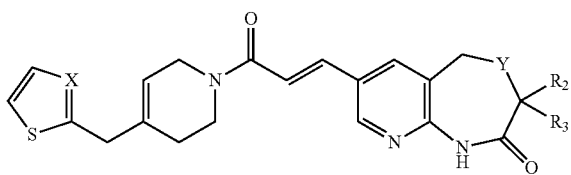

(1d)

wherein, X, Y, R₂ and R₃ are same as defined in formula (1).

According to one embodiment, specifically provided are compounds of formula (1d), wherein Y is NR₁; in particular R₁ is hydrogen.

According to another embodiment, specifically provided are compound of formula (1d), wherein R₂ and R₃ are alkyl.

According to yet another embodiment, specifically provided are compound of formula (1d), wherein R₁ and R₂ are taken together with the nitrogen and carbon atom to which they are attached to form a 5-membered fused ring.

According to one particular embodiment, specifically provided are compounds of formula (1) are selected from the group consisting of (E)-tert-butyl 2-oxo-6-(3-oxo-3-(4-(thiazol-2-ylmethyl)-5,6-dihydropyridin-1 (2H)-yl)prop-1-en-1-yl)-2,4-dihydro-1H-spiro[[1,8]naphthyridine-3,4'-piperidine]-1'-carboxylate (Compound 1);

(E)-6'-(3-oxo-3-(4-(thiazol-2-ylmethyl)-5,6-dihydropyridin-1 (2H)-yl)prop-1-en-1-yl)-1'H-spiro[cyclopropane-1,3'-[1,8]naphthyridin]-2'(4'H)-one (Compound 2);

(E)-6'-(3-oxo-3-(4-(thiazol-2-ylmethyl)-5,6-dihydropyridin-1 (2H)-yl)prop-1-en-1-yl)-1'H-spiro[cyclobutane-1,3'-[1,8]naphthyridin]-2'(4'H)-one (Compound 3);

(E)-6'-(3-oxo-3-(4-(thiazol-2-ylmethyl)-5,6-dihydropyridin-1 (2H)-yl)prop-1-en-1-yl)-1'H-spiro[cyclohexane-1,3'-[1,8]naphthyridin]-2'(4'H)-one (Compound 4);

(E)-6'-(3-oxo-3-(4-(thiophen-2-ylmethyl)-5,6-dihydropyridin-1 (2H)-yl)prop-1-en-1-yl)-1'H-spiro[cyclohexane-1,3'-[1,8]naphthyridin]-2'(4'H)-one (Compound 5);

(E)-6-(3-oxo-3-(4-(thiazol-2-ylmethyl)-5,6-dihydropyridin-1(2H)-yl)prop-1-en-1-yl)-2',3',5',6'-tetrahydro-1H-spiro[[1,8]naphthyridine-3,4'-pyran]-2(4H)-one (Compound 6);

(E)-6-(3-oxo-3-(4-(thiophen-2-ylmethyl)-5,6-dihydropyridin-1(2H)-yl)prop-1-en-1-yl)-2',3',5',6'-tetrahydro-1H-spiro[[1,8]naphthyridine-3,4'-pyran]-2(4H)-one (Compound 7);

(E)-6-(3-oxo-3-(4-(thiazol-2-ylmethyl)-5,6-dihydropyridin-1(2H)-yl)prop-1-en-1-yl)-1'-pivaloyl-1H-spiro[[1,8]naphthyridine-3,4'-piperidin]-2(4H)-one (Compound 8);

(E)-6-(3-oxo-3-(4-(thiophen-2-ylmethyl)-5,6-dihydropyridin-1(2H)-yl)prop-1-en-1-yl)-1'-pivaloyl-1H-spiro[[1,8]naphthyridine-3,4'-piperidin]-2(4H)-one (Compound 9);

(E)-1'-(cyclopropanecarbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 10);

(E)-1'-(cyclopropanecarbonyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one (Compound 11);

(E)-N-(tert-butyl)-2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide (Compound 12);

(E)-N-(tert-butyl)-2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide (Compound 13);

(E)-1'-(azetidine-1-carbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 14);

(E)-1'-(azetidine-1-carbonyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one (Compound 15);

(E)-1'-(morpholine-4-carbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 16);

(E)-1'-(methylsulfonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 17);

(E)-tert-butyl 4-oxo-4-(2-oxo-6-(3-oxo-3-(4-(thiazol-2-ylmethyl)-5,6-dihydro pyridin-1(2H)-yl)prop-1-en-1-yl)-2,4-dihydro-1H-spiro[[1,8]naphthyridine-3,4'-piperidin]-1'-yl)butanoate (Compound 18);

(E)-6'-(3-oxo-3-(4-(thiazol-2-ylmethyl)-5,6-dihydropyridin-1(2H)-yl)prop-1-en-1-yl)-1'H-spiro[azepane-4,3'-[1,8]naphthyridine]-2',7(4'H)-dione (Compound 19);

(E)-6'-(3-oxo-3-(4-(thiophen-2-ylmethyl)-5,6-dihydropyridin-1(2H)-yl)prop-1-en-1-yl)-1'H-spiro[azepane-4,3'-[1,8]naphthyridine]-2',7(4'H)-dione (Compound 20);

(E)-3-(3-oxo-3-(4-(thiazol-2-ylmethyl)-5,6-dihydropyridin-1(2H)-yl)prop-1-en-1-yl)-6,7-dihydro-5H-pyrido[2,3-b]azepin-8(9H)-one (Compound 21);

(E)-3-(3-oxo-3-(4-(thiophen-2-ylmethyl)-5,6-dihydropyridin-1(2H)-yl)prop-1-en-1-yl)-6,7-dihydro-5H-pyrido[2,3-b]azepin-8(9H)-one (Compound 22);

(E)-7'-(3-oxo-3-(4-(thiazol-2-ylmethyl)-5,6-dihydropyridin-1(2H)-yl)prop-1-en-1-yl)-4',5'-dihydrospiro[cyclopropane-1,3'-pyrido[2,3-e][1,4]diazepin]-2'(1'H)-one (Compound 23);

(E)-7'-(3-oxo-3-(4-(thiophen-2-ylmethyl)-5,6-dihydropyridin-1(2H)-yl)prop-1-en-1-yl)-4',5'-dihydrospiro[cyclopropane-1,3'-pyrido[2,3-e][1,4]diazepin]-2'(1'H)-one (Compound 24);

(E)-3,3-dimethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one (Compound 25);

(E)-3,3-dimethyl-6-(3-oxo-3-(4-(thiophen-2-ylmethyl)-5,6-dihydropyridin-1(2H)-yl)prop-1-en-1-yl)-3,4-dihydro-1,8-naphthyridin-2(1H)-one (Compound 26);

(E)-3,3-diethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one (Compound 27);
(E)-6'-(3-oxo-3-(4-(thiophen-2-ylmethyl)-5,6-dihydropyridin-1(2H)-yl)prop-1-en-1-yl)-1'H-spiro[cyclopropane-1,3'-[1,8]naphthyridin]-2'(4'H)-one (Compound 28);
(E)-6'-(3-oxo-3-(4-(thiophen-2-ylmethyl)-5,6-dihydropyridin-1(2H)-yl)prop-1-en-1-yl)-1'H-spiro[cyclobutane-1,3'-[1,8]naphthyridin]-2'(4'H)-one (Compound 29);
(E)-1-methyl-6'-(3-oxo-3-(4-(thiazol-2-ylmethyl)-5,6-dihydropyridin-1(2H)-yl)prop-1-en-1-yl)-1'H-spiro[azepane-4,3'-[1,8]naphthyridine]-2',7(4'H)-dione (Compound 30);
(E)-1'-(cyclopentanecarbonyl)-6-(3-oxo-3-(4-(thiazol-2-ylmethyl)-5,6-dihydro pyridin-1(2H)-yl)prop-1-en-1-yl)-1H-spiro[[1,8]naphthyridine-3,4'-piperidin]-2(4H)-one (Compound 31);
(S,E)-3-(3-oxo-3-(4-(thiazol-2-ylmethyl)-5,6-dihydropyridin-1(2H)-yl)prop-1-en-1-yl)-7,8,9,9a-tetrahydro-5H-pyrido[2,3-e]pyrrolo[1,2-a][1,4]diazepin-10(11H)-one (Compound 32);
(S,E)-3-(3-oxo-3-(4-(thiophen-2-ylmethyl)-5,6-dihydropyridin-1(2H)-yl)prop-1-en-1-yl)-7,8,9,9a-tetrahydro-5H-pyrido[2,3-e]pyrrolo[1,2-a][1,4]diazepin-10(11H)-one (Compound 33);
(E)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one 2,2,2-trifluoroacetate (Compound 34);
(E)-1'-methyl-6-(3-oxo-3-(4-(thiazol-2-ylmethyl)-5,6-dihydropyridin-1(2H)-yl) prop-1-en-1-yl)-1H-spiro[[1,8]naphthyridine-3,4'-piperidin]-2(4H)-one (Compound 35);
(E)-1'-cyclopropyl-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 36);
(E)-1'-(2-hydroxyacetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 37);
(E)-1'-(furan-2-carbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 38);
(E)-2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide (Compound 39);
(E)-4-oxo-4-(2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidin]-1'-yl)butanoic acid (Compound 40);
(E)-1'-(2-aminoacetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one hydrochloride (Compound 41);
(E)-1'-(2-(tert-butylamino)acetyl)-6-(3-oxo-3-(4-(thiazol-2-ylmethyl)-5,6-dihydro pyridin-1(2H)-yl)prop-1-en-1-yl)-1H-spiro[[1,8]naphthyridine-3,4'-piperidin]-2(4H)-one 2,2,2-trifluoroacetate (Compound 42); and
(E)-1-(2-hydroxyacetyl)-6'-(3-oxo-3-(4-(thiazol-2-ylmethyl)-5,6-dihydropyridin-1(2H)-yl)prop-1-en-1-yl)-1'H-spiro[azetidine-3,3'-[1,8]naphthyridin]-2'(4'H)-one (Compound 43),
or a pharmaceutically acceptable salt or a pharmaceutically acceptable stereoisomer thereof.

According to another particular embodiment, specifically provided are compounds of formula (1) are selected from the group consisting of (E)-6'-(3-oxo-3-(4-(thiazol-2-ylmethyl)-5,6-dihydropyridin-1(2H)-yl)prop-1-en-1-yl)-1'H-spiro[cyclopropane-1,3'-[1,8]naphthyridin]-2'(4'H)-one;
(E)-6'-(3-oxo-3-(4-(thiazol-2-ylmethyl)-5,6-dihydropyridin-1(2H)-yl)prop-1-en-1-yl)-1'H-spiro[cyclobutane-1,3'-[1,8]naphthyridin]-2'(4'H)-one;
(E)-6'-(3-oxo-3-(4-(thiazol-2-ylmethyl)-5,6-dihydropyridin-1(2H)-yl)prop-1-en-1-yl)-1'H-spiro[cyclohexane-1,3'-[1,8]naphthyridin]-2'(4'H)-one;
(E)-6'-(3-oxo-3-(4-(thiophen-2-ylmethyl)-5,6-dihydropyridin-1(2H)-yl)prop-1-en-1-yl)-1'H-spiro[cyclohexane-1,3'-[1,8]naphthyridin]-2'(4'H)-one;
(E)-3,3-dimethyl-6-(3-oxo-3-(4-(thiazol-2-ylmethyl)-5,6-dihydropyridin-1(2H)-yl) prop-1-en-1-yl)-3,4-dihydro-1,8-naphthyridin-2(1H)-one;
(E)-3,3-dimethyl-6-(3-oxo-3-(4-(thiophen-2-ylmethyl)-5,6-dihydropyridin-1(2H)-yl)prop-1-en-1-yl)-3,4-dihydro-1,8-naphthyridin-2(1H)-one;
(E)-3,3-diethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one;
(E)-6'-(3-oxo-3-(4-(thiophen-2-ylmethyl)-5,6-dihydropyridin-1(2H)-yl)prop-1-en-1-yl)-1'H-spiro[cyclopropane-1,3'-[1,8]naphthyridin]-2'(4'H)-one; and
(E)-6'-(3-oxo-3-(4-(thiophen-2-ylmethyl)-5,6-dihydropyridin-1(2H)-yl)prop-1-en-1-yl)-1'H-spiro[cyclobutane-1,3'-[1,8]naphthyridin]-2'(4'H)-one,
or a pharmaceutically acceptable salt or a pharmaceutically acceptable stereoisomer thereof.

In another particular embodiment, the definition of "compounds of formula (1)" inherently includes all stereoisomers of the compound of formula (1) either as pure stereoisomer or as a mixture of two or more steremers. The word stereoisomers includes enantiomers, diasteroisomers, racemates, cis isomers, trans isomers and mixture thereof.

The absolute configuration at an asymmetric atom is specified by either R or S. Resolved compounds whose absolute configuration is not known can be designated by (+) or (−) depending on the direction in which they rotate plane polarized light. When a specific stereisomer is identified, this means that said stereoisomer is substantially free, i.e. associated with less than 50%, preferably less than 20%, more preferably less than 5%, in particularly less than 2% or 1% of the other isomers. Thus when a compound of formula (1) is for instance specified as (R), this means that the compound is substantially free of (S) isomer; when the compound of formula (1) is for instance specified as E, this means that the compound is free of the Z isomer; when the compound of formula (1) is for instance specified as cis isomer, this means that the compound is free of the trans isomer.

In further yet another particular embodiment relates to the pharmaceutical composition comprising a therapeutically effective amount of a compound according to formula (1), their pharmaceutically acceptable salts and pharmaceutically acceptable stereoisomers thereof, in admixture with at least one pharmaceutically acceptable carriers, diluents or excipients, including mixtures thereof in all ratios, for use as a medicament.

In further yet another particular embodiment relates to the use of compounds of formula (1) and its pharmaceutically acceptable salts and stereoisomers thereof, including mixtures thereof in all ratios, for the preparation of a medicament for the treatment and prevention in diseases or disorder, where there is an advantage in inhibiting enzymes—FabI.

In further yet another particular embodiment relates to the use of compounds of formula (1) and its pharmaceutically acceptable salts and stereoisomers thereof, including mixtures thereof in all ratios, in the manufacture of a medicament for the treatment and prevention of bacterial infections, where there is an advantage in inhibiting enzymes—Fab I.

Use of compounds as above wherein there is an advantage in inhibiting enzymes—Fab I for anti bacterial or antimicrobial diseases.

Use of the compounds as above for the preparation of a medicament for the treatment and prophylaxis of cancer diseases, inflammatory bowel disease or rheumatoid arthritis.

In further yet another particular embodiment relates to the method of treating diseases or conditions for which FabI is indicated in a subject in need thereof which comprises administering a therapeutically effective amount of a compound of formula (1), their pharmaceutically acceptable salts and pharmaceutically acceptable stereoisomers thereof.

In further yet another particular embodiment relates to the method of treating bacterial infections in a subject in need thereof which comprises administering a therapeutically effective amount of a compound of formula (1), their pharmaceutically acceptable salts and pharmaceutically acceptable stereoisomers thereof.

In further yet another particular embodiment relates to the compound of formula (1), pharmaceutically acceptable salts and pharmaceutically acceptable stereoisomers thereof, for use in treatment of diseases or conditions for which FabI inhibitor is indicated.

In further yet another particular embodiment relates to the compound of formula (1), pharmaceutically acceptable salts and pharmaceutically acceptable stereoisomers thereof, for use in treatment of bacterial infection. In another particular embodiment, the invention further provides the use of tetrahydropyridine derivatives of formula (1) in combination with another active ingredient.

In another particular embodiment, the invention further provides the use of tetrahydropyridine derivatives of formula (1) in combination with anti-bacterial agents such as cephalosporins, quinolones and fluoroquinolones, penicillins, penicillins and beta lactamase inhibitors, carbapenems, monobactams, macrolides, lincosamines, glycopeptides, rifampin, oxazolidinones, tetracyclines, aminoglycosides, streptogramins, sulfonamides, and the like. Other general categories of antibiotic agents which may be part of a subject composition include those agents known to those of skill in the art as antibiotics and that qualify as (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. [section]355(a) ("regulatory approved drug"); any agent that is or was subject to a human drug application under 21 U.S.C. [section]379(g) ("human drug"). (All references to statutory code for this definition refer to such code as of the original filing date of this provisional application.) Other antibiotic agents are disclosed herein, and are known to those of skilled in the art. In certain embodiments, the term "antibiotic agent" does not include an agent that is a FabI inhibitor, so that the combinations of the present invention in certain instances will include one agent that is a FabI inhibitor and another agent that is not other anti-bacterial compounds. A preferred composition is comprising a compound of formula (1) and cyclosporin A, FK506, rapamycin, 40-(2-hydroxy)ethyl-rapamycin. Another preferred composition may comprise a compound of formula (1) and a rheumatoid arthritis active agent selected from leflunomide, etanercept (Enbrel), infliximab (Remicade), anakinra (Kineret), adalimumab (Humira), rituximab (Rituxan), and abatacept (Orencia).

In another particular embodiment, the invention further provides the process for the preparation of compound of formula 1 or a pharmaceutically acceptable salt or a pharmaceutically acceptable stereoisomer thereof, which comprises: reacting intermediate compound of formula 1.10

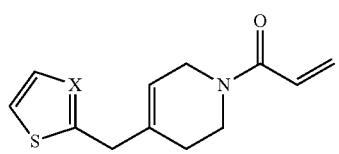

Formula 1.10 wherein, X is CH or N; with intermediate compound of formula 1.11

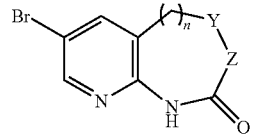

Formula 1.11 wherein, Y, Z and n are same as defined earlier;
by Heck reaction in a solvent in the presence of a palladium catalyst, ligand and a base to give compound of formula 1.

In another particular embodiment, the invention further provides process for the preparation of compound of formula 1 or a pharmaceutically acceptable salt or a pharmaceutically acceptable stereoisomer thereof, which comprises:
reacting intermediate compound of formula 1.9

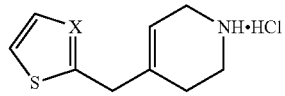

Formula 1.9 wherein, X is CH or N; with intermediate compound of formula 1.12

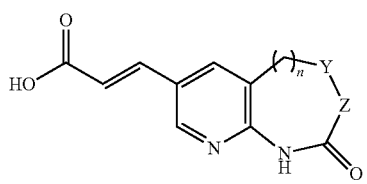

Formula 1.12 wherein, Y, Z and n are same as defined earlier;
by acid amine coupling in a solvent in the presence of a coupling reagent and a base to give compound of formula 1.

Without limiting the scope of present invention, the following definitions are provided in order to aid those skilled in the art in understanding the detailed description of the present invention.

The term "Alkyl" refers to a hydrocarbon chain that may be a straight chain or branched chain, containing the indicated number of carbon atoms; in particular alkyl is $C_1$-$C_{10}$ alkyl group which may have 1 to 10 (inclusive) carbon atoms in it; in more particular alkyl is $C_1$-$C_6$ alkyl group which may have 1 to 6 (inclusive) carbon atoms in it and in more preferred particular alkyl is $C_1$-$C_4$ alkyl group which may have 1 to 4 (inclusive) carbon atoms in it. Examples of alkyl groups include, but are not limited to, methyl, ethyl, propyl, butyl, pentyl, hexyl, isopropyl, isobutyl, sec-butyl, tert-butyl, isopentyl, neopentyl, and isohexyl. An alkyl group can be unsubstituted or substituted with one or more suitable groups.

The term "Cycloalkyl" refers to a non-aromatic, saturated or unsaturated, monocyclic, bicyclic or polycyclic hydrocarbon ring system. Representative examples of a cycloalkyl include, but are not limited to, cyclopropyl, cyclopentyl, cycloheptyl, cyclooctyl and the like. A cycloalkyl can be unsubstituted or substituted with one or more suitable groups.

The term "Heterocyclyl" includes the definitions of "heterocycloalkyl" and "heteroaryl". The term "Heterocycloalkyl" refers to a non-aromatic, saturated or partially saturated, monocyclic or polycyclic ring system of 3 to 10 member having at least one heteroatom or heterogroup selected from O, N, S, S(O), S(O)$_2$, NH and C(O). Exemplary heterocycloalkyl groups include piperidinyl, piperazinyl, morpholinyl, thiomorpholinyl, 1,3-dioxolanyl, 1,4-dioxanyl and the like. A heterocycloalkyl group can be unsubstituted or substituted with one or more suitable groups.

"Heteroaryl" refers to monocyclic, bicyclic, or polycyclic aromatic ring system containing at least one heteroatom selected from oxygen, sulphur and nitrogen. Examples of $C_5$-$C_{10}$ heteroaryl groups include furan, thiophene, indole, azaindole, oxazole, thiazole, thiadiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic heteroaryl groups include those where a phenyl, pyridine, pyrimidine or pyridazine ring is fused to a 5 or 6-membered monocyclic heterocyclyl ring having one or two nitrogen atoms in the ring, one nitrogen atom together with either one oxygen or one sulfur atom in the ring, or one O or S ring atom. A heteroaryl group can be unsubstituted or substituted with one or more suitable groups.

"Hetero atom" refers to a sulfur, nitrogen or oxygen atom.

The term "fused" as used herein with respect to two polyatomic, cyclic rings means that such rings have two adjacent atoms thereof common to both rings. The two adjacent atoms can be C or N. The fused ring can be 4-6 membered ring inclusive of the fused bond.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan and thiophene are 5-membered rings.

"Optionally substituted or substituted" as used herein means that at least one or two hydrogen atoms of the optionally substituted group has been substituted with suitable groups as exemplified but not limited to alkyl, alkenyl, alkoxy, alkynyl, aryl, amido, amino, carboxy, cyano, cycloalkyl, guanidine, halogen, imidamide, hydroxy, nitro, haloalkyl, haloalkoxy, heterocyclyl, oxo(=O), thio(=S), —P(O)$_3$H, —P(O)$_2$NH$_2$, —P(O)$_2$NH(alkyl), —P(O)$_2$NH (cycloalkyl), —P(O)$_2$NH(heterocyclyl), —P(O)$_2$NH(aryl), —C(O)(alkyl), —C(O)(aryl), —C(O)(cycloalkyl), —C(O) (heterocyclyl), or two substituents on the same carbon atom combined together to form an optionally substituted 3-8 member ring containing 0-3 heteroatoms independently selected form N, O and S in any stable combination.

"Comprise" or "Comprising" is generally used in the sense of include, that is to say permitting the presence of one or more features or components.

"Pharmaceutically acceptable salt" or "pharmaceutically acceptable derivatives" is taken to mean an active ingredient, which comprises a compound of the formula (1) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, phosphorous and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, oxalic, maleic, malic, mandelic, methanesulfonic, mucic, nitric, pamoic, pantothenic, phosphoric, succinic, sulfuric, tartaric, p-toluenesulfonic acid, and the like.

Different solid state forms (including solvated forms) of an active pharmaceutical ingredient may possess different properties. Such variations in the properties of different solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different solid state forms may also offer improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new polymorphic forms and solvates of a pharmaceutical product can provide materials having desirable processing properties, such as ease of handling, ease of processing, low hygroscopicity, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., different crystal habits, higher crystallinity or polymorphic stability which may offer better processing or handling characteristics, improved dissolution profile, or improved shelf-life. Lastly, new polymorphic forms may be prepared with improved reliability and reproducibility in manufacturing and processing compared to other forms, for example, in terms of crystallinity or polymorphic purity.

The term "solvate" means a complex or aggregate formed by one or more molecules of a solute, i.e. a crystalline compound of formula 1, and one or more molecules of a solvent. Such solvates typically have a substantially fixed molar ratio of solute and solvent. This term also includes clathrates, including clathrates with water. Representative solvents include, by way of example, water, methanol, ethanol, isopropanol, n-butanol, ethylene glycol, propylene glycol, ethyl acetate, tetrahydrofuran, 1,4-dioxane, acetonitrile and the like. When the solvent is water, the solvate formed is a hydrate.

The use of the term 'including" as well as other forms, such as "include", "includes" and "included" is not limiting.

As used herein, the terms "treat", "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. The terms "treat," "treating" or "treatment", include, but are not limited to, prophylactic and/or therapeutic treatments.

As used herein the terms "subject" or "patient" are well-recognized in the art, and, are used interchangeably herein to refer to a mammal, including dog, cat, rat, mouse, monkey, cow, horse, goat, sheep, pig, camel and most preferably a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

As used herein the term "therapeutically effective amount" refers to a sufficient amount of a compound or a composition being administered which will relieve to some extent one or more of the symptoms of the disease or condition being treated. The result can be reduction and/or alleviation of the signs, symptoms, or causes of a disease, or any other desired alteration of a biological system.

"Pharmaceutically acceptable" means that, which is useful in preparing a pharmaceutical composition that is generally safe, non-toxic, and neither biologically nor otherwise undesirable and includes that which is acceptable for veterinary as well as human pharmaceutical use.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; films, or oil-in-water liquid emulsions or water-in-oil liquid emulsions. For example, in the case of oral administration as tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

Tetrahydropyridine derivatives of formula (1), its pharmaceutically acceptable salts and stereoisomers thereof and the other active ingredients can also be administered as injectable dosages for iv, im, sc administrations. Tetrahydropyridine derivatives of formula (1), can specifically provided in the form of liposome delivery systems, such as, for example, small unilamellar vesicles, large unilamellar vesicles and multilamellar vesicles. Liposomes can be formed from suitable lipids or phospholipids or both, such as, for example, cholesterol, stearylamine or phosphatidylcholines or the like.

Pharmaceutical compounds adapted for topical administration can be formulated as ointments, creams, suspensions, lotions, powders, solutions, pastes, gels, sprays, aerosols or oils.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (1) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.001 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt of a physiologically functional derivative thereof can be determined as the fraction of the effective amount of the compound per se.

In yet another particular aspect of the present invention, FabI inhibitory compounds of formula (1) may have an advantage over the compounds known in the prior art. However the advantage can be in the form of more efficacious than, be longer acting than, less side effects than, less toxic than, more potent than, more easily absorbed than, or may have better pharmacokinetic profile and/or having good pharmacological, physiochemical characterizations than the compounds known in the prior art, for use in the above stated indications, which includes but are not limited to antibacterial infections.

The person skilled in the art in the treatment of antibacterial diseases linked to the inhibition of FabI enzyme will easily understand the compounds of formula (1) possessing advantageous properties over the prior art compounds by looking into the results herein after.

In particular instance, the advantage of the compounds of formula (1) may be FabI enzymatic inhibition assay results, wherein the $IC_{50}$ values of the most of the compounds of the present invention are less than 0.6 μM; preferably less than 0.4 μM.

In other instance, the compounds of formula (1) may have an advantage of having good antimicrobial activity, where most of the compounds of formula (1) are having MIC values (μg/mL) ≥16 μg/mL, ≥16 μg/mL and ≥32 μg/mL in MSSA, MSRA and MRSE organisms respectively; preferably ≥0.5 μg/mL, ≥0.5 μg/mL and ≥1 μg/mL. Moreover the compounds of formula (1) may have an advantage of having activity against drug resistant sratins in *Staphylococcus. aureus* (MRSA, QRSA and VISA starins) and in *Staphylococcus. epidermis* (MRSE and QRSE strains).

In another instance, the compound of formula (1) may have advantage of having metabolic stability over the prior art compounds; wherein the metabolic stability for some of the compounds of formula (1) shows greater than 50% remaining after 15 min and 60 min.

In yet another instance, the compounds of formula (1) may have advantage of having good in vivo efficacy; wherein the compound of the formula (1) may show good in vivo efficacy properties ($ED_{50}$) and may protect mice from mortality due to infection in different organisms such as MRSA 448, MRSA-446 and MSSA ATCC 29213. Moreover the compound of formula (1) may have an advantage of amenability from i.v. to oral switch.

In yet another instance, the compounds of formula (1) may have advantage of having good pharmacokinetic profile; wherein the compound of the formula (1) shows good oral bioavailability and plasma protein binding.

In yet another instance, the compound of formula (1) may have an advantage of not having any significant effect of serial passage on MIC (1-24 day) compared to other antibacterial drugs such as vanomycin and ciprofloxacin. Similarly the compound of present invention may have an advantage of having less effect of pulmonary surfactant on MIC (μg/ml) compared to other antibacterial agents such as Daptomycin in S. aureus and S. epidermis.

In another particular aspect, the present invention also relates to the process for preparation of tetrahydropyridine derivatives of formula (1).

An embodiment of the present invention provides the FabI inhibitor compounds according to formula (1) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{32}F$, $^{33}F$, $^{35}S$, $^{18}F$, $^{36}Cl$, $^{123}I$ and $^{125}I$. Isotopically labeled compounds of the present inventions can generally be prepared by following procedures analogous to those disclosed in the Schemes and/or in the examples herein below, by substituting an isotopically labeled reagent for a non-isotopically labeled reagent.

The abbreviations used in the entire specification may be summarized herein below with their particular meaning.

° C. (Degree celsius); % (Percentage), AcOH/CH$_3$COOH (Acetic acid); brine (NaCl solution); Br/Br$_2$ (Bromine); n-BuLi (n-Butyl lithium); brs/bs (Broad singlet); BF$_3$.Et$_2$O (Boron trifluoride.diethyl etherate), J (Coupling constant); Pd(dppf)$_2$Cl$_2$[1,1-Bis(diphenylphosphino) ferrocene dichloropalladium (II)]; DMF (N,N-Dimethyl formamide); DMSO (Dimethylsulphoxide); DMSO-d$_6$ (Deuterated Dimethylsulphoxide), DIPEA/DIEA (N,N-Diisopropyl ethylamine); CH$_2$Cl$_2$/DCM (Dichloromethane); d (Doublet); dd (Doublet of doublet); dt (Doublet of triplet); EDC.HCl (1-(3-Dimethyl aminopropyl)-3-carbodiimide hydrochloride); EtOH (Ethanol); H/H$_2$ (Hydrogen), HOBt (1-Hydroxy benzotriazole); HBr (Hydrobromic acid); HCl (Hydrochloric acid); h or hr (Hours); LAH (Lithium aluminium hydride); LDA (Lithium diisopropylamide); CH$_3$OH/MeOH (Methanol); MTBE (Methyl tert-butyl ether); mmol (Millimol); M (Molar); mL (Milliliter); mg (Milligram); m (Multiplet); MHz (Megahertz); ES-MS (Electro Spray-Mass Spectrometry); min (Minutes); LC-MS (Liquid Chromatography-Mass Spectrometry); N$_2$ (Nitrogen); NMR (Nuclear magnetic resonance spectroscopy); K$_2$CO$_3$ (Potassium carbonate); KOAc (Potassium acetate); Pd (OAc)$_2$ (Palladium di acetate); NaHCO$_3$ (Sodium bicarbonate), NaBH$_4$ (Sodium borohydride); Na$_2$CO$_3$ (Sodium carbonate), NaBH$_3$CN (Sodiumcyano borohydride); NaH (Sodium hydride), NaOH (Sodium hydroxide), Na$_2$SO$_4$ (Sodium sulphate); s (Singlet); THF (Tetrahydrofuran); SOCl$_2$ (Thionyl chloride), P (o-tolyl)$_3$ (tri-o-Tolyl phosphine); PTS-Cl (p-Toluene sulfonyl chloride), TEA (Triethylamine), TFA/CF$_3$COOH (Trifluoro acetic acid); SEM-Cl (2-(Trimethylsilyl)ethoxymethylchloride), t (Triplet); H$_2$O (Water), Zn (Zinc); CD-1 (Cluster of differentiation-1), KH$_2$PO$_4$ (Mono potassium phosphate), NADPH (nicotinamide adenine dinucleotide phosphate), NADH (Nicotinamide adenine dinucleotide) etc.

General Scheme:
General Procedure for the Preparation of Intermediates:

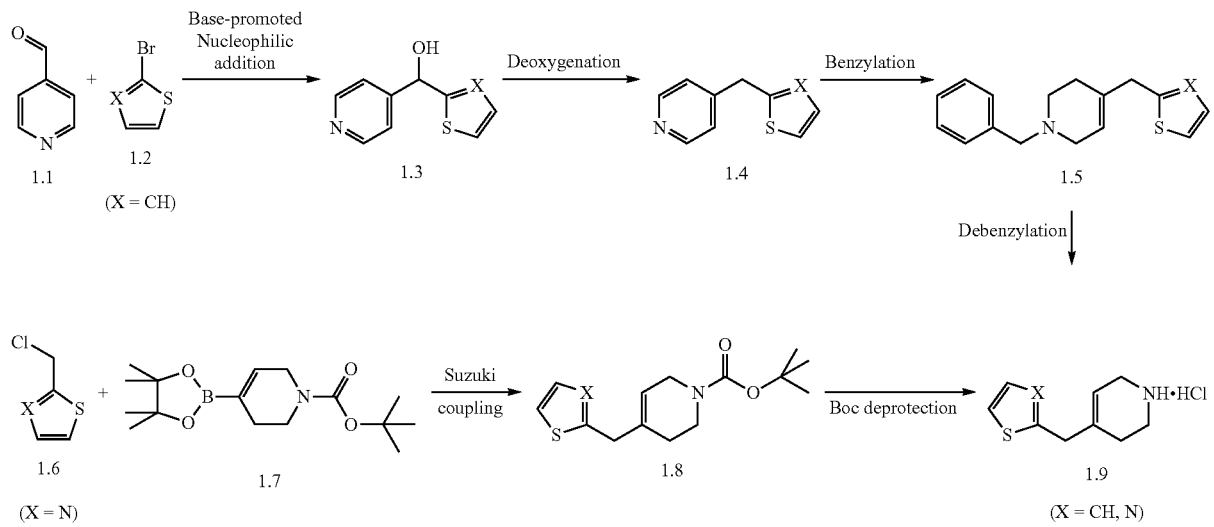

The formula 1.9 can be synthesized by treating formula 1.1 with formula 1.2 in the presence of suitable base such as n-BuLi and the like, in suitable solvents such as THF, diethyl ether and the like, at a temperature of about −78° C. to 20-35° C. for about 16-24 h. The formula 1.3 undergoes deoxygenation to provide formula 1.4 in presence of Zinc powder in suitable acidic solvent such as acetic acid and the like, at a temperature of about 20-35° C. to 120° C. for about 2-16 h. The formula 1.4 undergoes benzylation reaction in presence of reducing agents such as $NaBH_4$ and the like, in presence of suitable solvents such as DMF, ethanol, methanol and the like, at a temperature of about 70° C. to 100° C. for about 2-16 h to give formula 1.5. The debenzylation of formula 1.5 can be carried out by using the suitable debenzylating agent such as 1-chloroethyl chloroformate, TFA, HBr and the like, in suitable solvents such as DCM, methanol and the like, at a temperature of about 20-35° C. to 100° C. for about 1-16 h to provide formula 1.9.

The formula 1.6 undergoes Pd-catalyzed C—C coupling reaction (Suzuki coupling) with formula 1.7 to provide formula 1.8 in presence of suitable polar solvents such as THF, DMF, DMA, DMSO and the like, in presence of suitable bases such as $K_2CO_3$, $Cs_2CO_3$, $K_3PO_4$, $NaOBu^t$, NaOAc, NaOH and their molar solutions and the like, in presence of catalysts such as $Pd(dppf)_2Cl_2$, $Pd(PPh_3)_4$, $Pd_2(dba)_3$, $Pd(OAc)_2$ and the like, at a temperature of about 80-120° C. for about 16-48 h. The deprotection of formula 1.8 can be carried out by using the suitable deprotecting agents such as TFA, HCl in diethyl ether solutions and the like, in suitable solvents such as DCM, THF, DCM/THF (1:5) and the like, at a temperature of about 0° C. to 20-35° C. for about 2-6 h to provide formula 1.9.

General Procedure for the Preparation of Compounds of Formula (1):

As shown in the above scheme, the compounds of the present invention of formula (1) can be synthesized from formula 1.9 and 1.12 through acid-amine coupling, alternatively from formula 1.10 and 1.11 through Pd catalyzed C—C bond formation. The reactions progresses can be monitored by conventional methods such as TLC/NMR/LC-MS/ES-MS.

The formula 1.10 can be synthesized by treating formula 1.9 with acryloyl chloride in presence of suitable solvents such as DCM, THF, diethyl ether and the like, in the presence of suitable base such as triethylamine, pyridine and the like, at a temperature of about 0° C. to 20-35° C. for about 3-16 h.

Method-I: (Pd-Catalyzed C—C Bond Formation)

The formula (1) can be synthesized by treating formula 1.10 with formula 1.11 through Pd-catalyzed C—C coupling reaction. The Pd-catalyzed C—C coupling reaction can be carried out in suitable polar solvents such as DMF, propionitrile, ACN, THF or DMSO and the like, in a suitable organic bases such as TEA, DIPEA and the like by using catalysts such as $Pd(OAc)_2$, $Pd(PPh_3)_2Cl_2$, $Pd_2(dba)_3$ and the like, in the presence of ligands $P(o-tolyl)_3$, $P(m-tolyl)_3$, $P(p-tolyl)_3$ and the like, at a temperature of about 100-130° C. for about 12-48 h.

Method-II: (Acid-Amine Coupling)

The acid-amine coupling of formula 1.9 with formula 1.12 can be carried out by a conventional amide bond formation method by using a suitable coupling reagents such as benzotriazole-containing coupling reagents such as 1-hydroxybenzotriazole (HOBt), benzotriazole-1-yloxytris(dimethylamino)phosphoniumhexafluorophosphate and 2-(1H-benzotriazol-1-yl)-1,1,3,3-tetramethyluroniumhexafluorophosphate and an azabenzotriazole-containing reagent such

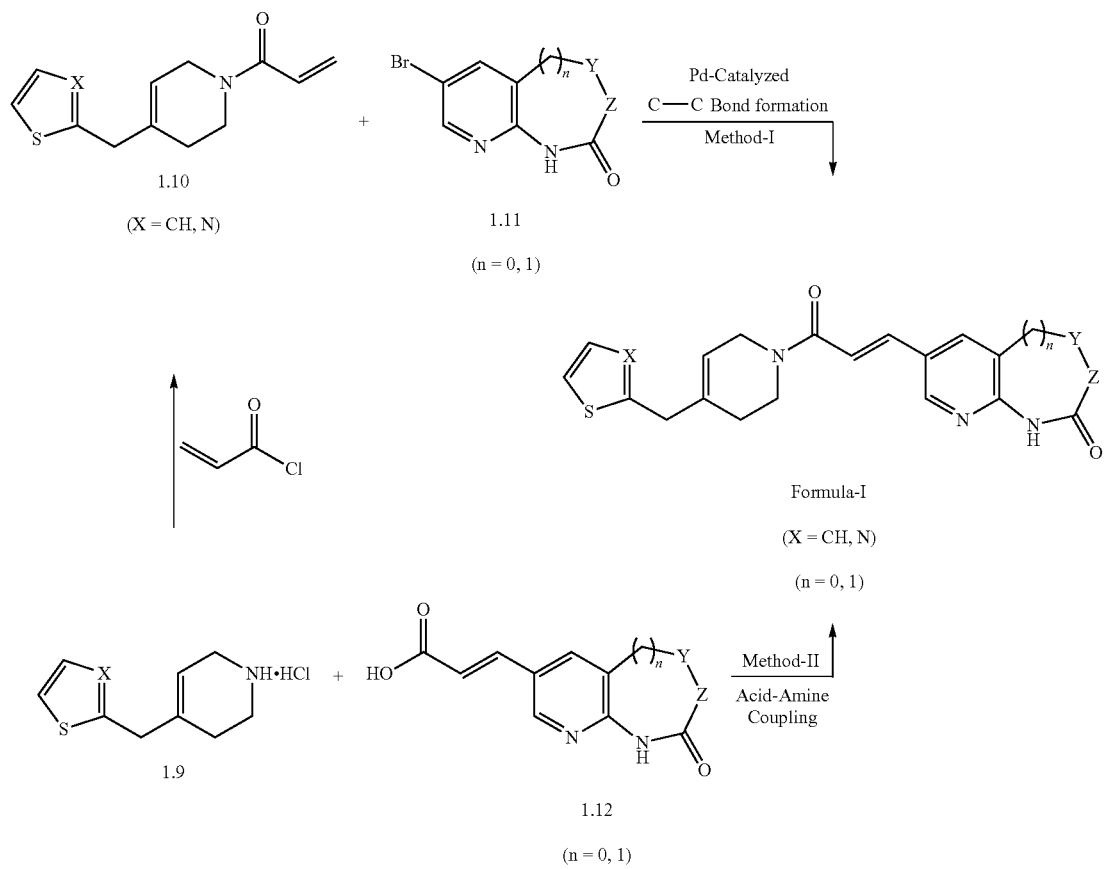

as O-(7-azabenzotriazole-1-yl)-N and also the dicarboimides containing reagent such as 1-ethyl-3-(3-dimethylaminopropyl) carbodiimide hydrochloride, dicyclohexylcarbodiimide, HATU and the like, in a suitable solvent such as DMF, THF, DMSO or DCM and the like, in the presence of suitable bases such as TEA, DIPEA and the like, at a temperature of about 20-35° C. for about 12-48 h to provide formula (1).

EXAMPLES

Although the invention has been illustrated by certain of the preceding examples, it is not to be construed as being limited thereby; but rather, the invention encompasses the generic area as herein before disclosed. Various modifications and embodiments can be made without departing from the spirit and scope thereof.

The MS data provided in the examples described below were obtained as follows:

Mass spectrum: LC/MS Agilent 6120 Quadrapole LC/MS.

The NMR data provided in the examples described below were obtained as follows:

¹H-NMR: Varian 400 MHz.

The procedure for the compounds of formula (1) are detailed herein below stepwise including the general synthesis of various intermediates involved in process of manufacture of the compounds according to the present invention.

Intermediate-1: Synthesis of 5-bromo-3-(bromomethyl)pyridin-2-amine hydrobromide

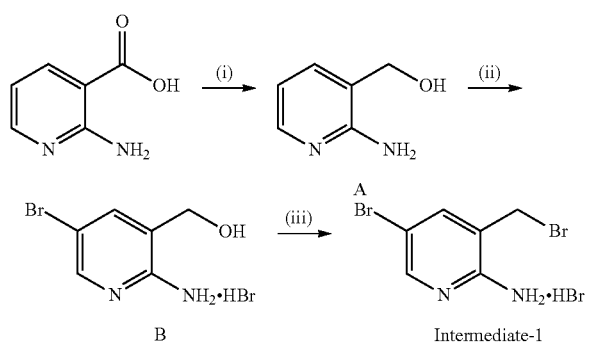

References for Step-(i): WO2005095391;
Step-(ii-iii): J. Med. Chem. 46, 2003, 1627-1635.

Intermediate-2: Synthesis of 2-((1,2,3,6-tetrahydropyridin-4-yl)methyl)thiazole hydrochloride

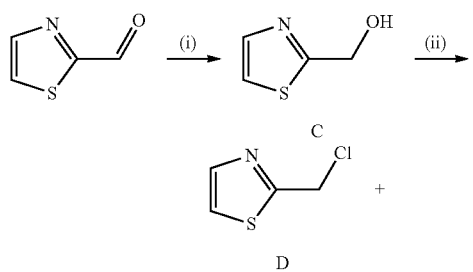

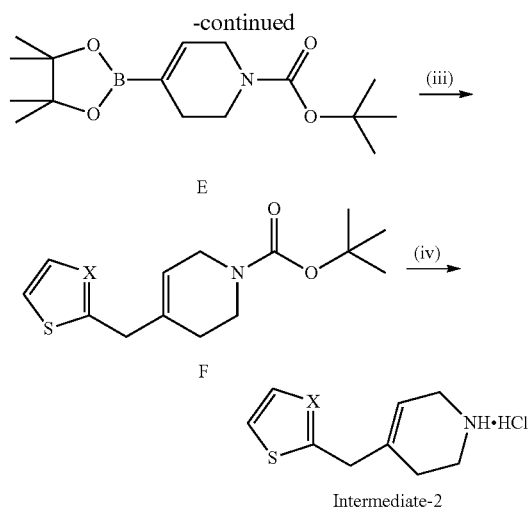

(Ref. for step-(i-ii): US2009/082403)

Step-(iii): Synthesis of tert-butyl 4-(thiazol-2-ylmethyl)-5,6-dihydropyridine-1(2H)-carboxylate (F)

To a stirred solution of 2-(chloromethyl)thiazole (D) (0.97 g, 6.46 mmol), tert-butyl 4-9(4,4,5,5-tetramethyl-1,3,2-dioxaborolan-2-yl)-5,6-dihydropyridine-1(2H)-carboxylate (E) (1 g, 3.23 mmol) in dry DMF (10 mL) was added $K_2CO_3$ (1.33 g, 9.69 mmol) at 20-35° C. and the mixture was degassed with $N_2$ for 10 minutes. Then $Pd(dppf)_2Cl_2$ (260 mg, 0.32 mmol) was added, again degassed with $N_2$ for another 10 minutes and heated at 110° C. for 14 h. Then the reaction mixture was cooled to 20-35° C., diluted with water (100 mL) and extracted with ethyl acetate (2×100 mL). The organic layer was washed with brine (100 mL), dried over anhydrous $Na_2SO_4$ and filtered. The filtrate was rotary evaporated under vacuum to get residue which was purified by column chromatography using a mixture of 30% ethyl acetate/hexane as an eluent to get the desired compound as a light brown liquid (400 mg, 44%); ¹H NMR (400 MHz, DMSO-$d_6$) δ 7.70 (d, J=3.4 Hz, 1H), 7.60 (d, J=3.5 Hz, 1H), 5.60 (s, 1H), 3.82 (s, 2H), 3.71 (s, 2H), 3.38 (t, J=5.9 Hz, 2H), 2.06-1.96 (m, 2H), 1.40 (s, 9H).

Step-(iv): Synthesis of 2-((1,2,3,6-tetrahydropyridin-4-yl)methyl)thiazole hydrochloric acid (Intermediate-2)

To a stirred solution of tert-butyl 4-(thiazol-2-ylmethyl)-5,6-dihydropyridine-1(2H)-carboxylate (F) (1.5 g, 5.36 mmol) in $CH_2Cl_2$ (20 mL) was added 2M HCl in diethyl ether (5 mL) dropwise at 0° C. and the reaction mixture was allowed to stir at 20-35° C. for 2 h. Then the reaction mixture was rotary evaporated under vacuum to get the desired compound as a brown liquid (1.6 g); ¹H NMR (400 MHz, DMSO-$d_6$) δ 9.23 (bs, 2H), 7.77 (d, J=2.5 Hz, 1H), 7.68 (d, J=3.2 Hz, 1H), 5.61 (s, 1H), 3.80 (s, 2H), 3.58-3.54 (m, 2H), 3.15-3.11 (m, 2H), 2.27-2.23 (m, 2H).

Intermediate-3: Synthesis of 4-(thiophen-2-ylmethyl)-1,2,3,6-tetrahydropyridine hydrochloride

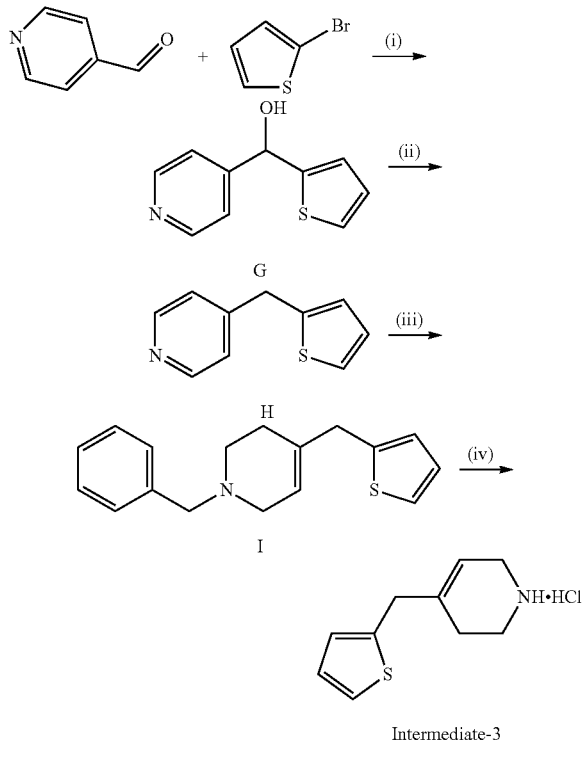

Intermediate-3

Step-(i): Synthesis of pyridin-4-yl(thiophen-2-yl)methanol (G)

To a stirred solution of 2-bromothiophene (10 g, 61.34 mmol) in dry THF (42 mL) was added n-butyl lithium (42.0 mL, 67.48 mmol) dropwise at −78° C. and the mixture was stirred at same temperature for 30 min. Then a solution of isonicotinaldehyde (6.56 g, 61.34 mmol) in dry THF (30 mL) was added dropwise and continued stirring at −78° C. for another 2 h. The reaction mixture was quenched with NH$_4$Cl solution (10 mL), diluted with water (200 mL) and extracted with diethyl ether (2×200 mL). The organic layer was washed with brine (100 mL), dried over anhydrous Na$_2$SO$_4$ and filtered. The filtrate was rotary evaporated under vacuum to get residue which was triturated with mixture of hexane and diethyl ether to get the desired compound as an off-white solid (4 g, 34%); $^1$H NMR (400 MHz, DMSO-d$_6$) δ 8.52 (dd, J=4.9 Hz, 1.5 Hz, 2H), 7.45-7.38 (m, 3H), 6.97-6.93 (m, 2H), 6.45 (d, J=4.4 Hz, 1H), 5.97 (d, J=4.4 Hz, 1H).

Step-(ii): Synthesis of 4-(thiophen-2-ylmethyl)pyridine (H)

To a stirred solution of pyridin-4-yl(thiophen-2-yl)methanol (G) (4 g, 20.94 mmol) in acetic acid (40 mL) was added Zn powder (11.69 g, 208.73 mmol) portion wise at 70° C. and the reaction mixture was allowed to reflux for 16 h. Then the reaction mixture was filtered through Celite® and the filtrate was rotary evaporated. The resultant residue was diluted with water (50 mL), basified with Na$_2$CO$_3$ solution to pH 9 at 0° C. and extracted with diethyl ether (2×100 mL). The organic layer was washed with brine (100 mL), dried over anhydrous Na$_2$SO$_4$ and filtered. The filtrate was rotary evaporated under vacuum to get the desired compound as an oily liquid (3.2 g, 87%); $^1$H NMR (400 MHz, DMSO-d$_6$) δ 8.48 (dd, J=1.5 Hz, 4.4 Hz, 2H), 7.37 (dd, J=1.5 Hz, 4.9 Hz, 1H), 7.26 (d, J=5.9 Hz, 2H), 6.99-6.93 (m, 2H), 4.19 (s, 2H).

Step-(iii): Synthesis of 1-benzyl-4-(thiophen-2-ylmethyl)-1,2,3,6-tetrahydropyridine (I)

To a stirred solution of 4-(thiophen-2-ylmethyl)pyridine (H) (3.1 g, 11.52 mmol) in DMF (10 mL) was added benzyl bromide (2.16 g, 12.67 mmol) at 20-35° C. and the reaction mixture was allowed to stir at 100° C. for 3 h. Then the reaction mixture was cooled to 20-35° C., diluted with ethanol (30 mL) and NaBH$_4$ (0.65 g, 17.28 mmol) was added slowly portionwise at 0° C. and then heated at 70-80° C. for 2 h. The reaction mixture was rotary evaporated, resultant residue was diluted with water (50 mL) and extracted with ethyl acetate (2×50 mL). The organic layer was washed with brine (50 mL), dried over anhydrous Na$_2$SO$_4$ and filtered. The filtrate was rotary evaporated under vacuum to get residue which was purified by column chromatography using a mixture of 20% ethyl acetate/hexane as an eluent to get the desired compound as a light brown oily liquid (3.3 g, 67%); $^1$H NMR (400 MHz, DMSO-d$_6$) δ 7.33-7.28 (m, 5H), 7.28-7.22 (m, 1H), 6.94 (dd, J=3.4, 5.4 Hz, 1H), 6.84-6.82 (m, 1H), 5.46 (s, 1H), 3.51 (s, 2H), 3.46 (s, 2H), 2.87 (s, 2H), 2.46 (t, J=5.9 Hz, 2H), 1.98 (s, 2H).

Step-(iv): Synthesis of 4-(thiophen-2-ylmethyl)-1,2,3,6-tetrahydropyridine hydrochloride (Intermediate-3)

To a stirred solution of 1-benzyl-4-(thiophen-2-ylmethyl)-1,2,3,6-tetra hydropyridine (1) (3.3 g, 12.26 mmol) in dichloromethane (30 mL) was added 1-chloroethyl chloroformate (12.27 g, 85.87 mmol) at 0° C. and the reaction mixture was allowed to stir at 20-35° C. for 3 h. Then the reaction mixture was diluted with water (50 mL) and extracted with dichloromethane (50 mL). The organic layer was washed with brine (50 mL), dried over anhydrous Na$_2$SO$_4$ and filtered. The filtrate was rotary evaporated to get residue; which was dissolved in methanol (20 mL) and heated at 70-80° C. for 1 h. The reaction mixture was rotary evaporated under vacuum to get residue which was triturated with diethyl ether to get the desired compound as a brown solid (2.5 g); $^1$H NMR (400 MHz, DMSO-d$_6$) δ 9.04-8.92 (m, 2H), 7.38 (dd, J=1.5, 5.4 Hz, 1H), 6.97 (dd, J=3.4, 5.4 Hz, 1H), 6.90 (dd, J=1.0, 3.4 Hz, 1H), 5.54 (s, 1H), 3.56 (s, 2H), 3.54-3.52 (m, 2H), 3.14-3.11 (m, 2H), 2.24-2.16 (m, 2H).

Intermediate-4: Synthesis of 1-(4-(thiazol-2-ylmethyl)-5,6-dihydropyridin-1(2H)-yl)prop-2-en-1-one

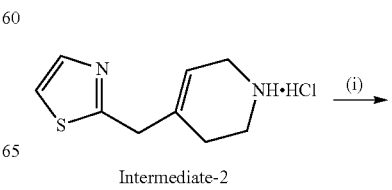

Intermediate-2

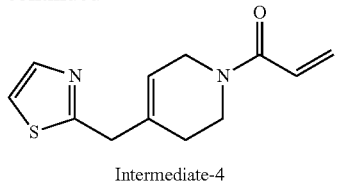

Intermediate-4

To a stirred suspension of 2-((1,2,3,6-tetrahydropyridin-4-yl)methyl)thiazole hydrochloride (Intermediate-2) (1.57 g, 5.34 mmol) in anhydrous $CH_2Cl_2$ (20 mL) was added triethylamine (4.4 mL, 32.0 mmol), followed by acryloyl chloride (1.3 mL, 16.0 mmol) at 0° C. and the reaction mixture was allowed to stir at 20-35° C. for 16 h. Then the reaction mixture was diluted with water (50 mL) and extracted with ethyl acetate (2×50 mL). The organic layer was washed with brine (50 mL), dried over anhydrous $Na_2SO_4$ and filtered. The filtrate was rotary evaporated under vacuum to get residue which was purified by column chromatography using a mixture of 20% ethyl acetate/hexane as an eluent to get the desired compound as a light brown liquid (320 mg, 26%); $^1$H NMR (400 MHz, DMSO-$d_6$) δ 7.71 (d, J=3.4 Hz, 1H), 7.60 (d, J=2.9 Hz, 1H), 6.88-6.70 (m, 1H), 6.14-6.08 (m, 1H), 5.72-5.60 (m, 2H), 4.12-4.08 (m, 1H), 4.06-3.96 (m, 1H), 3.74-3.70 (m, 2H), 3.66-3.54 (m, 2H), 2.12-2.02 (m, 2H); ES-MS: 235.1 (M+1)$^+$.

Intermediate-5 was prepared according to the above protocol by using intermediate-3 as starting compound at suitable conditions.

| Int No. | Structure | Characterization data ($^1$H NMR (400 MHz, DMSO-$d_6$) & ES-MS) |
|---|---|---|
| 5 | 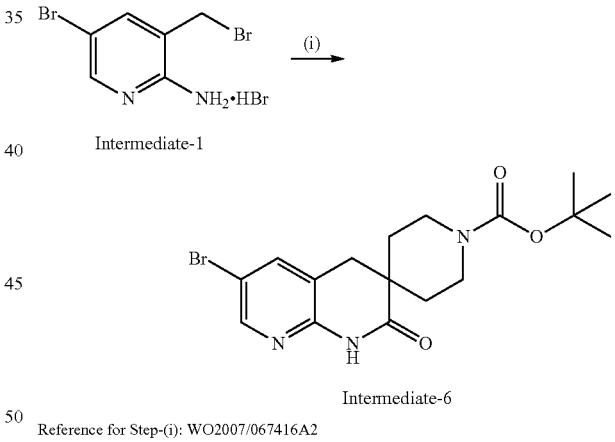 | δ 7.34 (dd, J = 1.0, 5.4 Hz, 1H), 6.95 (dd, J = 3.4, 4.9 Hz, 1H), 6.86 (d, J = 2.5 Hz, 1H), 6.80 (dd, J = 10.3, 16.6 Hz, 1H), 6.14-6.06 (m, 1H), 5.66 (dt, J = 2.5, 4.9 Hz, 1H), 5.57-5.51 (m, 1H), 3.98 (s, 2H), 3.62-3.3.55 (m, 2H), 3.52 (s, 2H), 2.08-2.02 (m, 2H); ES-MS: 234.1 (M + 1)$^+$. |

Intermediate-6: Synthesis of tert-butyl 6-bromo-2-oxo-2,4-dihydro-1H-spiro[[1,8]naphthyridine-3,4'-piperidine]-1'-carboxylate Reference for Step-(i): WO2007/067416A2

The below Intermediates-7 to 13 were prepared according to the above protocol (intermediate-6) by using appropriate reactants, reagents at suitable conditions. The physiochemical characteristics of the intermediates are summarized herein.

| Int No. | Structure | Characterization data $^1$H NMR (400 MHz, DMSO-$d_6$) δ |
|---|---|---|
| 7 | 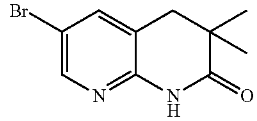 | δ 10.59 (bs, 1H), 8.21 (d, J = 2.5 Hz, 1H), 7.85 (d, J = 2.1 Hz, 1H), 2.79 (s, 2H), 1.06 (s, 6H). |

| Int No. | Structure | Characterization data<br>¹H NMR (400 MHz, DMSO-d₆) δ |
|---|---|---|
| 8 | 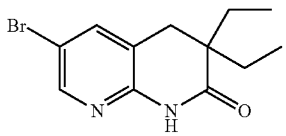 [SMILES: CCC1(CC)Cc2cc(Br)cnc2NC1=O] | δ 10.58 (s, 1H), 8.19 (d, J = 2.0 Hz, 1H), 7.86 (d, J = 2.0 Hz, 1H), 2.81 (s, 2H), 1.54-1.38 (m, 4H), 0.79 (t, J = 7.3 Hz, 6H). |
| 9 | 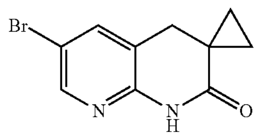 [SMILES: O=C1Nc2ncc(Br)cc2CC12CC2] | δ 10.69 (bs, 1H), 8.23 (d, J = 2.4 Hz, 1H), 7.77 (d, J = 1.5 Hz, 1H), 2.87 (s, 2H), 1.13-1.10 (m, 2H), 0.80-0.76 (m, 2H). |
| 10 | 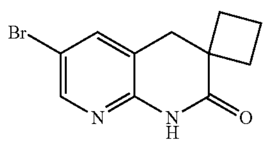 [SMILES: O=C1Nc2ncc(Br)cc2CC12CCC2] | δ 10.55 (s, 1H), 8.20 (d, J = 1.9 Hz, 1H), 7.88 (d, J = 1.9 Hz, 1H), 3.06 (s, 2H), 2.36-2.26 (m, 2H), 2.04-1.94 (m, 1H), 1.93-1.82 (m, 1H), 1.80-1.72 (m, 2H). |
| 11 | 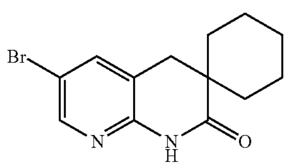 [SMILES: O=C1Nc2ncc(Br)cc2CC12CCCCC2] | δ 10.55 (bs, 1H), 8.19 (d, J = 2.4 Hz, 1H), 7.89 (d, J = 1.5 Hz, 1H), 2.90 (s, 2H), 1.66-1.59 (m, 2H), 1.54 (d, J = 7.6 Hz, 2H), 1.43 (d, J = 10.8 Hz, 2H), 1.27 (t, J = 12.8 Hz, 4H). |
| 12 | 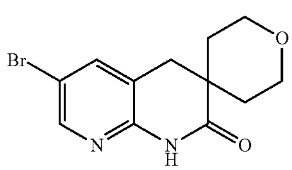 [SMILES: O=C1Nc2ncc(Br)cc2CC12CCOCC2] | δ 10.68 (bs, 1H), 8.22 (d, J = 1.9 Hz, 1H), 7.88 (d, J = 1.5 Hz, 1H), 3.71-3.66 (m, 2H), 3.62 (dd, J = 2.9, 8.3 Hz, 2H), 2.99 (s, 2H), 1.82-1.76 (m, 2H), 1.31-1.27 (m, 2H). |
| 13 | 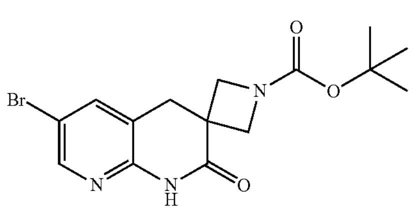 [SMILES: CC(C)(C)OC(=O)N1CC2(Cc3cc(Br)cnc3NC2=O)C1] | δ 10.89 (bs, 1H), 8.24 (d, J = 1.9 Hz, 1H), 7.89 (d, J = 2.0 Hz, 1H), 4.08-3.98 (m, 2H), 3.68-3.58 (m, 2H), 3.25 (s, 2H), 1.37 (s, 9H). |

Intermediates-14: Synthesis of 6-bromo-1H-spiro[[1,8]naphthyridine-3,4'-piperidin]-2(4H)-one 2,2,2-trifluoroacetate

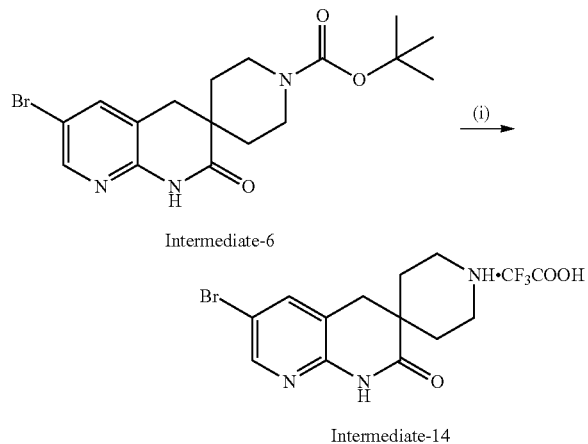

Intermediate-6

(i)

Intermediate-14

(i) (Reference for Step-(i): WO2013/080222A1)

Intermediates-14.1: Synthesis of 6-bromo-1'-pivaloyl-1H-spiro[[1,8]naphthyridine-3,4'-piperidin]-2(4H)-one

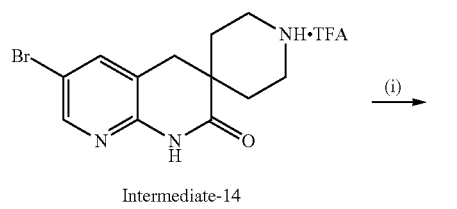

Intermediate-14

(i)

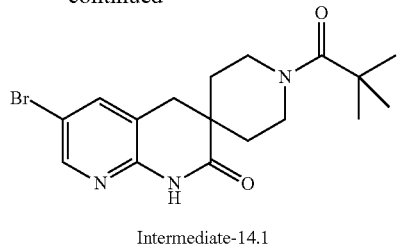

Intermediate-14.1

To a stirred solution of 6-bromo-1H-spiro[[1,8]naphthyridine-3,4'-piperidin]-2(4H)-one 2,2,2-trifluoroacetate (Intermediate-14) (100 mg, 0.24 mmol) in DCM (3 mL) were added triethylamine (0.1 mL, 0.72 mmol) and pivaloyl chloride (40 mg, 0.32 mmol) at 20-35° C. and the reaction mixture was allowed to stir at 20-35° C. for 16 h. Then the reaction mixture was diluted with water (30 mL) and extracted with DCM (2×30 mL). The organic layer was washed with brine (50 mL), dried over anhydrous $Na_2SO_4$ and filtered. The filtrate was rotary evaporated under vacuum to get residue which was purified by column chromatography using mixture of 60% ethyl acetate/hexane as an eluent to get the desired compound as a creamy white solid (50 mg, 55%); $^1$H NMR (400 MHz, DMSO-$d_6$) δ 10.73 (s, 1H), 8.23 (d, J=1.9 Hz, 1H), 7.85 (d, J=1.5 Hz, 1H), 3.79-3.74 (m, 2H), 3.44 (t, J=10.1 Hz, 2H), 2.99 (s, 2H), 1.75-1.68 (m, 2H), 1.35-1.29 (m, 2H), 1.18 (s, 9H); ES-MS: 380.2 (M+1)$^+$.

The below Intermediates-14.2 and 14.3 were prepared according to the above protocol (Intermediate-14.1) by using DIPEA instead of triethylamine at suitable conditions. The physiochemical characteristics of the intermediates are summarized herein.

| Int No. | Structure | Characterization data ($^1$H NMR (400 MHz, DMSO-$d_6$) & LC-MS) |
|---|---|---|
| 14.2 | 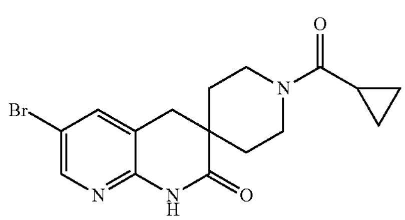 [SMILES: O=C(C1CC1)N1CCC2(CC1)Cc1cc(Br)cnc1NC2=O] | δ 10.73 (s, 1H), 8.23 (s, 1H), 7.85 (s, 1H), 3.86-3.71 (m, 2H), 3.63-3.57 (m, 2H), 3.26-3.16 (m, 1H), 3.00 (s, 2H), 1.97-1.93 (m, 1H), 1.86-1.74 (m, 1H), 1.72-1.60 (m, 1H), 1.46-1.27 (m, 1H), 0.73-0.66 (m, 4H); LC-MS: 366.2 (M + 1)$^+$. |
| 14.3 | 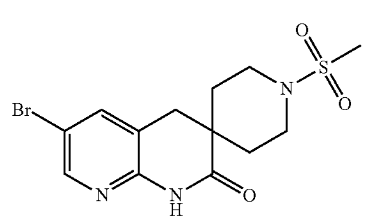 [SMILES: CS(=O)(=O)N1CCC2(CC1)Cc1cc(Br)cnc1NC2=O] | δ 10.76 (s, 1H), 8.23 (s, 1H), 7.85 (s, 1H), 3.28-3.25 (m, 2H), 3.16-3.10 (m, 2H), 3.00 (s, 2H), 2.88 (s, 3H), 1.87-1.84 (m, 2H), 1.47-1.44 (m, 2H); LC-MS: 376.2 (M + 1)$^+$. |

Intermediates-14.4: Synthesis of 6-bromo-1'-(cyclopentanecarbonyl)-1H-spiro[[1,8]naphthyridine-3,4'-piperidin]-2(4H)-one

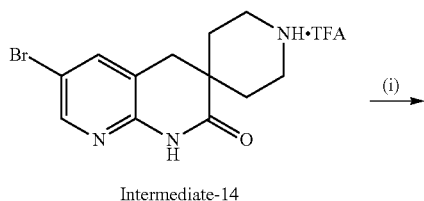

Intermediate-14

DIPEA (1.22 mL, 8.82 mmol) was added to a stirred solution of 6-bromo-1H-spiro[[1,8]naphthyridine-3,4'-piperidin]-2(4H)-one 2,2,2-trifluoroacetate (Intermediate-14) (600 mg, 1.47 mmol), cyclopentanecarboxylic acid (250 mg, 2.20 mmol), HOBt (390 mg, 2.94 mmol) and EDC.HCl (700 mg, 3.67 mmol) in dry DMF (5 mL) at 20-35° C. and the reaction mixture was allowed to stir at 20-35° C. for 16 h. Then the reaction mixture was poured into ice water (100 mL), obtained solid was filtered, washed with water and dried under vacuum to get the desired compound as an off-white solid (250 mg, 43%); $^1$H NMR (400 MHz, DMSO-d$_6$) δ 10.74 (s, 1H), 8.23 (d, J=2.0 Hz, 1H), 7.86 (d, J=1.9 Hz, 1H), 3.76-3.67 (m, 3H), 3.47-3.41 (m, 1H), 2.99 (s, 2H), 2.96-2.94 (m, 1H), 1.90-1.72 (m, 4H), 1.71-1.56 (m, 4H), 1.55-1.42 (m, 2H), 1.38-1.23 (m, 2H).

The below Intermediates-14.5 and 14.7 were prepared according to the above protocol (Intermediate-14.4) by using appropriate reactants and reagents at suitable conditions. The physiochemical characteristics of the intermediates are summarized herein.

| Int No. | Structure | Characterization data |
|---|---|---|
| 14.5 | 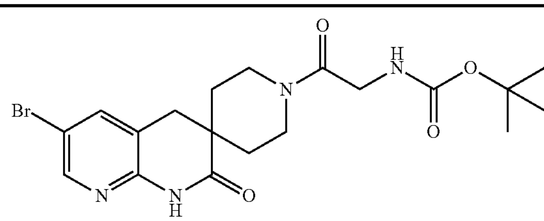 | $^1$H NMR (400 MHz, DMSO-d$_6$) δ 10.73 (s, 1H), 8.23 (d, J = 2.5 Hz, 1H), 7.87 (d, J = 1.4 Hz, 1H), 6.70 (t, J = 5.4 Hz, 1H), 3.77 (d, J = 5.4 Hz, 2H), 2.98 (s, 2H), 1.80 (t, J = 9.8 Hz, 1H), 1.67 (t, J = 9.8 Hz, 1H), 1.42-1.28 (m, 2H), 1.38 (s, 9H), 1.20-1.10 (m, 4H). |
| 14.6 | 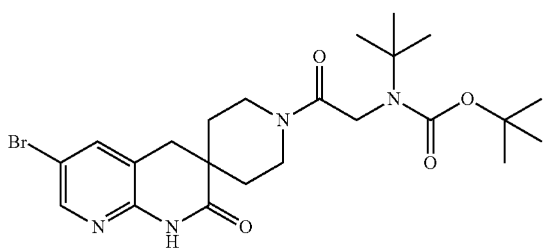 [SMILES: CC(C)(C)OC(=O)N(CC(=O)N1CCC2(CC1)Cc1cc(Br)cnc1NC2=O)C(C)(C)C] | $^1$H NMR (400 MHz, DMSO-d$_6$) δ 10.73 (s, 1H), 8.24 (s, 1H), 7.88 (d, J = 1.9 Hz, 1H), 4.12-4.01 (m, 2H), 3.79-3.77 (m, 1H), 3.75-3.73 (m, 1H), 2.99 (s, 2H), 2.32-2.30 (m, 2H), 1.80-1.78 (m, 1H), 1.67-1.65 (m, 1H), 1.36 (s, 9H), 1.33 (s, 9H), 1.15-1.13 (m, 2H). |
| 14.7 | 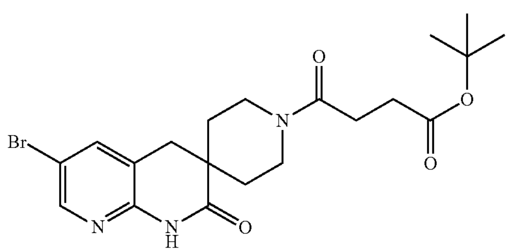 [SMILES: CC(C)(C)OC(=O)CCC(=O)N1CCC2(CC1)Cc1cc(Br)cnc1NC2=O] | $^1$H NMR (400 MHz, DMSO-d$_6$) δ 10.71 (s, 1H), 8.21 (d, J = 2.5 Hz, 1H), 7.85 (d, J = 1.9 Hz, 1H), 3.78-3.71 (m, 1H), 3.70-3.54 (m, 1H), 3.46-3.36 (m, 1H), 3.35-3.24 (m, 1H), 2.96 (s, 2H), 2.56-2.42 (m, 2H), 2.41-2.34 (m, 2H), 1.84-1.76 (m, 1H), 1.70-1.58 (m, 1H), 1.42-1.19 (m, 2H), 1.36 (s, 9H). |

-continued

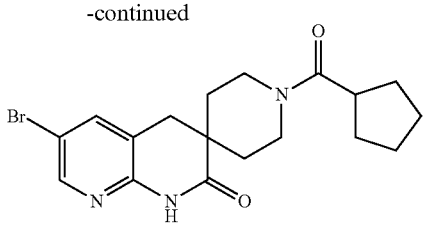

Intermediate-14.4

Intermediate-14.8: Synthesis of 6-bromo-N-(tert-butyl)-2-oxo-2,4-dihydro-1H-spiro[[1,8]naphthyridine-3,4'-piperidine]-1'-carboxamide

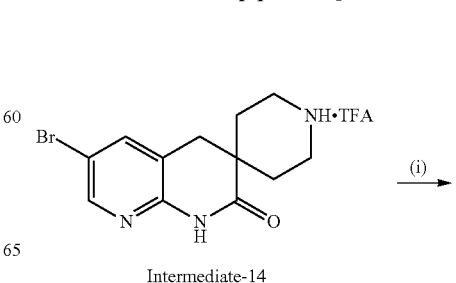

Intermediate-14

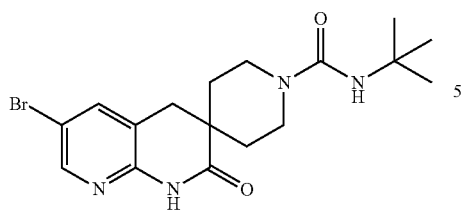

Intermediate-14.8

To a stirred solution of 6-bromo-1H-spiro[[1,8]naphthyridine-3,4'-piperidin]-2(4H)-one 2,2,2-trifluoroacetate (Intermediate-14) (500 mg, 1.22 mmol) in DMSO (5 mL) were added triethylamine (370 mg, 3.66 mmol) and phenyl tert-butylcarbamate (490 mg, 2.44 mmol) at 20-35° C. and the reaction mixture was allowed to stir at 70° C. for 16 h. Then the reaction mixture was diluted with water (100 mL) and extracted with DCM (2×100 mL). The organic layer was washed with brine (100 mL), dried over anhydrous Na$_2$SO$_4$ and filtered. The filtrate was rotary evaporated under vacuum to get residue which was purified by column chromatography using mixture of 2% methanol/dichloromethane as an eluent to get the desired compound as an off-white solid (250 mg, 52%); $^1$H NMR (400 MHz, DMSO-d$_6$) δ 10.67 (s, 1H), 8.22 (d, J=2.5 Hz, 1H), 7.87 (d, J=2.0 Hz, 1H), 5.74 (d, J=10.5 Hz, 1H), 3.52 (dt, J=4.4 Hz, 9.5 Hz, 2H), 3.16-3.08 (m, 2H), 2.95 (s, 2H), 1.73-1.65 (m, 2H), 1.34-1.23 (m, 11H); LC-MS: 397.2 (M+1)$^+$.

Intermediate-15: Synthesis of 1'-(azetidine-1-carbonyl)-6-bromo-1H-spiro[[1,8]naphthyridine-3,4'-piperidin]-2(4H)-one

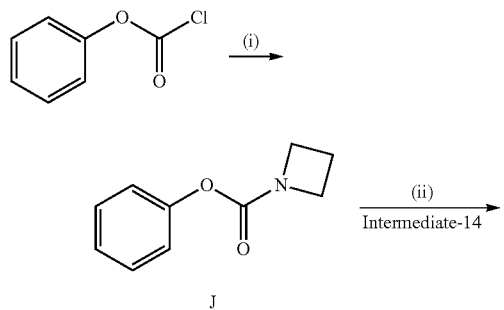

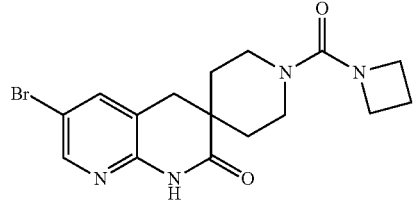

Intermediate-15

Step-(i): Synthesis of phenyl azetidine-1-carboxylate (J)

To a stirred solution of azetidine (2 g, 35.08 mmol) in DCM (25 mL) were added triethylamine (14.4 mL, 105.24 mmol), followed by phenyl chloroformate (5.5 mL, 42.10 mmol) at 0° C. and the reaction mixture was allowed to stir at 20-35° C. for 16 h. Then the reaction mixture was diluted with water (30 mL) and extracted with DCM (2×50 mL). The organic layer was washed with brine (30 mL), dried over anhydrous Na$_2$SO$_4$ and filtered. The filtrate was rotary evaporated under vacuum to get residue which was purified by column chromatography using mixture of 5% MeOH/DCM as an eluent to get the desired compound as a white solid (4.5 g, 72%). $^1$H NMR (400 MHz, DMSO-d$_6$) δ 7.39-7.35 (m, 2H), 7.22-7.18 (m, 1H), 7.12-7.08 (m, 2H), 4.20-4.08 (m, 2H), 4.04-3.92 (m, 2H), 2.29-2.21 (m, 2H).

Step-(ii): Synthesis of 1'-(azetidine-1-carbonyl)-6-bromo-1H-spiro[[1,8]naphthyridine-3,4'-piperidin]-2(4H)-one (Intermediate-15)

To a stirred solution of 6-bromo-1H-spiro[[1,8]naphthyridine-3,4'-piperidin]-2(4H)-one 2,2,2-trifluoroacetate (Intermediate-14) (600 mg, 1.47 mmol) in DMSO (5 mL) was added triethylamine (0.60 mL, 4.40 mmol) at 0° C. and the mixture was stirred at the same temperature for 15 min. Then phenyl azetidine-1-carboxylate (J) (520 mg, 2.93 mmol) was added and the reaction mixture was allowed to stir at 100° C. for 24 h. The reaction mixture was cooled to 20-35° C., diluted with ice cold water (30 mL) and extracted with ethyl acetate (2×50 mL). The organic layer was washed with brine (30 mL), dried over anhydrous Na$_2$SO$_4$ and filtered. The filtrate was rotary evaporated under vacuum to get residue; which was purified by column chromatography using mixture of 3% MeOH/DCM as an eluent to get the desired compound as a brown solid (180 mg, 32%); $^1$H NMR (400 MHz, DMSO-d$_6$) δ 10.70 (s, 1H), 8.22 (d. J=1.5 Hz, 1H), 7.86 (d, J=1.9 Hz, 1H), 3.86 (t, J=7.8 Hz, 4H), 3.43-3.36 (m, 2H), 3.21-3.13 (m, 2H), 2.96 (s, 2H), 2.18-2.10 (m, 2H), 1.73-1.67 (m, 2H), 1.34-1.23 (m, 2H).

The below Intermediate-16 was prepared according to the above protocol (Intermediate-15) with appropriate starting compound; wherein step-(i) reaction is conducted in presence of NaHCO$_3$ and combination of DCM/H$_2$O (1:1).

| Int No. | Structure | Characterization data ($^1$H NMR (400 MHz, DMSO-d$_6$) & LC-MS) |
|---|---|---|
| 16 | 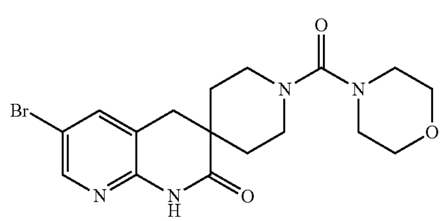 [SMILES: O=C(N1CCOCC1)N1CCC2(CC1)Cc1cc(Br)cnc1NC2=O] | δ 10.68 (s, 1H), 8.20 (d, J = 2.4 Hz, 1H), 8.09 (d, J = 1.0 Hz, 1H), 3.56-3.48 (m, 4H), 3.38-3.26 (m, 2H), 3.16-3.09 (m, 2H), 3.08-3.01 (m, 4H), 2.94 (s, 2H), 1.78-1.68 (m, 2H), 1.34-1.28 (m, 2H); LC-MS: 409.2 (M + 1)$^+$. |

Intermediate-17: Synthesis of 3-bromo-6,7-dihydro-5H-pyrido[2,3-b]azepin-8(9H)-one

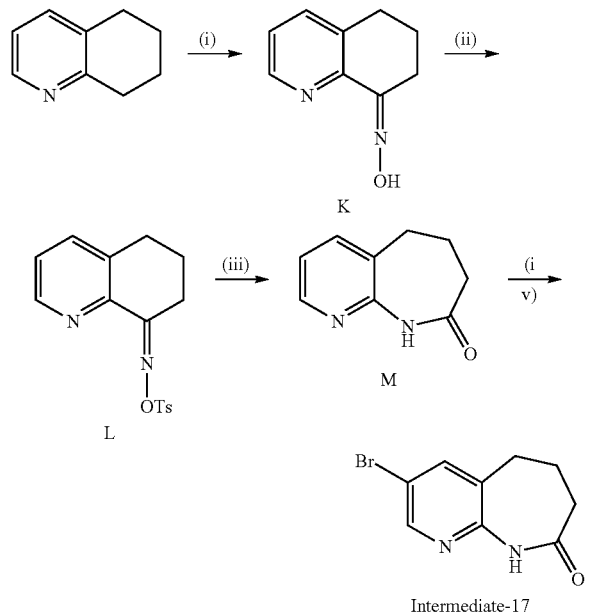

(Ref. for step-(i): *Synthetic communications, 33*(20), 2003, 3497; (Ref. for step-(ii-iv): WO2007/067416)

Intermediate-18 & 19: Synthesis of 6'-bromo-1'H-spiro[azepane-4,3'-[1,8]naphthyridine]-2',7(4'H)-dione & 6'-bromo-1-methyl-1'H-spiro[azepane-4,3'-[1,8]naphthyridine]-2',7(4'H)-dione

Step-(i): Synthesis of ethyl 1,4-dithiaspiro[4.5]decane-8-carboxylate (N)

To a stirred solution of ethyl 4-oxocyclohexane carboxylate (5 g, 29.41 mmol) and ethane-1,2-dithiol (4.14 g, 44.11 mmol) in DCM (25 mL) was added $BF_3 \cdot Et_2O$ (4.17 g, 29.41 mmol) at 0° C. and the reaction mixture was allowed to stir at 20-35° C. for 2 h. Then the reaction mixture was rotary evaporated under vacuum to get residue which was purified by column chromatography using mixture of 5% ethyl acetate/hexane as an eluent to get the desired compound as a yellow liquid (5.4 g, 75%); $^1$H NMR (400 MHz, DMSO-$d_6$) δ 4.05 (q, J=7.4 Hz, 2H), 3.34-3.26 (m, 4H), 2.42-2.34 (m, 1H), 2.10-2.02 (m, 2H), 1.96-1.84 (m, 4H), 1.66-1.54 (m, 2H), 1.17 (t, J=7.3 Hz, 3H).

Step-(ii): Synthesis of ethyl 1,4-dithiaspiro[4.5]decane-8-carboxylate (O)

The process of this step was adopted from preparation of Intermediate-6. The desired compound obtained as an off-white solid (0.85 g, 30%); NMR (400 MHz, DMSO-$d_6$) δ 10.65 (s, 1H), 8.21 (d, J=1.9 Hz, 1H), 7.92 (d, J=1.9 Hz, 1H), 3.30-3.26 (m, 4H), 2.93 (s, 2H), 2.12-2.04 (m, 4H), 1.92-1.82 (m, 2H), 1.46-1.38 (m, 2H).

Step-(iii): Synthesis of 6'-bromo-1'H-spiro[cyclohexane-1,3'-[1,8]naphthyridine]-2',4(4'H)-dione (P)

To a stirred solution of ethyl 1,4-dithiaspiro[4.5]decane-8-carboxylate (O) (0.85 g, 2.21 mmol) in acetonitrile/water (15 mL/5 mL) was added ceric ammonium nitrite (9.7 g, 17.68 mmol) at 0° C. and the reaction mixture was allowed to stir at 20-35° C. for 2 h. Then the reaction mixture was diluted with ethyl acetate (50 mL) and washed with $NaHCO_3$ solution (50 mL). The organic layer was washed with water (30 mL), brine (30 mL), dried over anhydrous $Na_2SO_4$ and filtered. The filtrate was rotary evaporated under vacuum to get residue which was purified by column chromatography using mixture of 40% ethyl acetate/hexane as an eluent to get the desired compound as an off-white solid (0.35 g, 51%); $^1$H NMR (400 MHz, DMSO-d$_6$) δ 10.78 (s, 1H), 8.25 (d, J=2.5 Hz, 1H), 7.88 (d, J=2.0 Hz, 1H), 3.07 (s, 2H), 2.42-2.32 (m, 4H), 2.08-1.96 (m, 2H), 1.74-1.64 (m, 2H).

Step-(iv): Synthesis of 6'-bromo-4-(hydroxyimino)-1'H-spiro[cyclohexane-1,3'-[1,8]naphthyridin]-2'(4'H)-one (Q)

To a stirred solution of 6'-bromo-1'H-spiro[cyclohexane-1,3'-[1,8]naphthyridine]-2',4(4'H)-dione (P) (0.35 g, 1.13 mmol) in ethanol/water (18 mL/2 mL) were added Na$_2$CO$_3$ (0.6 g, 5.68 mmol) and hydroxylamine hydrochloride (0.39 g, 5.68 mmol) at 20-35° C. and the reaction mixture was allowed to stir at 20-35° C. for 4 h. Then the reaction mixture was diluted with water (50 mL) and extracted with ethyl acetate (2×50 mL). The organic layer was washed with water (50 mL), brine (50 mL), dried over anhydrous Na$_2$SO$_4$ and filtered. The filtrate was rotary evaporated under vacuum to get the desired compound as an off-white solid (200 mg, 95%); $^1$H NMR (400 MHz, DMSO-d$_6$) δ 10.69 (s, 1H), 10.28 (s, 1H), 8.23 (d, J=2.4 Hz, 1H), 7.88 (d, J=2.0 Hz, 1H), 2.99 (s, 2H), 2.30-2.16 (m, 4H), 1.84-1.66 (m, 2H), 1.50-1.38 (m, 2H).

Step-(v): Synthesis of 6'-bromo-1'H-spiro[azepane-4,3'-[1,8]naphthyridine]-2',7(4'H)-dione (Intermediate-18)

To a stirred solution of 6'-bromo-4-(hydroxyimino)-1'H-spiro[cyclohexane-1,3'-[1,8]naphthyridin]-2'(4'H)-one (O) (200 mg, 0.62 mmol) in DCM (10 mL) were added triethylamine (0.26 mL, 1.86 mmol), followed by PTS-Cl (0.35 g, 1.86 mmol) at 0° C. and the reaction mixture was allowed to stir at 20-35° C. for 4 h. Then the reaction mixture was rotary evaporated under vacuum to get residue which was purified by column chromatography using mixture of 10% methanol/dichloromethane as an eluent to get the desired compound as a white solid (180 mg, 90%); LC-MS: 324.1 (M+1)$^+$.

Step-(vi): Synthesis of 6'-bromo-1'-((2-(trimethylsilylethoxy)methyl)-1'H-spiro[azepane-4,3'-[1,8]naphthyridine]-2',7(4'H)-dione To a stirred solution of 6'-bromo-1'H-spiro[azepane-4,3'-[1,8]naphthyridine]-2',7(4'H)-dione (Intermediate-18) (2 g, 6.20 mmol) in DMF (15 mL) were added 60% NaH (270 mg, 6.81 mmol) and SEM-Cl (1.1 g, 6.81 mmol) at 20-35° C. and the reaction mixture was allowed to stir at 20-35° C. for 2 h. Then the reaction mixture was diluted with water (50 mL), obtained solid was filtered, dried and crude was taken forward for next step.

Step-(vii): Synthesis of 6'-bromo-1-methyl-1'-((2-(trimethylsilylethoxy)methyl)-1'H-spiro[azepane-4,3'-[1,8]naphthyridine]-2',7(4'H)-dione To a stirred solution of compound obtained from step-vi (2 g, 4.40 mmol) in THF (20 mL) were added potassium tert-butoxide (1.23 g, 6.60 mmol) and dimethyl sulphate (1.27 g, 5.70 mmol) at 20-35° C. and the reaction mixture was allowed to stir at 20-35° C. for 16 h. Then the reaction mixture was diluted with water (50 mL) and extracted with ethyl acetate (2×50 mL). The organic layer was washed with brine (50 mL), dried over anhydrous Na$_2$SO$_4$ and filtered. The filtrate was rotary evaporated to get residue which was purified by column chromatography using a mixture of 2% methanol/dichloromethane as an eluent to get the desired mixture of compounds.

Step-(viii): Synthesis of 6'-bromo-1-methyl-1'H-spiro[azepane-4,3'-[1,8]naphthyridine]-2',7(4'H)-dione (Intermediate-19)

To a stirred solution of mixture of compounds obtained from step-vii (1.5 g, 3.20 mmol) in DCM (10 mL) was added trifluoroaceticacid (8 mL) and the reaction mixture was allowed to stir at 20-35° C. for 3 h. Then the reaction mixture was rotary evaporated under vacuum to get residue which was diluted with DCM (20 mL) and treated with ethylene diamine (8 mL) at 20-35° C. for 1 h. The reaction mixture was diluted with NaHCO$_3$ solution (50 mL) and extracted with dichloromethane (2×50 mL). The organic layer was washed with brine (50 mL), dried over anhydrous Na$_2$SO$_4$ and filtered to get the desired compound as an off-white solid (650 mg, 65%). LC-MS: 338.0 (M+1)$^+$.

Intermediate-20: Synthesis of 7'-bromo-4',5'-dihydrospiro[cyclopropane-1,3'-pyrido[2,3-e][1,4]diazepin]-2'(1'H)-one

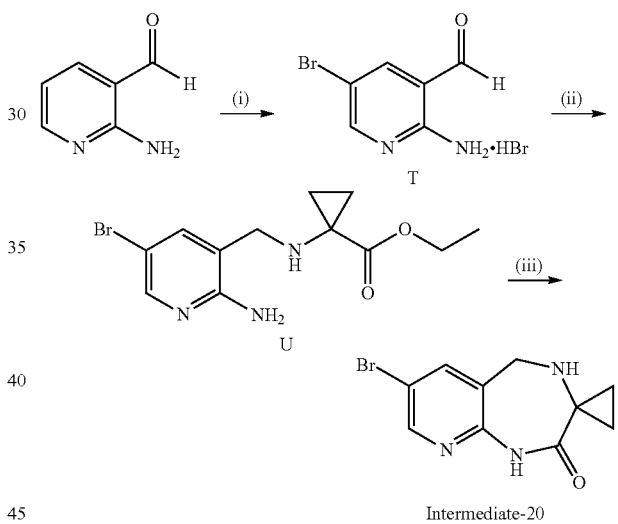

Intermediate-20

(Ref. for Step-(i): WO2004052890)

Step-(ii): Synthesis of ethyl 1-4(2-amino-5-bromopyridin-3-yl)methyl)amino)cyclopropane carboxylate (U)

To a stirred solution of ethyl-1-aminocyclopropanecarboxylate hydrochloride (9.77 g, 59.21 mmol) in methanol (100 mL) were added triethylamine (15.46 mL, 111.18 mmol) and 2-amino-5-bromonicotinaldehyde hydrobromide (T) (10.3 g, 36.78 mmol) at 0° C. and the reaction mixture was allowed to stir at 20-35° C. for 16 h. Then sodium cyanoborohydride (7 g, 111.39 mmol) was added at 0° C. and the reaction mixture was allowed to stir at 20-35° C. for another 16 h. The reaction mixture was rotary evaporated under vacuum and the resultant residue was diluted with water (200 mL) and extracted with ethyl acetate (2×200 mL). The organic layer was washed with brine (100 mL), dried over anhydrous Na$_2$SO$_4$ and filtered. The filtrate was rotary evaporated under vacuum to get residue which was purified by column chromatography using mixture of 4% methanol/ dichloromethane as an eluent to get the desired compound as a brown waxy solid (5.6 g, 48%); $^1$H NMR (400 MHz, DMSO-d$_6$) δ 7.89 (d, J=2.4 Hz, 1H), 7.44 (d, J=2.0 Hz, 1H), 6.16 (bs, 2H), 4.13-4.03 (m, 2H), 3.59 (d, J=4.4 Hz, 2H), 2.92-2.84 (m, 1H), 1.24-1.14 (m, 5H), 1.04-0.98 (m, 2H); LC-MS: 314.3 (M+1)$^+$.

Step-(iii): Synthesis of 7'-bromo-4',5'-dihydrospiro[cyclopropane-1,3'-pyrido[2,3-e][1,4]diazepin]-2'(1'H)-one (Intermediate-20)

To a stirred solution of ethyl 1-4(2-amino-5-bromopyridin-3-yl)methyl)amino)cyclo-propane carboxylate (U) (0.81 g, 2.59 mmol) in DMSO (3 mL) was added NaH (123 mg, 3.10 mmol) at 0° C. and the reaction mixture was allowed to stir at 20-35° C. for 3 h. The reaction mixture was quenched with ice water (50 mL), obtained solid was filtered, washed with water and dried under vacuum to get the desired compound as an off-white solid (0.47 g, 68%); $^1$H NMR (400 MHz, DMSO-d$_6$) δ 9.95 (s, 1H), 8.23 (d, J=2.0 Hz, 1H), 7.78 (d, J=2.5 Hz, 1H), 3.85 (d, J=6.3 Hz, 2H), 3.51 (t, J=6.4 Hz, 1H), 1.28 (dd, J=3.4 Hz, 6.9 Hz, 2H), 0.89 (dd, J=3.4, 6.9 Hz, 2H).

Intermediate-21: Synthesis of (S,E)-3-(10-oxo-7,8,9,9a,10,11-hexahydro-5H-pyrido[2,3-e]pyrrolo[1,2-a][1,4]diazepin-3-yl)acrylic acid

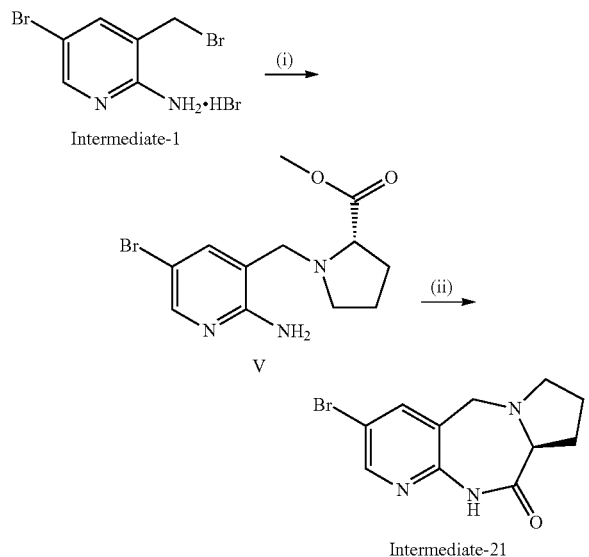

(Ref. for step-(i-ii): WO2004/052890).

Intermediate-22: Synthesis of (E)-3-(6,6-dimethyl-7-oxo-5,6,7,8-tetrahydro-1,8-naphthyridin-3-yl)acrylic acid

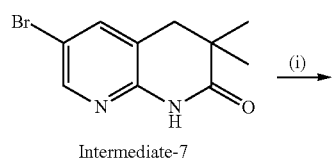

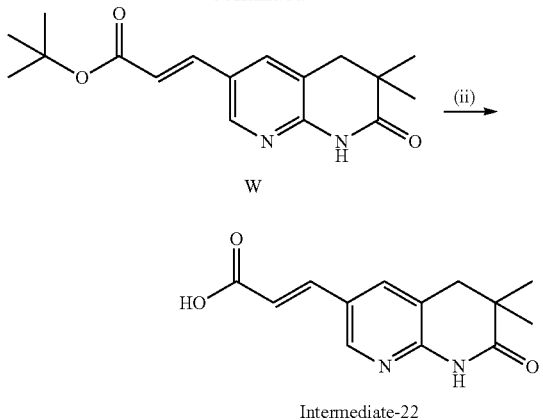

Step-(i): Synthesis of (E)-tert-butyl 3-(6,6-dimethyl-7-oxo-5,6,7,8-tetrahydro-1,8-naphthyridin-3-yl)acrylate (W)

To a stirred solution of 6-bromo-3,3-dimethyl-3,4-dihydro-1,8-naphthyridin-2(1H)-one (Intermediate-7) (1.3 g, 5.10 mmol), tert-butyl acrylate (3.26 g, 25.50 mmol) in DMF/propionitrile (5 mL/20 mL) was added DIPEA (2.7 mL, 15.30 mmol) at 20-35° C. and the mixture was degassed with N$_2$ for 10 minutes. Then Pd(OAc)$_2$ (114 mg, 0.51 mmol), P(o-tolyl)$_3$ (310 mg, 1.02 mmol) were added, again degassed with N$_2$ for another 10 minutes and heated at 125° C. for 16 h. The reaction mixture was cooled to 20-35° C. and filtered through Celite®. The filtrate was rotary evaporated under vacuum to get residue which was purified by column chromatography using a mixture of 80% ethyl acetate/hexane as an eluent to get the desired compound as a pale yellow solid (1.2 g, 78%); $^1$H NMR (400 MHz, DMSO-d$_6$) δ 10.66 (s, 1H), 8.37 (d, J=2.0 Hz, 1H), 8.02 (d, J=1.0 Hz, 1H), 7.50 (d, J=15.6 Hz, 1H), 6.51 (d, J=16.1 Hz, 1H), 2.78 (s, 2H), 1.48 (s, 9H), 1.07 (s, 6H).

Step-(ii): Synthesis of (E)-3-(6,6-dimethyl-7-oxo-5,6,7,8-tetrahydro-1,8-naphthyridin-3-yl) acrylic acid (Intermediate-22)

To a stirred solution of (E)-tert-butyl 3-(6,6-dimethyl-7-oxo-5,6,7,8-tetrahydro-1,8-naphthyridin-3-yl)acrylate (W) (1.2 g, 3.97 mmol) in CH$_2$Cl$_2$ (10 mL) was added trifluoro acetic aid (5 mL) at 20-35° C. and the reaction mixture was allowed to stir at 20-35° C. for 3 h. Then the reaction mixture was rotary evaporated under vacuum to get residue which was triturated with diethyl ether to get the desired compound as an off-white solid (700 mg, 77%); $^1$H NMR (400 MHz, DMSO-d$_6$) δ 10.66 (s, 1H), 8.37 (d, J=2.0 Hz, 1H), 8.01 (s, 1H), 7.55 (d, J=16.1 Hz, 1H), 6.51 (d, J=15.6 Hz, 1H), 2.80 (s, 2H), 1.08 (s, 6H).

The below Intermediates-23 to 28 were prepared according to the above protocol (Intermediate-22) by using appropriate starting compounds and reagents at suitable conditions. The physiochemical characterization of the intermediates are given below.

| Int No. | Structure | Characterization data ($^1$H NMR (400 MHz, DMSO-$d_6$)/LC-MS/ES-MS) |
| --- | --- | --- |
| 23 | 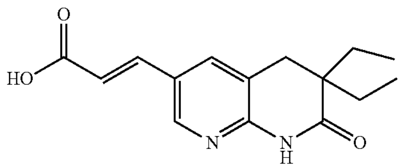 [SMILES: CCC1(CC)Cc2cc(/C=C/C(=O)O)cnc2NC1=O] | δ 10.65 (s, 1H), 8.35 (d, J = 2.0 Hz, 1H), 8.03 (s, 1H), 7.54 (d, J = 16.1 Hz, 1H), 6.49 (d, J = 16.2 Hz, 1H), 2.82 (s, 2H), 1.54-1.38 (m, 4H), 0.80 (t, J = 7.3 Hz, 6H). |
| 24 | 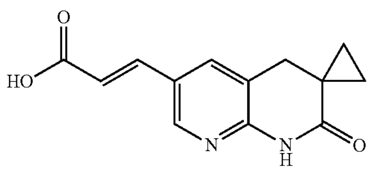 [SMILES: O=C(O)/C=C/c1cnc2c(c1)CC1(CC1)C(=O)N2] | δ 10.76 (s, 1H), 8.38 (d, J = 1.4 Hz, 1H), 7.94 (s, 1H), 7.55 (d, J = 16.1 Hz, 1H), 6.49 (d, J = 15.7 Hz, 1H), 2.88 (s, 2H), 1.14-1.09 (m, 2H), 0.81-0.77 (m, 2H). |
| 25 | 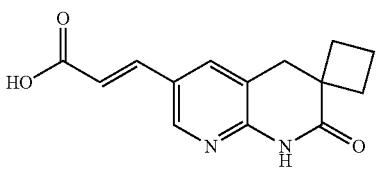 [SMILES: O=C(O)/C=C/c1cnc2c(c1)CC1(CCC1)C(=O)N2] | δ 10.63 (s, 1H), 8.35 (d, J = 2.4 Hz, 1H), 8.05 (d, J = 1.5 Hz, 1H), 7.54 (d, J = 16.1 Hz, 1H), 6.50 (d, J = 16.1 Hz, 1H), 3.06 (s, 2H), 2.34 (dd, J = 9.3, 18.6 Hz, 2H), 2.06-1.92 (m, 1H), 1.91-1.84 (m, 1H), 1.82-1.72 (m, 2H). |
| 26 | <br>* mixture of isomers | ES-MS: 330.2 (M + 1)$^+$. |
| 27 | 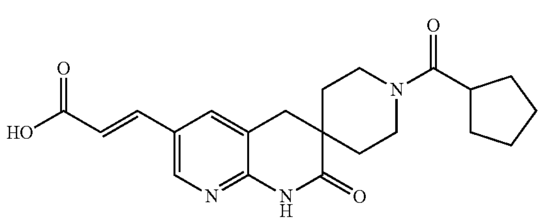 [SMILES: O=C(O)/C=C/c1cnc2c(c1)CC1(CCN(C(=O)C3CCCC3)CC1)C(=O)N2] | LC-MS: 383.3 (M + 1)$^+$. |
| 28 | 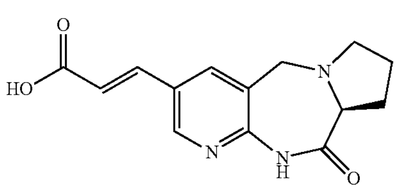 [SMILES: O=C(O)/C=C/c1cnc2c(c1)CN1CCC[C@H]1C(=O)N2] | δ 12.46 (brs, 1H), 11.30 (s, 1H), 8.78 (s, 1H), 8.23 (s, 1H), 7.65 (d, J = 16.1 Hz, 1H), 6.62 (d, J = 16.2 Hz, 1H), 4.27 (d, J = 13.2 Hz, 1H), 4.13 (d, J = 13.2 Hz, 1H), 3.68-3.58 (m, 1H), 3.34-3.22 (m, 1H), 3.20-3.10 (m, 1H), 2.36-2.26 (m, 1H), 1.98-1.86 (m, 2H), 1.84-1.72 (m, 1H). |

Example-I

Synthesis of (E)-tert-butyl 2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxylate (Compound 1)

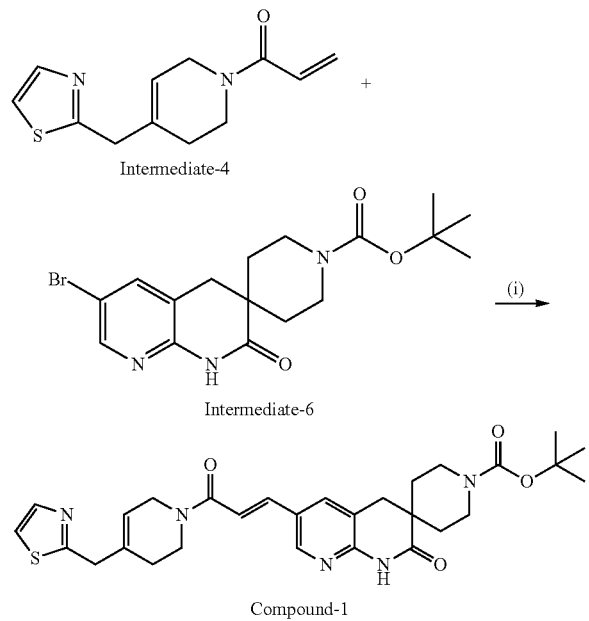

To a stirred solution of 1-(4-(thiazol-2-ylmethyl)-5,6-dihydropyridin-1(2H)-yl)prop-2-en-1-one (Intermediate-4) (350 mg, 1.50 mmol) and tert-butyl 6-bromo-2-oxo-2,4-dihydro-1H-spiro[[1,8]naphthyridine-3,4'-piperidine]-1'-carboxylate (Intermediate-6) (500 mg, 1.20 mmol) in DMF/propionitrile (4 mL/16 mL) was added DIPEA (0.55 mL, 3.16 mmol) at 20-35° C. and the mixture was degassed with $N_2$ for 10 minutes. Then $Pd(OAc)_2$ (28 mg, 0.12 mmol) and $P(o-tolyl)_3$ (77 mg, 0.25 mmol) were added, again degassed with $N_2$ for another 10 minutes and heated at 110° C. for 16 h. The reaction mixture was cooled to 20-35° C. and filtered through Celite®. The filtrate was rotary evaporated under vacuum to get residue which was purified by column chromatography using mixture of 3% MeOH/DCM as an eluent to get the desired compound as a light yellow solid (150 mg, 22%); $^1$H NMR (400 MHz, DMSO-$d_6$) δ 10.73 (s, 1H), 8.37 (d, J=1.5 Hz, 1H), 8.09 (s, 1H), 7.71 (d, J=3.4 Hz, 1H), 7.61 (d, J=3.5 Hz, 1H), 7.45 (d, J=15.1 Hz, 1H), 7.28-7.16 (m, 1H), 5.68-5.64 (m, 1H), 4.24-4.21 (m, 1H), 4.08-4.03 (m, 1H), 3.75 (s, 2H), 3.64-3.61 (m, 1H), 3.57-3.52 (m, 3H), 3.27-3.21 (m, 2H), 2.94 (s, 2H), 2.18-2.13 (m, 2H), 1.80-1.68 (m, 2H), 1.39 (s, 9H), 1.40-1.31 (m, 2H); ES-MS: 548.2 (M−1)$^+$.

The below compounds were prepared by procedure similar to the one described in Example-I with appropriate variations in reactants, quantities of reagents at suitable reaction conditions. The physicochemical characteristics of the compounds are summarized herein below table.

| Comp. No | Compound structure | Characterization data ($^1$H NMR (400 MHz, DMSO-$d_6$) in δ (ppm)/LC-MS or ES-MS |
|---|---|---|
| 2 | 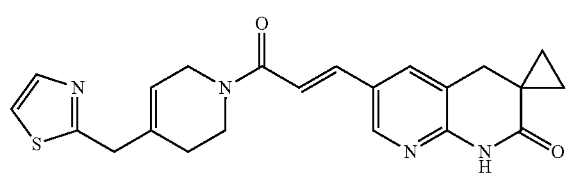 [SMILES: O=C(/C=C/c1cnc2c(c1)CC1(CC1)C(=O)N2)N1CC=C(Cc2nccs2)CC1] | δ 10.71 (s, 1H), 8.38 (s, 1H), 8.01 (s, 1H), 7.71 (d, J = 3.5 Hz, 1H), 7.60 (d, J = 2.9 Hz, 1H), 7.46 (d, J = 15.7 Hz, 1H), 7.27-7.19 (m, 1H), 5.68-5.65 (m, 1H), 4.28-4.22 (m, 1H), 4.08-4.02 (m, 1H), 3.78-3.72 (m, 3H), 3.68-3.62 (m, 1H), 2.87 (s, 2H), 2.18-2.06 (m, 2H), 1.14-1.10 (m, 2H), 0.80-0.77 (m, 2H); LC-MS: 407.1 (M + 1)$^+$. |
| 3 | 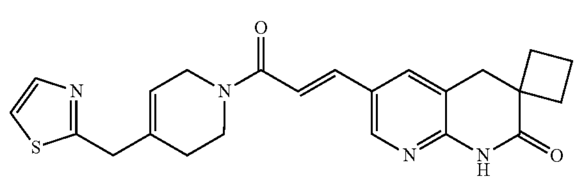 [SMILES: O=C(/C=C/c1cnc2c(c1)CC1(CCC1)C(=O)N2)N1CC=C(Cc2nccs2)CC1] | δ 10.58 (s, 1H), 8.34 (s, 1H), 8.12 (s, 1H), 7.71 (d, J = 3.4 Hz, 1H), 7.61 (d, J = 3.5 Hz, 1H), 7.45 (d, J = 15.1 Hz, 1H), 7.30-7.14 (m, 1H), 5.68-5.63 (m, 1H), 4.28-4.20 (m, 1H) 4.08-4.01 (m, 1H), 3.78-3.72 (m, 3H), 3.68-3.61 (m, 1H), 3.06 (s, 2H), 2.42-2.30 (m, 2H), 2.20-2.06 (m, 2H), 2.04-1.96 (m, 1H), 1.93-1.84 (m, 1H), 1.82-1.72 (m, 2H); LC-MS: 421.2 (M + 1)$^+$. |
| 4 | 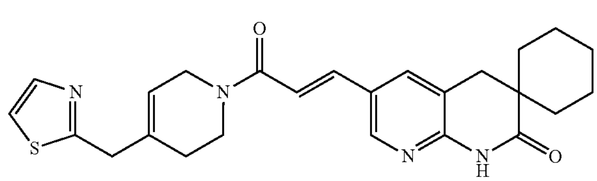 [SMILES: O=C(/C=C/c1cnc2c(c1)CC1(CCCCC1)C(=O)N2)N1CC=C(Cc2nccs2)CC1] | δ 10.58 (s, 1H), 8.33 (s, 1H), 8.13 (s, 1H), 7.71 (d, J = 3.4 Hz, 1H), 7.61 (d, J = 3.5 Hz, 1H), 7.45 (d, J = 15.6 Hz, 1H), 7.28-7.16 (m, 1H), 5.68-5.65 (m, 1H), 4.28-4.20 (m, 1H), 4.08-4.02 (m, 1H), 3.78-3.72 (m, 3H), 3.68-3.62 (m, 1H), 2.90 (s, 2H), 2.18-2.06 (m, 2H), 1.72-1.56 (m, 4H), 1.55-1.43 (m, 2H), 1.38-1.22 (m, 4H); ES-MS: 449.3 (M + 1)$^+$. |

-continued

| Comp. No | Compound structure | Characterization data (¹H NMR (400 MHz, DMSO-d$_6$) in δ (ppm)/LC-MS or ES-MS |
|---|---|---|
| 5 | 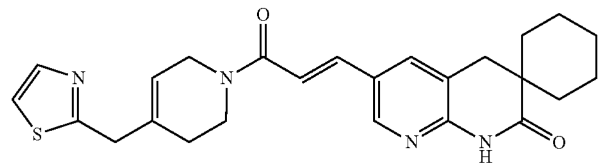 [SMILES: O=C(/C=C/c1cnc2c(c1)CC1(CCCCC1)C(=O)N2)N1CC=C(Cc2nccs2)CC1] | δ 10.58 (s, 1H), 8.33 (s, 1H), 8.13 (s, 1H), 7.44 (d, J = 15.2 Hz, 1H), 7.35 (d, J = 4.9 Hz, 1H), 7.28-7.14 (m, 1H), 6.98-6.94 (m, 1H), 6.90-6.86 (m, 1H), 5.64-5.56 (m, 1H), 4.28-4.18 (m, 1H), 4.08-4.00 (m, 1H), 3.80-3.70 (m, 1H), 3.68-3.58 (m, 1H), 3.55 (s, 2H), 2.90 (s, 2H), 2.18-2.02 (m, 2H), 1.72-1.52 (m, 4H), 1.51-1.36 (m, 2H), 1.35-1.22 (m, 4H); ES-MS: 448.3 (M + 1)⁺. |
| 6 | 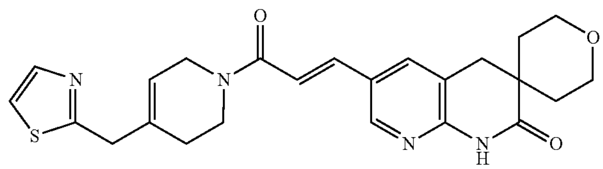 [SMILES: O=C(/C=C/c1cnc2c(c1)CC1(CCOCC1)C(=O)N2)N1CC=C(Cc2nccs2)CC1] | δ 10.71 (s, 1H), 8.36 (s, 1H), 8.12 (s, 1H), 7.71 (d, J = 2.9 Hz, 1H), 7.61 (d, J = 3.0 Hz, 1H), 7.45 (d, J = 15.6 Hz, 1H), 7.28-7.16 (m, 1H), 5.68-5.63 (m, 1H), 4.28-4.22 (m, 1H), 4.08-4.02 (m, 1H), 3.80-3.62 (m, 4H), 3.60-3.54 (m, 2H), 2.98 (s, 2H), 2.18-2.05 (m, 2H), 1.86-1.74 (m, 2H), 1.38-1.22 (m, 4H); ES-MS: 449.5 (M − 1)⁺. |
| 7 | 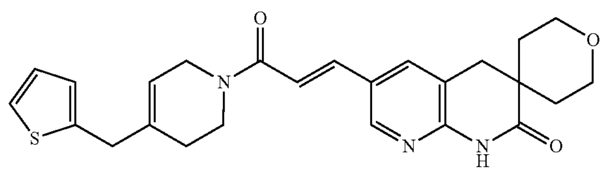 [SMILES: O=C(/C=C/c1cnc2c(c1)CC1(CCOCC1)C(=O)N2)N1CC=C(Cc2cccs2)CC1] | δ 10.70 (s, 1H), 8.36 (d, J = 2.0 Hz, 1H), 8.12 (s, 1H), 7.45 (d, J = 15.2 Hz, 1H), 7.37-7.34 (m, 1H), 7.28-7.14 (m, 1H), 6.96 (dd, J = 3.4, 5.4 Hz, 1H), 6.87 (d, J = 2.9 Hz, 1H), 5.62-5.56 (m, 1H), 4.28-4.20 (m, 1H), 4.08-4.02 (m, 1H), 3.78-3.68 (m, 3H), 3.66-3.56 (m, 3H), 3.55 (s, 2H), 2.98 (s, 2H), 2.16-2.00 (m, 2H), 1.88-1.76 (m, 2H), 1.36-1.28 (m, 2H); ES-MS: 450.2 (M + 1)⁺. |
| 8 | 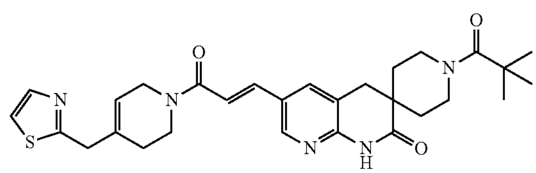 [SMILES: CC(C)(C)C(=O)N1CCC2(CC1)Cc1cc(/C=C/C(=O)N3CC=C(Cc4nccs4)CC3)cnc1NC2=O] | δ 10.75 (s, 1H), 8.38 (d, J = 2.0 Hz, 1H), 8.08 (s, 1H), 7.71 (d, J = 3.4 Hz, 1H), 7.61 (d, J = 3.0 Hz, 1H), 7.45 (d, J = 15.7 Hz, 1H), 7.27-7.14 (m, 1H), 5.69-5.66 (m, 1H), 4.28-4.22 (m, 1H), 4.08-4.02 (m, 1H), 3.82-3.70 (m, 5H), 3.68-3.60 (m, 1H), 3.48 (t, J = 9.8 Hz, 2H), 2.97 (s, 2H), 2.20-2.04 (m, 2H), 1.75 (t, J = 9.3 Hz, 2H), 1.42-1.32 (m, 2H), 1.18 (s, 9H); ES-MS: 534.2 (M + 1)⁺. |
| 9 | 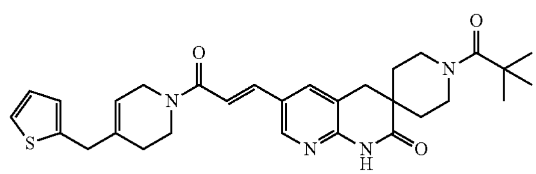 [SMILES: CC(C)(C)C(=O)N1CCC2(CC1)Cc1cc(/C=C/C(=O)N3CC=C(Cc4cccs4)CC3)cnc1NC2=O] | δ 10.75 (s, 1H), 8.37 (d, J = 1.9 Hz, 1H), 8.08 (s, 1H), 7.45 (d, J = 15.6 Hz, 1H), 7.35 (dd, J = 1.0 Hz, 5.4 Hz, 1H), 7.28-7.14 (m, 1H), 6.96 (dd, J = 3.4, 4.9 Hz, 1H), 6.87 (d, J = 2.5 Hz, 1H), 5.60-5.57 (m, 1H), 4.26-4.18 (m, 1H), 4.08-4.01 (m, 1H), 3.82-3.72 (m, 3H), 3.70-3.58 (m, 1H), 3.54 (s, 2H), 3.52-3.42 (m, 2H), 2.96 (s, 2H), 2.14-1.94 (m, 2H), 1.80-1.68 (m, 2H), 1.42-1.28 (m, 2H), 1.18 (s, 9H); ES-MS: 533.2 (M + 1)⁺. |
| 10 | 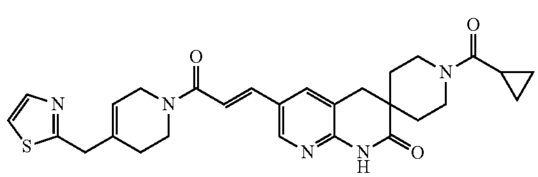 | δ 10.76 (s, 1H), 8.39 (s, 1H), 8.10 (s, 1H), 7.71 (d, J = 3.4 Hz, 1H), 7.61 (d, J = 3.0 Hz, 1H), 7.46 (d, J = 15.6 Hz, 1H), 7.28-7.16 (m, 1H), 5.68-5.65(m, 1H), 4.28-4.20 (m, 1H), 4.08-4.00 (m, 1H), 3.94-3.84 (m, 1H), 3.80-3.68 (m, 4H), 3.67-3.60 (m, 2H), 3.46-3.34 (m, 1H), 2.98 (s, 2H), 2.20-2.06 (m, 2H), 2.04-1.92 (m, 1H), 1.90-1.82 (m, 1H), 1.74-1.66 (m, 1H), 1.46-1.36 (m, 2H), 0.74-0.66 (m, 4H); ES-MS: 518.3 (M + 1)⁺. |
| 11 | 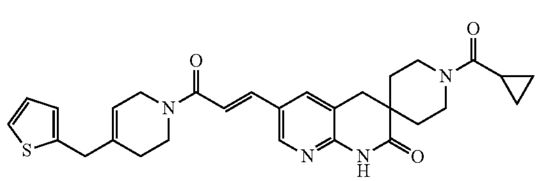 [SMILES: O=C(/C=C/c1cnc2c(c1)CC1(CCN(C(=O)C3CC3)CC1)C(=O)N2)N1CC=C(Cc2cccs2)CC1] | δ 10.75 (s, 1H), 8.38 (s, 1H), 8.09 (s, 1H), 7.45 (d, J = 15.2 Hz, 1H), 7.40-7.34 (m, 1H), 7.32-7.10 (m, 1H), 7.00-6.94 (m, 1H), 6.92-6.84 (m, 1H), 5.60-5.57 (m, 1H), 4.26-4.16 (m, 1H), 4.08-4.00 (m, 1H), 3.96-3.83 (m, 2H), 3.82-3.72 (m, 2H), 3.70-3.60 (m, 2H), 3.55 (s, 2H), 2.98 (s, 2H), 2.18-1.92 (m, 3H), 1.90-1.78 (m, 1H), 1.76-1.62 (m, 2H), 1.50-1.26 (m, 2H), 0.78-0.62 (m, 4H); ES-MS: 517.3 (M + 1)⁺. |
| 12 | 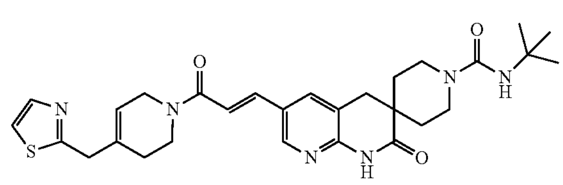 [SMILES: CC(C)(C)NC(=O)N1CCC2(CC1)Cc1cc(/C=C/C(=O)N3CC=C(Cc4nccs4)CC3)cnc1NC2=O] | δ 10.70 (s, 1H), 8.37 (d, J = 2.0 Hz, 1H), 8.11 (s, 1H), 7.71 (d, J = 2.9 Hz, 1H), 7.61 (d, J = 3.5 Hz, 1H), 7.45 (d, J = 15.2 Hz, 1H), 7.26-7.16 (m, 1H), 5.73 (s, 1H), 5.70-5.67 (s, 1H), 4.26-4.20 (m, 1H), 4.08-4.02 (m, 1H), 3.78-3.72 (m, 3H), 3.66-3.62 (m, 1H), 3.56-3.48 (m, 2H), 3.20-3.10 (m, 2H), 2.93 (s, 2H), 2.18-2.06 (m, 2H), 1.76-1.66 (m, 2H), 1.34-1.25 (m, 2H), 1.24 (s, 9H); ES-MS: 547.5 (M − 1)⁺. |

| Comp. No | Compound structure | Characterization data (¹H NMR (400 MHz, DMSO-d$_6$) in δ (ppm)/LC-MS or ES-MS |
|---|---|---|
| 13 | 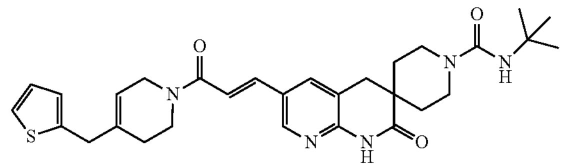 [SMILES: CC(C)(C)NC(=O)N1CCC2(CC1)Cc1cc(/C=C/C(=O)N3CC=C(Cc4cccs4)CC3)cnc1NC2=O] | δ 10.69 (s, 1H), 8.36 (d, J = 1.9 Hz, 1H), 8.10 (s, 1H), 7.45 (d, J = 15.2 Hz, 1H), 7.35 (dd, J = 1.0, 5.4 Hz, 1H), 7.28-7.14 (m, 1H), 6.96 (dd, J = 3.5, 5.4 Hz, 1H), 6.88 (d, J = 2.4 Hz, 1H), 5.73 (s, 1H), 5.60-5.57 (s, 1H), 4.26-4.18 (m, 1H), 4.08-4.00 (m, 1H), 3.74-3.68 (m, 1H), 3.66-3.59 (m, 1H), 3.54 (s, 2H), 3.50-3.46 (m, 2H), 3.14 (t, J = 10.3 Hz, 2H), 2.93 (s, 2H), 2.14-2.00 (m, 2H), 1.79-1.64 (m, 2H), 1.34-1.25 (m, 2H), 1.24 (s, 9H); ES-MS: 548.3 (M + 1)⁺. |
| 14 | 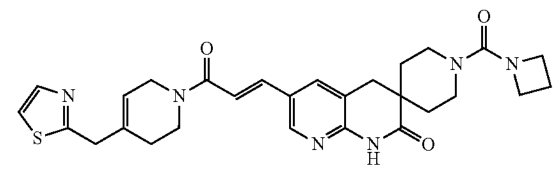 [SMILES: O=C(/C=C/c1cnc2c(c1)CC1(CCN(C(=O)N3CCC3)CC1)C(=O)N2)N1CC=C(Cc2nccs2)CC1] | δ 10.72 (s, 1H), 8.37 (d, J = 2.0 Hz, 1H), 8.09 (s, 1H), 7.71 (d, J = 3.4 Hz, 1H), 7.61 (d, J = 3.4 Hz, 1H), 7.45 (d, J = 15.6 Hz, 1H), 7.28-7.12 (m, 1H), 5.68-5.65 (m, 1H), 4.26-4.20 (m, 1H), 4.08-4.02 (m, 1H), 3.86 (t, J = 7.8 Hz, 4H), 3.80-3.70 (m, 3H), 3.70-3.60 (m, 1H), 3.46-3.36 (m, 2H), 3.22-3.10 (m, 2H), 2.94 (s, 2H), 2.20-2.04 (m, 4H), 1.76-1.68 (m, 2H), 1.32-1.28 (m, 2H); ES-MS: 531.3 (M − 1)⁺. |
| 15 | 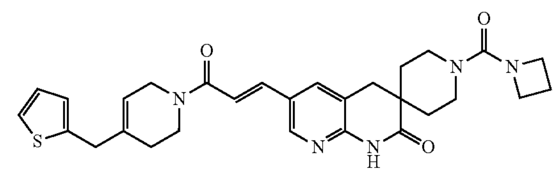 | δ 10.71 (s, 1H), 8.37 (d, J = 2.0 Hz, 1H), 8.09 (s, 1H), 7.45 (d, J = 15.7 Hz, 1H), 7.35 (dd, J = 1.0, 5.4 Hz, 1H), 7.28-7.14 (m, 1H), 6.96 (dd, J = 3.4, 4.9 Hz, 1H), 6.87 (d, J = 2.4 Hz, 1H), 5.60-5.57 (m, 1H), 4.26-4.18 (m, 1H), 4.08-4.03 (m, 1H), 3.86 (t, J = 7.9 Hz, 4H), 3.80-3.70 (m, 1H), 3.68-3.60 (m, 1H), 3.55 (s, 2H), 3.48-3.34 (m, 2H), 3.24-3.14 (m, 2H), 2.94 (s, 2H), 2.18-2.08 (m, 3H), 2.07-1.98 (m, 1H), 1.76-1.68 (m, 2H), 1.34-1.26 (m, 2H); ES-MS: 532.2 (M + 1)⁺. |
| 16 | 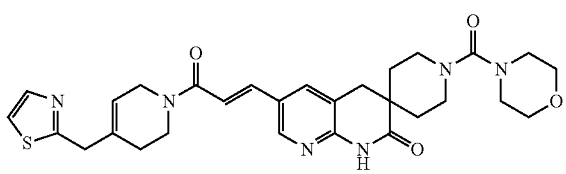 [SMILES: O=C(/C=C/c1cnc2c(c1)CC1(CCN(C(=O)N3CCOCC3)CC1)C(=O)N2)N1CC=C(Cc2nccs2)CC1] | δ 10.73 (s, 1H), 8.37 (s, 1H), 8.09 (s, 1H), 7.71 (d, J = 2.9 Hz, 1H), 7.61 (d, J = 3.0 Hz, 1H), 7.45 (d, J = 15.2 Hz, 1H), 7.28-7.14 (m, 1H), 5.68-5.64 (m, 1H), 4.28-4.20 (m, 1H), 4.08-4.00 (m, 1H), 3.80-3.68 (m, 3H), 3.66-3.58 (m, 1H), 3.57-3.48 (m, 4H), 3.26-3.14 (m, 4H), 3.13-3.06 (m, 4H), 2.95 (s, 2H), 2.20-2.04 (m, 2H), 1.84-1.74 (m, 2H), 1.40-1.28 (m, 2H); LC-MS: 563.3 (M + 1)⁺. |
| 17 | 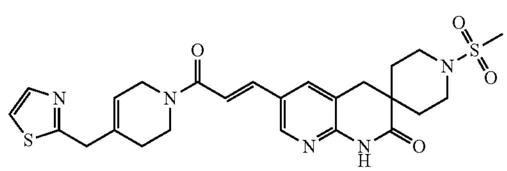 [SMILES: CS(=O)(=O)N1CCC2(CC1)Cc1cc(/C=C/C(=O)N3CC=C(Cc4nccs4)CC3)cnc1NC2=O] | δ 10.78 (s, 1H), 8.39 (s, 1H), 8.08 (s, 1H), 7.71 (d, J = 3.4 Hz, 1H), 7.61 (d, J = 3.5 Hz, 1H), 7.46 (d, J = 15.1 Hz, 1H), 7.28-7.14 (m, 1H), 5.68-5.65 (m, 1H), 4.28-4.22 (m, 1H), 4.08-4.02 (m, 1H), 3.78-3.72 (m, 3H), 3.66-3.62 (m, 1H), 3.36-3.26 (m, 2H), 3.16 (t, J = 8.1 Hz, 2H), 2.95 (s, 2H), 2.89 (s, 3H), 2.18-2.06 (m, 2H), 1.87 (t, J = 9.0 Hz, 2H), 1.52-1.46 (m, 2H); ES-MS: 528.2 (M + 1)⁺. |
| 18 | 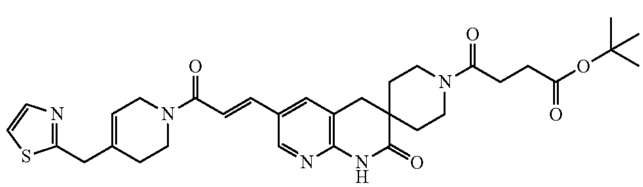 [SMILES: CC(C)(C)OC(=O)CCC(=O)N1CCC2(CC1)Cc1cc(/C=C/C(=O)N3CC=C(Cc4nccs4)CC3)cnc1NC2=O] | δ 10.75 (s, 1H), 8.38 (s, 1H), 8.10 (s, 1H), 7.71 (d, J = 3.4 Hz, 1H), 7.61 (d, J = 3.5 Hz, 1H), 7.46 (d, J = 15.2 Hz, 1H), 7.28-7.14 (m, 1H), 5.68-5.65 (m, 1H), 4.28-4.20 (s, 1H), 4.08-4.00 (m, 1H), 3.78-3.68 (m, 3H), 3.75 (s, 2H), 3.68-3.58 (m, 2H), 3.48-3.36 (m, 2H), 2.96 (s, 2H), 2.44-2.36 (m, 3H), 2.20-2.06 (m, 2H), 1.88-1.76 (m, 1H), 1.74-1.64 (m, 1H), 1.44-1.28 (m, 2H), 1.38 (s, 9H); ES-MS: 606.4 (M + 1)⁺. |
| 19 | 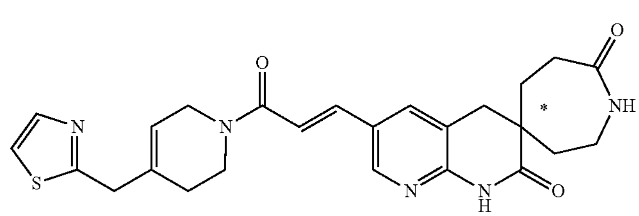 | ES-MS: 478.2 (M + 1)⁺. |

* mixture of isomers

| Comp. No | Compound structure | Characterization data ($^1$H NMR (400 MHz, DMSO-d$_6$) in δ (ppm)/LC-MS or ES-MS |
|---|---|---|
| 20 | *mixture of isomers | ES-MS: 477.4 (M + 1)$^+$. |
| 21 | 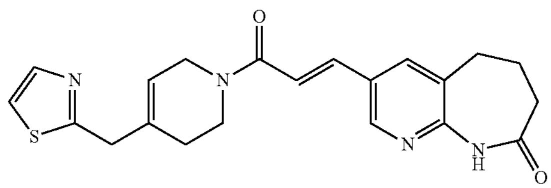 [SMILES: O=C1CCCc2cc(/C=C/C(=O)N3CC=C(Cc4nccs4)CC3)cnc2N1] | δ 10.05 (s, 1H), 8.49 (d, J = 2.5 Hz, 1H), 8.16 (s, 1H), 7.71 (d, J = 3.4 Hz, 1H), 7.61 (d, J = 3.5 Hz, 1H), 7.48 (d, J = 15.1 Hz, 1H), 7.36-7.24 (m, 1H), 5.68-5.65 (m, 1H), 4.26-4.22 (m, 1H), 4.08-4.04 (m, 1H), 3.80-3.73 (m, 3H), 3.66-3.62 (m, 1H), 2.71 (d, J = 7.4 Hz, 2H), 2.28-2.21 (m, 2H), 2.20-2.14 (m, 2H), 2.13-2.06 (m, 2H); ES-MS: 393.3(M − 1)$^+$. |
| 22 | 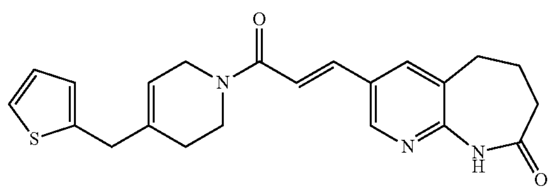 [SMILES: O=C1CCCc2cc(/C=C/C(=O)N3CC=C(Cc4cccs4)CC3)cnc2N1] | δ 10.05 (s, 1H), 8.49 (d, J = 1.9 Hz, 1H), 8.15 (s, 1H), 7.48 (d, J = 15.1 Hz, 1H), 7.35 (dd, J = 5.4, 1.5 Hz, 1H), 7.32-7.24 (m, 1H), 6.96 (dd, J = 5.4, 3.4 Hz, 1H), 6.88-6.84 (m, 1H), 5.60-5.56 (m, 1H), 4.28-4.20 (m, 1H), 4.08-4.02 (m, 1H), 3.78-3.73 (m, 1H), 3.68-3.62 (m, 1H), 3.55 (s, 2H), 2.71 (t, J = 7.4 Hz, 2H), 2.28-2.20 (m, 2H), 2.18-2.06 (m, 3H), 2.05-1.98 (m, 1H); ES-MS: 394.2 (M + 1)$^+$. |
| 23 | 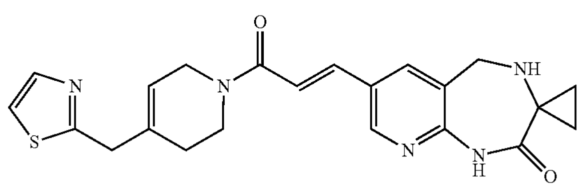 [SMILES: O=C(/C=C/c1cnc2c(c1)CNC1(CC1)C(=O)N2)N1CC=C(Cc2nccs2)CC1] | δ 9.95 (s, 1H), 8.39 (d, J = 2.0 Hz, 1H), 7.99 (s, 1H), 7.71 (d, J = 3.5 Hz, 1H), 7.61 (d, J = 3.4 Hz, 1H), 7.46 (d, J = 15.1 Hz, 1H), 7.30-7.16 (m, 1H), 5.68-5.65 (m, 1H), 4.28-4.22 (m, 1H), 4.10-4.02 (m, 1H), 3.89 (d, J = 5.9 Hz, 2H), 3.78-3.72 (m, 3H), 3.68-3.60 (m, 1H), 3.56-3.48 (m, 1H), 2.20-2.04 (m, 2H), 1.30 (dd, J = 3.5 Hz, 7.4 Hz, 2H), 0.92 (t, J = 3.5 Hz, 2H); LC-MS: 422.2 (M + 1)$^+$. |
| 24 | 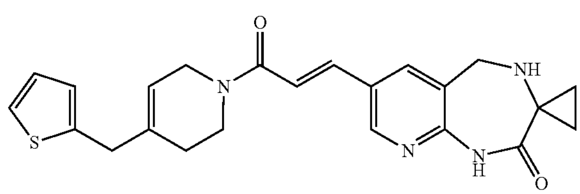 [SMILES: O=C(/C=C/c1cnc2c(c1)CNC1(CC1)C(=O)N2)N1CC=C(Cc2cccs2)CC1] | δ 9.95 (s, 1H), 8.39 (d, J = 1.5 Hz, 1H), 7.99 (s, 1H), 7.45 (d, J = 15.7 Hz, 1H), 7.35 (dd, J = 1.0, 4.9 Hz, 1H), 7.30-7.16 (m, 1H), 6.96 (dd, J = 3.4, 5.3 Hz, 1H), 6.87 (d, J = 2.5 Hz, 1H), 5.62-5.58 (m, 1H), 4.26-4.18 (m, 1H), 4.06-4.00 (m, 1H), 3.89 (d, J = 6.4 Hz, 2H), 3.78-3.72 (m, 1H), 3.68-3.60 (m, 1H), 3.58-3.48 (m, 1H), 3.54 (s, 2H), 2.12-1.97 (m, 2H), 1.30 (q, J = 3.4, 6.9 Hz, 2H), 0.92 (q, J = 3.4, 6.9 Hz, 2H); LC-MS: 421.2 (M + 1)$^+$. |

Example-II

Synthesis of (E)-3,3-dimethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one (Compound 25)

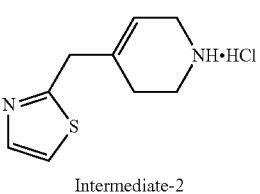

Intermediate-2

+

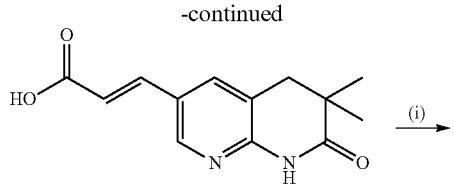

Intermediate-22

(i)

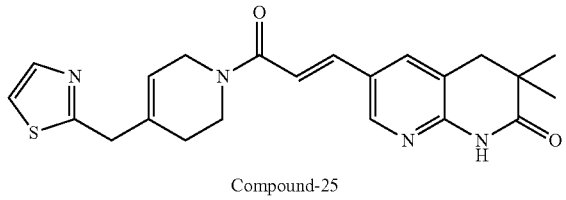

Compound-25

DIPEA (0.33 mL, 1.83 mmol) was added to a stirred solution of 2-((1,2,3,6-tetrahydro-pyridin-4-yl)methyl)thiazole hydrochloride (Intermediate-2) (158 mg, 0.73 mmol), (E)-3-(6,6-dimethyl-7-oxo-5,6,7,8-tetrahydro-1,8-naphthyridin-3-yl)acrylic acid (Intermediate-22) (150 mg, 0.61 mmol), HOBt (98 mg, 0.73 mmol) and EDC.HCl (232 mg, 1.22 mmol) in dry DMF (2 mL) at 20-35° C. and the reaction mixture was allowed to stir at 20-35° C. for 16 h. Then the reaction mixture was poured into ice water (50 mL) and extracted with ethyl acetate (2×50 mL). The organic layer was washed with brine (50 mL), dried over anhydrous Na$_2$SO$_4$ and filtered. The filtrate was rotary evaporated under vacuum to get residue which was purified by column chromatography using mixture of 4% methanol/dichloromethane as an eluent to get the desired compound as an off-white solid (160 mg, 51%); $^1$H NMR (400 MHz, DMSO-d$_6$) δ 10.61 (s, 1H), 8.36 (s, 1H), 8.08 (s, 1H), 7.71 (d, J=2.9 Hz, 1H), 7.61 (d, J=3.0 Hz, 1H), 7.45 (d, J=15.2 Hz, 1H), 7.30-7.14 (m, 1H), 5.68-5.65 (m, 1H), 4.28-4.20 (m, 1H), 4.08-4.02 (m, 1H), 3.80-3.72 (m, 3H), 3.68-3.60 (m, 1H), 2.79 (s, 2H), 2.18-2.04 (m, 2H), 1.08 (s, 6H); LC-MS: 409.2 (M+1)$^+$.

The below compounds were prepared by procedure similar to the one described in Example-II with appropriate variations in reactants, quantities of reagents at suitable reaction conditions. The physicochemical characteristics of the compounds are summarized herein below table.

| Comp. No | Compound structure | Characterization data ($^1$H NMR (400 MHz, DMSO-d$_6$) in δ (ppm)/LC-MS or ES-MS |
|---|---|---|
| 26 | 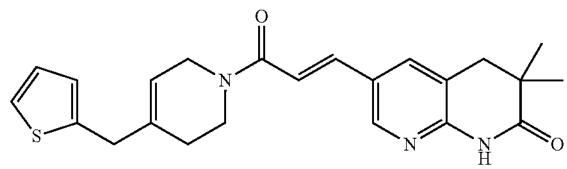 [SMILES: CC1(C)Cc2cc(/C=C/C(=O)N3CC=C(Cc4cccs4)CC3)cnc2NC1=O] | δ 10.61 (s, 1H), 8.35 (s, 1H), 8.07 (s, 1H), 7.45 (d, J = 15.1 Hz, 1H), 7.35 (d, J = 4.9 Hz, 1H), 7.30-7.14 (m, 1H), 6.96-6.92 (m, 1H), 6.90-6.86 (m, 1H), 5.58-5.55 (m, 1H), 4.26-4.16 (m, 1H), 4.08-4.00 (m, 1H), 3.80-3.72 (m, 1H), 3.68-3.60 (m, 1H), 3.54 (s, 2H), 2.79 (s, 2H), 2.14-1.98 (m, 2H), 1.08 (s, 6H); LC-MS:408.2 (M + 1)$^+$. |
| 27 | 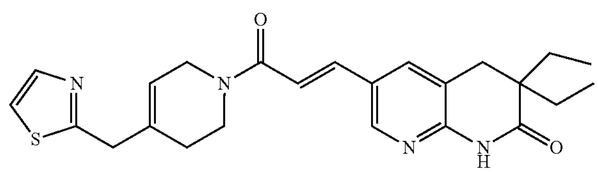 [SMILES: CCC1(CC)Cc2cc(/C=C/C(=O)N3CC=C(Cc4nccs4)CC3)cnc2NC1=O] | δ 10.60 (s, 1H), 8.33 (s, 1H), 8.10 (s, 1H), 7.71 (d, J = 3.4 Hz, 1H), 7.61 (d, J = 3.5 Hz, 1H), 7.45 (d, J = 15.2 Hz, 1H), 7.30-7.14 (m, 1H), 5.68-5.65 (m, 1H), 4.28-4.20 (m, 1H), 4.08-4.02 (m, 1H), 3.80-3.72 (m, 3H), 3.68-3.62 (m, 1H), 2.81 (s, 2H), 2.18-2.06 (m, 2H), 1.36-1.22 (m, 4H), 0.81 (t, J = 7.3 Hz, 6H); ES-MS: 437.6 (M + 1)$^+$. |
| 28 | 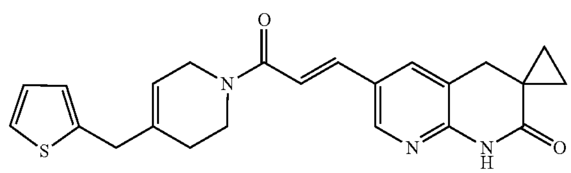 [SMILES: O=C(/C=C/c1cnc2c(c1)CC1(CC1)C(=O)N2)N1CC=C(Cc2cccs2)CC1] | δ 10.71 (s, 1H), 8.38 (s, 1H), 8.00 (s, 1H), 7.45 (d, J = 15.6 Hz, 1H), 7.35 (d, J = 4.9 Hz, 1H), 7.28-7.14 (m, 1H), 6.99-6.95 (m, 1H), 6.92-6.88 (m, 1H), 5.58-5.55 (m, 1H), 4.26-4.16 (m, 1H), 4.08-4.00 (m, 1H), 3.76-3.70 (m, 1H), 3.68-3.58 (m, 1H), 3.54 (s, 2H), 2.87 (s, 2H), 2.12-1.96 (m, 2H), 1.14-1.08 (m, 2H), 0.82-0.74 (m, 2H); LC-MS: 406.1 (M + 1)$^+$. |
| 29 | 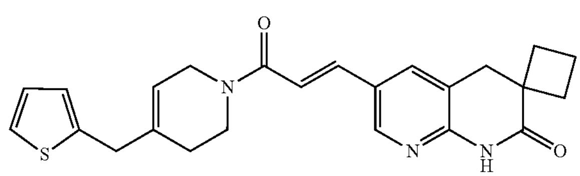 [SMILES: O=C(/C=C/c1cnc2c(c1)CC1(CCC1)C(=O)N2)N1CC=C(Cc2cccs2)CC1] | δ 10.57 (s, 1H), 8.34 (s, 1H), 8.11 (s, 1H), 7.44 (d, J = 15.7 Hz, 1H), 7.35 (d, J = 4.9 Hz, 1H), 7.30-7.14 (m, 1H), 6.99-6.95 (m, 1H), 6.92-6.86 (m, 1H), 5.60-5.56 (m, 1H), 4.26-4.18 (m, 1H), 4.08-4.00 (m, 1H), 3.78-3.72 (m, 1H), 3.68-3.60 (m, 1H), 3.54 (s, 2H), 3.06 (s, 2H), 2.40-2.30 (m, 2H), 2.10-1.93 (m, 1H), 1.92-1.83 (m, 1H), 1.82-1.72 (m, 2H), 1.00-0.94 (m, 2H); LC-MS: 420.3 (M + 1)$^+$. |
| 30 | 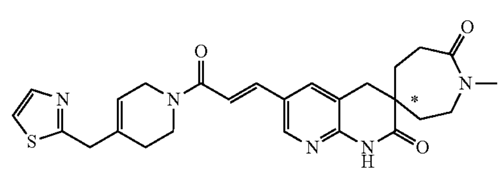 | LC-MS: 490.6 (M − 1)$^+$. |
| 31 | 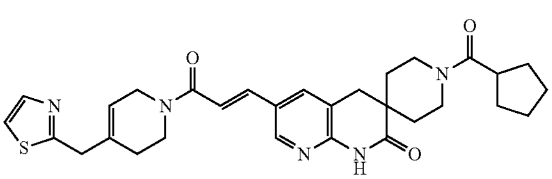 [SMILES: O=C(/C=C/c1cnc2c(c1)CC1(CCN(C(=O)C3CCCC3)CC1)C(=O)N2)N1CC=C(Cc2nccs2)CC1] | δ 10.75 (s,1H), 8.38 (d, J = 1.5 Hz, 1H), 8.09 (s, 1H), 7.71 (d, J = 3.4 Hz, 1H), 7.61 (d, J = 3.5 Hz, 1H), 7.46 (d, J = 15.2 Hz, 1H), 7.28-7.16 (m, 1H), 5.68-5.65 (s, 1H), 4.28-4.22 (m, 1H), 4.08-4.02 (m, 1H), 3.75 (s, 2H), 3.74-3.62 (m, 4H), 3.54-3.44 (m, 1H), 3.41-3.36 (m, 1H), 3.03-2.92 (m, 1H), 2.97 (s, 2H), 2.18-2.06 (m, 2H), 1.86-1.72 (m, 4H), 1.71-1.54 (m, 4H), 1.53-1.44 (m, 2H), 1.42-1.26 (m, 2H); ES-MS: 546.2 (M + 1)$^+$. |

* mixture of isomers (for compound 30)

| Comp. No | Compound structure | Characterization data ($^1$H NMR (400 MHz, DMSO-$d_6$) in δ (ppm)/LC-MS or ES-MS |
|---|---|---|
| 32 | 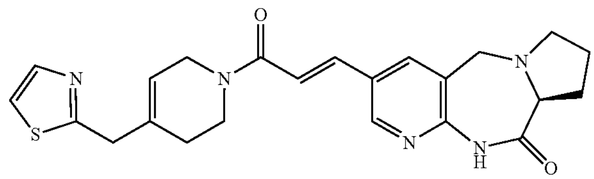 [SMILES: O=C1Nc2ncc(/C=C/C(=O)N3CC=C(Cc4nccs4)CC3)cc2CN2CCC[C@@H]12] | δ 10.35 (s, 1H), 8.54 (d, J = 1.9 Hz, 1H), 8.20 (d, J = 6.9 Hz, 1H), 7.71 (d, J = 3.4 Hz, 1H), 7.61 (d, J = 3.4 Hz, 1H), 7.49 (d, J = 15.7 Hz, 1H), 7.36-7.24 (m, 1H), 5.68-5.64 (m, 1H), 4.28-4.23 (m, 1H), 4.08-4.04 (m, 1H), 3.94 (d, J = 12.2 Hz, 1H), 3.78-3.71 (m, 3H), 3.68-3.64 (m, 1H), 3.53 (d, J = 12.7 Hz, 1H), 3.49-3.45 (m, 1H), 2.90-2.86 (m, 1H), 2.64-2.54 (m, 1H), 2.34-2.26 (m, 1H), 2.18-2.06 (m, 2H), 1.85-1.69 (m, 3H); ES-MS: 436.4 (M + 1)$^+$. |
| 33 | 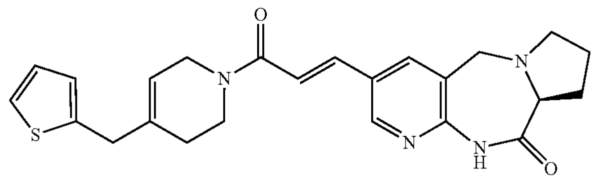 [SMILES: O=C1Nc2ncc(/C=C/C(=O)N3CC=C(Cc4cccs4)CC3)cc2CN2CCC[C@@H]12] | δ 10.35 (bs, 1H), 8.55 (s, 1H), 8.21 (s, 1H), 7.49 (d, J = 15.6 Hz, 1H), 7.37-7.33 (m, 1H), 7.33-7.24 (m, 1H), 6.96 (dd, J = 3.6, 5.1 Hz, 1H), 6.87 (d, J = 2.9 Hz, 1H), 5.60-5.58 (m, 1H), 4.26-4.20 (m, 1H), 4.06-4.00 (m, 1H), 3.94 (d, J = 12.7 Hz, 1H), 3.78-3.74 (m, 1H), 3.66-3.60 (m, 1H), 3.55 (s, 2H), 3.54-3.50 (m, 1H), 3.50-3.44 (m, 1H), 2.88-2.84 (m, 1H), 2.66-2.56 (m, 1H), 2.34-2.26 (m, 1H), 2.14-1.98 (m, 2H), 1.88-1.68 (m, 3H); ES-MS: 435.3 (M + 1)$^+$. |

Example-III

Synthesis of (E)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one 2,2,2-trifluoroacetate (Compound 34)

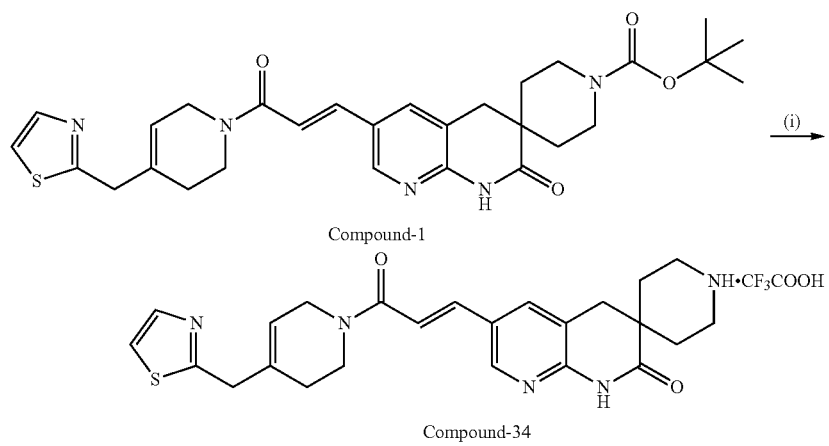

To a stirred solution of (E)-tert-butyl 2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxylate (Compound 1) (0.6 g, 1.52 mmol) in CH$_2$Cl$_2$ (15 mL) was added trifluoro acetic acid (0.58 mL, 7.61 mmol) at 20-35° C. and the reaction mixture was allowed to stir at 20-35° C. for 4 h. Then the reaction mixture was rotary evaporated under vacuum to get residue which was triturated with diethyl ether to get the desired compound as a yellow solid (500 mg, 82%); $^1$H NMR (400 MHz, DMSO-$d_6$) δ 10.88 (s, 1H), 8.50-8.32 (m, 3H), 8.07 (s, 1H), 7.71 (d, J=3.4 Hz, 1H), 7.61 (d, J=3.4 Hz, 1H), 7.46 (d, J=15.7 Hz, 1H), 7.28-7.14 (m, 1H), 5.68-5.65 (m, 1H), 4.26-4.20 (m, 1H), 4.08-4.02 (m, 1H), 3.78-3.72 (m, 3H), 3.68-3.62 (m, 1H), 3.16-3.06 (m, 4H), 2.97 (s, 2H), 2.20-2.04 (m, 2H), 2.03-1.92 (m, 2H), 1.62-1.48 (m, 2H); ES-MS: 450.2 (M+1)$^+$.

Example-IV

Synthesis of (E)-1'-methyl-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one. (Compound 35)

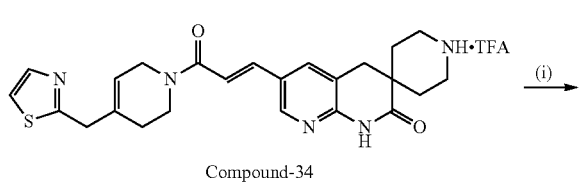

Compound-34

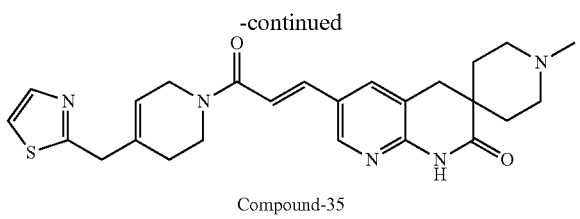

Compound-35

To a stirred solution of (E)-β-methyl-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound 34) (200 mg, 0.35 mmol) in methanol (3 mL) was added 37% formaldehyde solution (0.086 mL, 1.07 mmol), followed by triethylamine (0.15 mL, 1.07 mmol) at 20-35° C. and the mixture was continued stirring at 20-35° C. for 30 minutes. Then NaBH₄ (20 mg, 0.53 mmol) was added slowly portionwise at 0° C. and the reaction mixture was allowed to stir at 20-35° C. for 16 h. The reaction mixture was rotary evaporated under vacuum to get residue which was purified by preparative HPLC to get the desired compound as an off-white solid (25 mg, 15%); ¹H NMR (400 MHz, DMSO-d₆) δ 10.66 (s, 1H), 8.34 (s, 1H), 8.15 (s, 1H), 7.71 (d, J=2.9 Hz, 1H), 7.61 (d, J=2.5 Hz, 1H), 7.45 (d, J=15.6 Hz, 1H), 7.30-7.14 (m, 1H), 5.68-5.64 (m, 1H), 4.26-4.22 (m, 1H), 4.06-4.02 (m, 1H), 3.80-3.72 (m, 3H), 3.68-3.62 (m, 1H), 2.90 (s, 2H), 2.62-2.54 (m, 2H), 2.28-2.04 (m, 4H), 2.19 (s, 3H), 1.90-1.78 (m, 2H), 1.42-1.28 (m, 2H); LC-MS: 464.3 (M+1)⁺. Preparative HPLC conditions: Column-Phenomenex Luna C18 (2) (250×21.1 mm, 5µ), Mobile Phase: (A) 0.1% TFA(Aq); (B) ACN; Flow rate: 15 ml/min.

The below compound 36 was prepared by following the process according to compound 35 and their physicochemical characteristics are summarized herein below in the Table. CH₃COOH and NaBH₃CN was used instead of NaBH₄ in the preparation of compound 36.

| Com. No | Structure | Characterization data (¹H NMR (400 MHz, DMSO-d₆ in δ (ppm)/ES-MS |
|---|---|---|
| 36 | 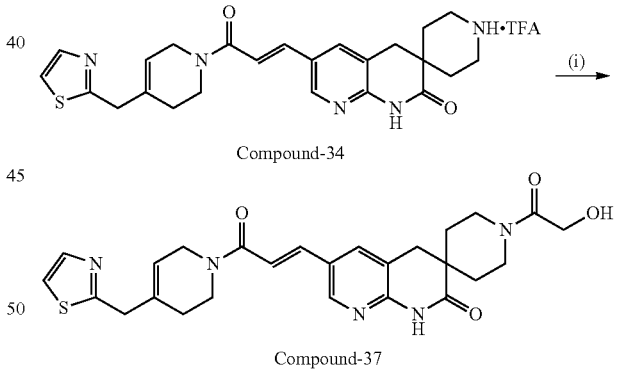 | δ 10.64 (s, 1H), 8.34 (s, 1H), 8.14 (s, 1H), 7.71 (d, J = 3.4 Hz, 1H), 7.61 (d, J = 3.5 Hz, 1H), 7.45 (d, J = 15.1 Hz, 1H), 7.28-7.14 (m, 1H), 5.68-5.64 (m, 1H), 4.28-4.20 (m, 1H), 4.08-4.02 (m, 1H), 3.80-3.72 (m, 3H), 3.68-3.60 (m, 1H), 2.92 (s, 2H), 2.78-2.66 (m, 3H), 2.20-2.04 (m, 2H), 1.86-1.72 (m, 2H), 1.68-1.58 (m, 2H), 1.40-1.26 (m, 2H), 0.44-0.34 (m, 2H), 0.28-0.22 (m, 2H); ES-MS: 490.2 (M + 1)⁺. |

Compound 37: Synthesis of (E)-1'-(2-hydroxyacetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one Compound-34

Compound-37

DIPEA (0.38 mL, 2.13 mmol) was added to a stirred solution of (E)-6-(3-oxo-3-(4-(thiazol-2-ylmethyl)-5,6-dihydropyridin-1(2H)-yl)prop-1-en-1-yl)-1H-spiro[[1,8]naph-thyridine-3,4'-piperidin]-2(4H)-one 2,2,2-trifluoroacetate (Compound 34) (200 mg, 0.35 mmol), Glycolic acid (80 mg, 1.06 mmol), HOBt (96 mg, 0.70 mmol) and EDC.HCl (170 mg, 0.88 mmol) in dry DMF (4 mL) at 20-35° C. and the reaction mixture was allowed to stir at 20-35° C. for 16 h. Then the reaction mixture was diluted with water (30 mL) and extracted with ethyl acetate (2×30 mL). The organic layer was washed with brine (30 mL), dried over anhydrous Na₂SO₄ and filtered. The filtrate was rotary evaporated under vacuum to get residue which was purified by column chromatography using mixture of 4% methanol/dichloromethane as an eluent to get the desired compound as a light yellow solid (40 mg, 22%); $^1$H NMR (400 MHz, DMSO-d$_6$) δ 10.75 (s, 1H), 8.38 (d, J=2.0 Hz, 1H), 8.09 (s, 1H), 7.71 (d, J=3.4 Hz, 1H), 7.61 (d, J=3.5 Hz, 1H), 7.45 (d, J=15.7 Hz, 1H), 7.28-7.14 (m, 1H), 5.68-5.66 (m, 1H), 4.50 (t, J=5.4 Hz, 1H), 4.28-4.22 (m, 1H), 4.10-4.04 (m, 3H), 3.78-3.74 (m, 3H), 3.74-3.62 (m, 3H), 3.54-3.38 (m, 2H), 2.96 (s, 2H), 2.20-2.06 (m, 2H), 1.86-1.68 (m, 2H), 0.46-0.32 (m, 2H); ES-MS: 508.2 (M+1)$^+$.

The below compound 38 was prepared by following the process according to compound 37 by using appropriate reactants, reagents at suitable conditions. The physicochemical characteristics are summarized herein below in the Table.

| Comp. No | Structure | Characterization data ($^1$H NMR (400 MHz, DMSO-d$_6$ in δ (ppm)))/LC-MS |
|---|---|---|
| 38 | 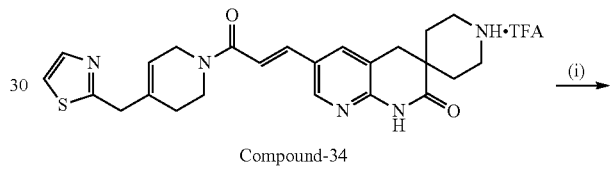 | δ 10.78 (s, 1H), 8.39 (s, 1H), 8.09 (s, 1H), 7.82 s, 1H), 7.71 (d, J = 2.5 Hz, 1H), 7.61 (s, 1H), 7.46 (d, J = 15.6 Hz, 1H), 7.30-7.14 (m, 1H), 6.97 (d, J = 2.5 Hz, 1H), 6.61 (s, 1H), 5.68-5.65 (m, 1H), 4.28-4.20 (m, 1H), 4.08-4.02 (m, 1H), 3.88-3.80 (m, 2H), 3.80-3.74 (m, 3H), 3.72-3.58 (m, 3H), 2.99 (s, 2H), 2.20-2.06 (m, 2H), 1.88-1.78 (m, 2H), 1.48-1.40 (m, 2H); LC-MS: 544.3 (M + 1)$^+$. |

Compound 39: Synthesis of (E)-2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide

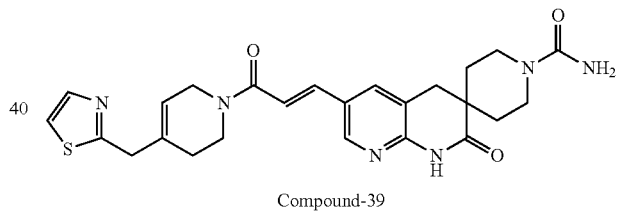

To a stirred solution of (E)-6-(3-oxo-3-(4-(thiazol-2-ylmethyl)-5,6-dihydro pyridin-1(2H)-yl)prop-1-en-1-yl)-1H-spiro[[1,8]naph-thyridine-3,4'-piperidin]-2(4H)-one 2,2,2-trifluoroacetate (Compound 34) (150 mg, 0.26 mmol) in DMSO (2 mL) were added triethylamine (110 mg, 1.04 mmol) and phenyl carbamate (44 mg, 0.32 mmol) at 20-35° C. and the reaction mixture was allowed to stir at 20-35° C. for 16 h. Then the reaction mixture was poured into ice water (50 mL), obtained solid was filtered, washed with water and dried under vacuum to get the desired compound as a yellow solid (40 mg, 31%); $^1$H NMR (400 MHz, DMSO-d$_6$) δ 10.71 (s, 1H), 8.37 (d, J=2.0 Hz, 1H), 8.10 (s, 1H), 7.71 (d, J=3.4 Hz, 1H), 7.61 (d, J=3.4 Hz, 1H), 7.45 (d, J=15.2 Hz, 1H), 7.28-7.14 (m, 1H), 5.93 (s, 2H), 5.68-5.65 (m, 1H), 4.28-4.20 (m, 1H), 4.08-4.02 (m, 1H), 3.76-3.72 (m, 3H), 3.66-3.62 (m, 1H), 3.60-3.52 (m, 2H), 3.18 (t, J=10.0 Hz, 2H), 2.95 (s, 2H), 2.20-2.06 (m, 2H), 1.76-1.66 (m, 2H), 1.34-1.24 (m, 2H); ES-MS: 493.3 (M+1)$^+$.

Example-V

Synthesis of (E)-4-oxo-4-(2-oxo-6-(3-oxo-3-(4-(thiazol-2-ylmethyl)-5,6-dihydropyridin-1(2H)-yl)prop-1-en-1-1-2,4-dihydro-1H-spiro[[1,8]naphthyridine-3,4'-piperidine]-1'-yl)butanoic acid (Compound 40)

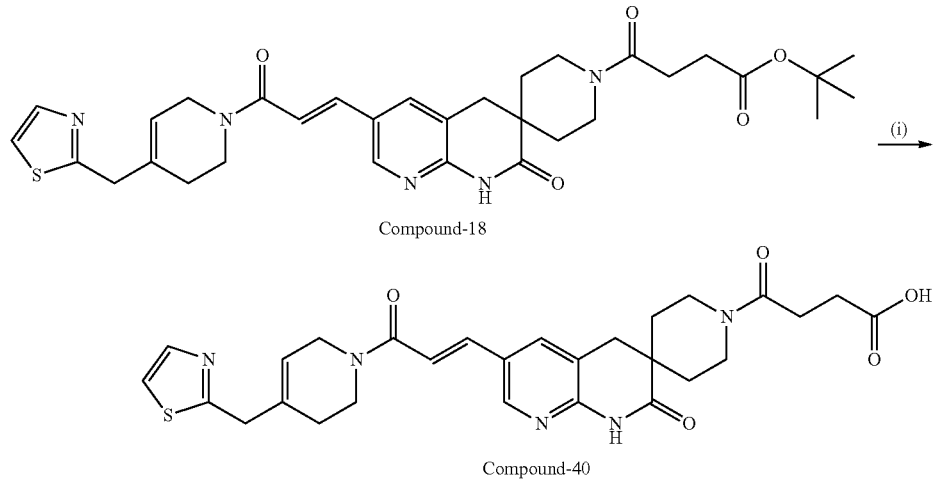

The process of this step was adopted from preparation of compound 34. The desired compound obtained as an off-white solid (20 mg, 18%); NMR (400 MHz, DMSO-$d_6$) δ 11.98 (brs, 1H), 10.75 (s, 1H), 8.38 (d, J=1.5 Hz, 1H), 8.09 (s, 1H), 7.71 (d, J=3.4 Hz, 1H), 7.61 (d, J=3.4 Hz, 1H), 7.46 (d, J=15.2 Hz, 1H), 7.28-7.14 (m, 1H), 5.68-5.64 (m, 1H), 4.28-4.20 (m, 1H), 4.08-4.02 (m, 2H), 3.80-3.72 (m, 3H), 3.72-3.68 (m, 1H), 3.68-3.58 (m, 2H), 3.48-3.36 (m, 2H), 2.96 (s, 2H), 2.46-2.38 (m, 3H), 2.20-2.04 (m, 2H), 1.88-1.76 (m, 1H), 1.74-1.64 (m, 1H), 1.46-1.28 (m, 2H); LC-MS: 550.2 (M+H)$^+$.

Example-VI

Synthesis of (E)-1'-(2-amino acetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one hydrochloride (Compound 41)

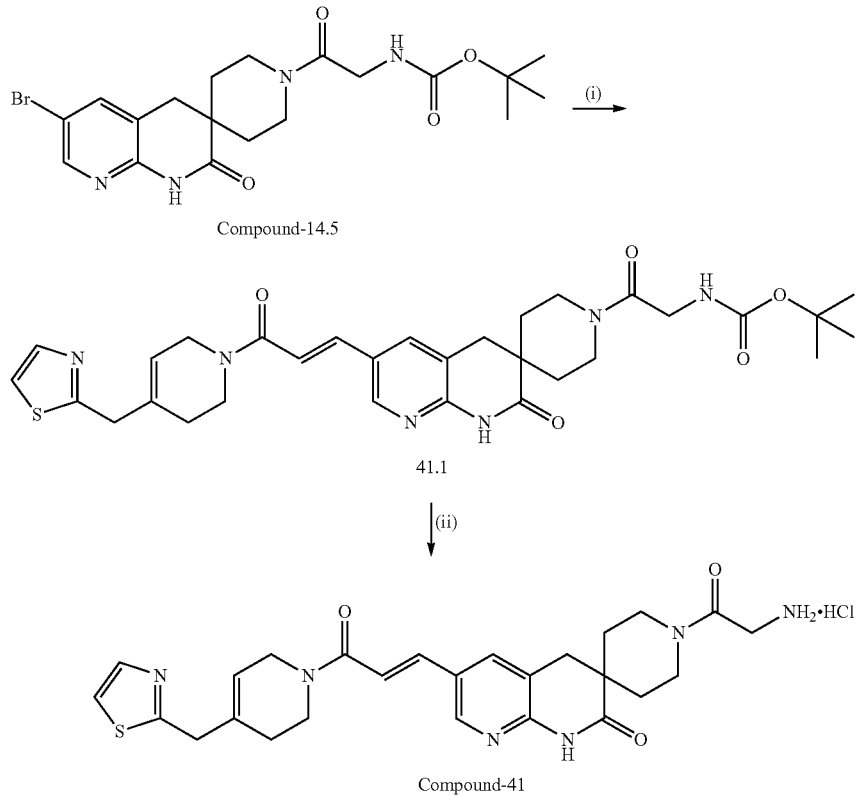

Step-(i): Synthesis of (E)-tert-butyl (2-oxo-2-(2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidin]-1'-yl)ethyl)carbamate (41.1)

The process of this step was adopted from preparation of compound 1. The desired compound obtained as a yellow solid (40 mg, 13%); $^1$H NMR (400 MHz, DMSO-$d_6$) δ 10.76 (s, 1H), 8.38 (d, J=2.0 Hz, 1H), 8.09 (s, 1H), 7.71 (d, J=3.4 Hz, 1H), 7.61 (d, J=3.5 Hz, 1H), 7.45 (d, J=15.7 Hz, 1H), 7.28-7.14 (m, 1H), 6.71 (t, J=5.9 Hz, 1H), 5.68-5.65 (m, 1H), 4.26-4.20 (m, 1H), 4.08-4.02 (m, 1H), 3.82-3.72 (m, 4H), 3.72-3.52 (m, 4H), 3.48-3.30 (m, 2H), 2.96 (s, 2H), 2.20-2.06 (m, 2H), 1.88-1.68 (m, 2H), 1.46-1.30 (m, 2H), 1.38 (s, 9H).

Step-(ii): Synthesis of (E)-1'-(2-aminoacetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one hydrochloride (Compound 41)

To a stirred solution of (E)-tert-butyl (2-oxo-2-(2-oxo-6-(3-oxo-3-(4-(thiazol-2-ylmethyl)-5,6-dihydropyridin-1(2H)-yl)prop-1-en-1-yl)-2,4-dihydro-1Hspiro[[1,8]naphthyridine-3,4'-piperidin]-1'-yl)ethyl)carbamate (41.1) (20 mg, 0.03 mmol) in 1,4-dioxane (1 mL) was added 2M HCl in ether (0.24 mL) drop wise at 0° C. and the reaction mixture was allowed to stir at 20-35° C. for 3 h. Then the reaction mixture was rotary evaporated under vacuum to get residue which was triturated with diethyl ether to get the desired compound as a brown solid (20 mg); $^1$H NMR (400 MHz, DMSO-$d_6$) δ 10.79 (s, 1H), 8.41 (d, J=2.0 Hz, 1H), 8.09 (s, 1H), 8.08-8.00 (m, 3H), 7.71 (d, J=3.4 Hz, 1H), 7.61 (d, J=3.4 Hz, 1H), 7.46 (d, J=15.2 Hz, 1H), 7.28-7.14 (m, 1H), 5.68-5.65 (m, 1H), 4.26-4.18 (m, 1H), 4.08-4.02 (m, 1H), 3.92-3.80 (m, 4H), 3.80-3.72 (m, 3H), 3.68-3.60 (m, 1H), 3.54-3.40 (m, 2H), 2.98 (s, 2H), 2.20-2.04 (m, 2H), 1.92-1.83 (m, 1H), 1.82-1.68 (m, 1H), 1.48-1.32 (m, 2H); ES-MS: 507.3 (M+1)$^+$.

Example-VII

Synthesis of (E)-1'-(2-(tert-butylamino)acetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one 2,2,2-trifluoroacetate (Compound 42)

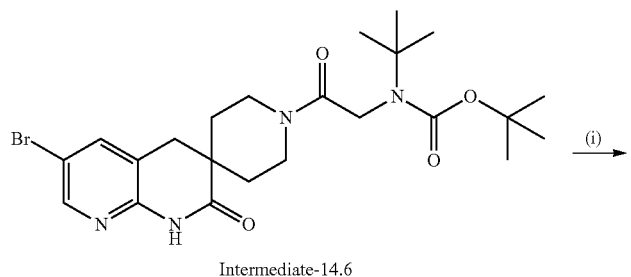

Intermediate-14.6

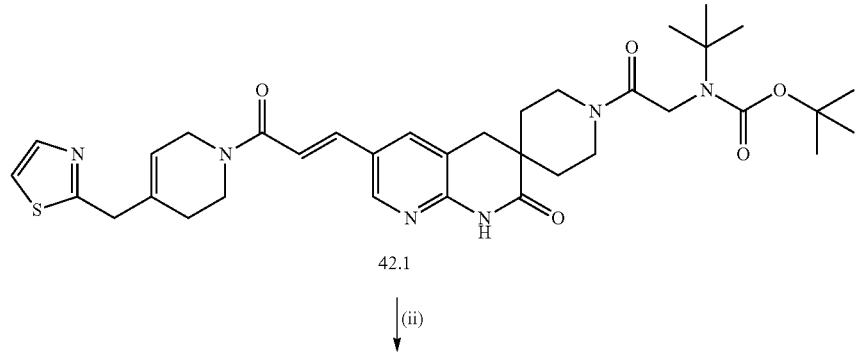

42.1

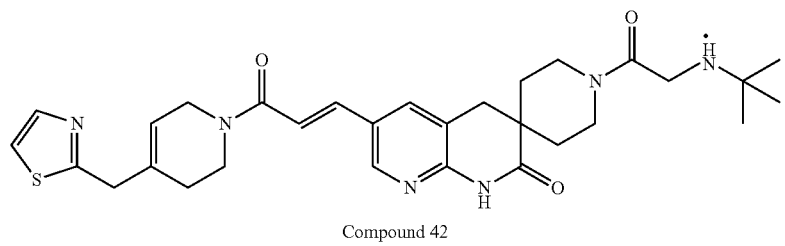

Compound 42

Step-(i): Synthesis of (E)-tert-butyl tert-butyl(2-oxo-2-(2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidin]-1'-yl)ethyl)carbamate (42.1)

The process of this step was adopted from preparation of compound 1. The desired compound obtained as a yellow solid (120 mg, 17%); $^1$H NMR (400 MHz, DMSO-$d_6$) δ 10.66 (s, 1H), 8.37 (s, 1H), 8.07 (s, 1H), 7.70 (d, J=3.4 Hz, 1H), 7.59 (d, J=3.5 Hz, 1H), 7.45 (d, J=15.6 Hz, 1H), 7.28-7.14 (m, 1H), 5.68-5.65 (m, 1H), 4.28-4.16 (m, 1H), 4.11 (s, 2H), 4.08-4.02 (m, 1H), 3.74 (s, 2H), 3.73-3.56 (m, 4H), 3.48-3.32 (m, 2H), 3.22-3.10 (m, 2H), 2.96 (s, 2H), 2.20-2.06 (m, 2H), 1.88-1.68 (m, 2H), 1.37 (s, 9H), 1.33 (s, 9H).

Step-(ii): Synthesis of (E)-1'-(2-(tert-butylamino)acetyl)-6-(3-oxo-3-(4-(thiazol-2-yl methyl)-5,6-dihydropyridin-1(2H)-yl)prop-1-en-1-yl)-1H-spiro[[1,8]naphthyridine-3,4'-piperidin]-2(4H)-one 2,2,2-trifluoroacetate (Compound 42)

The process of this step was adopted from preparation of compound 34. The desired compound obtained as a yellow solid (10 mg); $^1$H NMR (400 MHz, DMSO-$d_6$) δ 10.75 (s, 1H), 8.38 (d, J=1.0 Hz, 1H), 8.09 (s, 1H), 7.71 (d, J=3.4 Hz, 1H), 7.61 (d, J=3.5 Hz, 1H), 7.46 (d, J=15.2 Hz, 1H), 7.28-7.14 (m, 1H), 5.68-5.65 (m, 1H), 4.28-4.20 (m, 1H), 4.08-4.02 (m, 1H), 3.75 (s, 2H), 3.74-3.58 (m, 5H), 3.48-3.36 (m, 4H), 2.96 (s, 2H), 2.20-2.04 (m, 2H), 1.88-1.76 (m, 1H), 1.74-1.62 (m, 1H), 1.46-1.30 (m, 2H), 1.01 (s, 9H); ES-MS: 563.3 (M+1)$^+$.

Example-VIII

Synthesis of (E)-1-(2-hydroxyacetyl)-6'-(3-oxo-3-(4-(thiazol-2-ylmethyl)-5,6-dihydropyridin-1(2H)-yl)prop-1-en-1-yl)-1'H-spiro[azetidine-3,3'-[1,8]naphthyridin]-2'(4'H)-one (Compound 43)

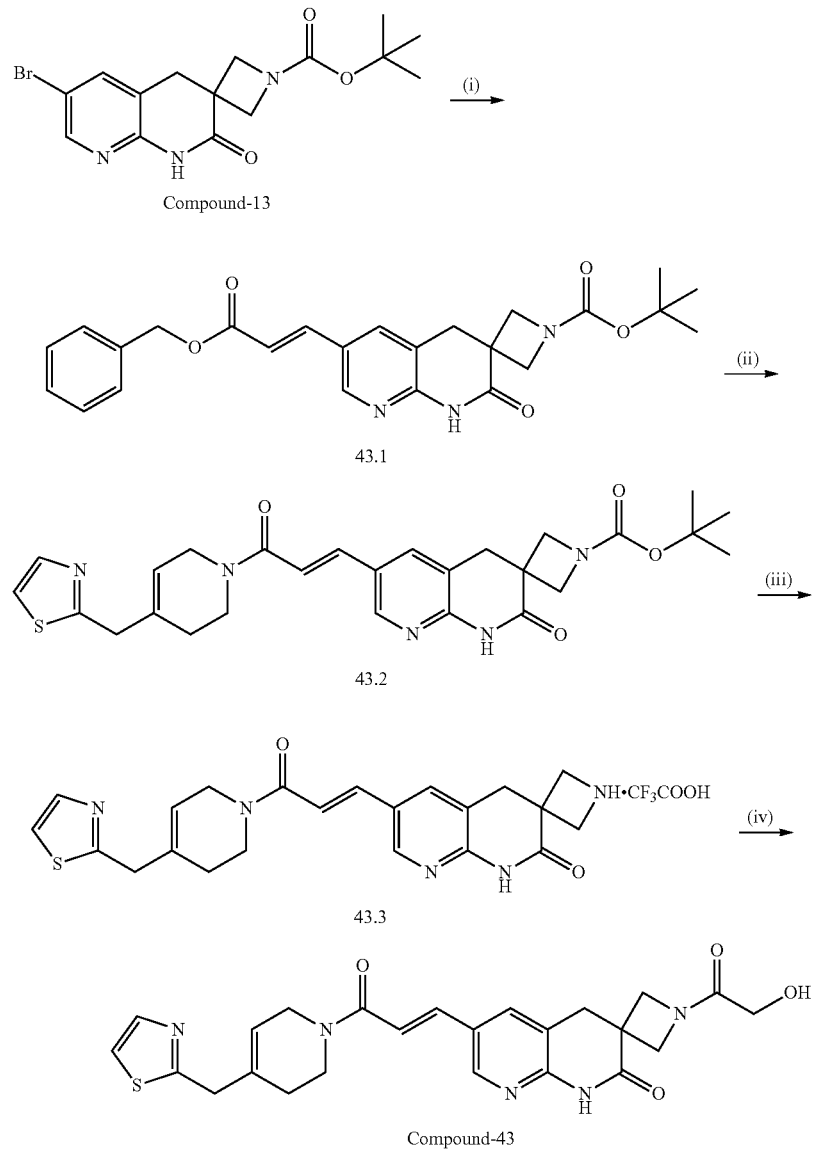

Step-(i): Synthesis of (E)-tert-butyl 6'-(3-(benzyloxy)-3-oxoprop-1-en-1-yl)-T-oxo-2',4'-dihydro-1'H-spiro[azetidine-3,3'-[1,8]naphthyridine]-1-carboxylate (43.1)

The process of this step was adopted from step-(i) of intermediate-22. The desired compound obtained as an off-white solid (750 mg, 62%); $^1$H NMR (400 MHz, DMSO-$d_6$) δ 10.98 (s, 1H), 8.44 (d, J=1.9 Hz, 1H), 8.09 (d, J=1.4 Hz, 1H), 7.66 (d, J=16.1 Hz, 1H), 7.46-7.32 (m, 5H), 6.68 (d, J=16.2 Hz, 1H), 5.23 (s, 2H), 4.08-3.98 (m, 2H), 3.68-3.58 (m, 2H), 3.24 (s, 2H), 1.38 (s, 9H); ES-MS: 448.4 (M−1)$^+$.

Step-(ii): Synthesis of (E)-tert-butyl T-oxo-6'-(3-oxo-3-(4-(thiazol-2-ylmethyl)-5,6-dihydropyridin-1(2H)-yl)prop-1-en-1-yl)-2',4'-dihydro-1'H-spiro[azetidine-3,3'-[1,8]naphthyridine]-1-carboxylate (43.2)

To a stirred solution of (E)-tert-butyl 6'-(3-(benzyloxy)-3-oxoprop-1-en-1-yl)-2'-oxo-2',4'-dihydro-1'H-spiro[azetidine-3,3'-[1,8]naphthyridine]-1-carboxylate (43.1) (750 mg, 1.67 mmol) in ethanol/DCM (15 mL/15 mL) was added 1M NaOH solution (100 mg in 2.5 mL water; 2.50 mmol) at 0° C. and the reaction mixture was allowed to stir at 20-35° C. for 16 h. The reaction mixture was rotary evaporated under vacuum, resultant solid was acidified with 1M HCl solution at 0° C., filtered and dried. Then the obtained solid (200 mg, 0.55 mmol) was added to a stirred solution of 2-((1,2,3,6-tetrahydropyridin-4-yl)methyl)thiazole hydrochloride (Intermediate-2) (144 mg, 0.66 mmol), HOBt (90 mg, 0.66 mmol) and EDC.HCl (213 mg, 1.11 mmol) in dry DMF (1 mL) at 20-35° C. After 5 min, DIPEA (0.3 mL, 1.67 mmol) was added and the reaction mixture was allowed to stir at 20-35° C. for 16 h. The reaction mixture was poured into ice water (20 mL), obtained solid was filtered, washed with water and dried under vacuum to get the desired compound as an off-white solid (110 mg, 38%); NMR (400 MHz, DMSO-$d_6$) δ 10.91 (s, 1H), 8.39 (d, J=1.5 Hz, 1H), 8.10 (s, 1H), 7.71 (d, J=3.4 Hz, 1H), 7.61 (d, J=3.5 Hz, 1H), 7.45 (d, J=15.2 Hz, 1H), 7.28-7.14 (m, 1H), 5.68-5.65 (m, 1H), 4.28-4.22 (m, 1H), 4.10-4.02 (m, 3H), 3.75 (s, 2H), 3.75-3.72 (m, 1H), 3.70-3.60 (m, 3H), 3.24 (s, 2H), 2.20-2.04 (m, 2H), 1.38 (s, 9H).

Step-(iii): Synthesis of (E)-6'-(3-oxo-3-(4-(thiazol-2-ylmethyl)-5,6-dihydropyridin-1(2H)-yl)prop-1-en-1-yl)-1'H-spiro[azetidine-3,3'-[1,8]naphthyridin]-2'(4'H)-one 2,2,2-trifluoro acetate (43.3)

The process of this step was adopted from preparation of compound 34. The desired compound obtained as a pale brown solid (80 mg, 91%); LC-MS: 422.2 (M+1)$^+$.

Step-(iv): Synthesis of (E)-1-(2-hydroxyacetyl)-6'-(3-oxo-3-(4-(thiazol-2-ylmethyl)-5,6-dihydropyridin-1(2H)-yl)prop-1-en-1-yl)-1'H-spiro[azetidine-3,3'-[1,8]naphthyridin]-2'(4'H)-one (Compound 43)

The process of this step was adopted from preparation of compound 37. The desired compound obtained as a brown solid (15 mg, 16%); LC-MS: 480.2 (M+1)$^+$.

Pharmacological Data:
Biological Screening of the Compounds of Formula (1) of the Present Invention The biological screening of the various tetrahydropyridine derivatives of formula (1) was carried out using FabI protocol designed for evaluating enzymatic assay for FabI. Following protocol was used for the evaluation purpose and the results are summarized below.

FabI Enzymatic Assay Protocol (S. aureus)

The enzymatic assay is based on the decrease in absorbance at 340 nm resulting from the oxidation of NADPH accompanying the reduction of enoyl—ACP, catalyzed by FabI enzyme. The assay buffer was 100 mM Sodium ADA (N-[2-Acetamido]iminodiacetic acid) buffer, pH 6.5. 20 µl of FabI enzyme (2400 ng/assay) and 100 of NADH (375 µM) were pre-incubated with 10 µl of selected compounds for 30 minutes and the reaction was started by adding 10 µl of Crotonoyl CoA (250 µM). The reaction volume was made upto to 1004 with Sodium ADA buffer and the plate was incubated for 2 h at room temperature. The reduction of NADH was monitored by following the decrease in absorbance at 340 nm. $IC_{50}$ values were estimated by fitting the dose-response data to sigmoidal dose response (variable slope), curve fitting program using Graphpad Prism software V5.

$IC_{50}$ values of the selected compounds of present invention were provided in below table, Compounds exhibiting $IC_{50}$ values ≤0.4 µM were grouped as 'a', compounds exhibiting $IC_{50}$ value in the range 0.41 µM to 0.6 µM were grouped as 'b' and the compounds exhibiting $IC_{50}$ value ≥0.61 µM were grouped as 'c'.

| Group | Compound No |
|---|---|
| a | 2, 3, 6, 7, 14, 18, 19, 20, 21, 22, 25, 27, 29, 30, 31, 32, 33, 36, 37, 38, 41, 42 |
| b | 4, 8, 10, 12, 26, 34, 39 |
| c | 11, 17, 24, 28, 35 |

MIC Determination Using Broth Microdilution Method

Minimum Inhibitory Concentration (MIC) was determined by broth microdilution method as per CLSI guidelines. Serial two-fold dilution of the compounds was made using CAMHB in 96 well microtitre plates at twice the desired final concentration. 50 µL of the adjusted inoculum suspension was dispensed into each well to give a final inoculum density of 5×10$^5$ CFU/mL. Broth, compound and organism controls were set up. Recommended quality control strain was incorporated in the study. Plates were incubated at 35±2° C. for 16-20 hours in an ambient air incubator. After the incubation period, growth of organism in the wells was detected by unaided eye facilitated by a viewing device. The amount of growth in the wells containing the antibiotic was compared with the amount of growth in organism control wells (no antibiotic) to help in determining the end point. MIC was the lowest concentration of the antibiotic/compound which inhibits bacterial growth as detected by unaided eye and expressed as µg/mL. The lowest concentration of antimicrobial agent that completely inhibits growth of the organism as detected by the unaided eye was taken as MIC. MIC values (µg/mL) for selected compounds of the present invention were provided in below table:

| | MIC (µg/mL) | | |
|---|---|---|---|
| Comp. No | MSSA | MRSA | MRSE |
| 1 | 0.5 | 0.5 | 1 |
| 2 | 0.25 | 0.25 | 0.25 |
| 3 | 0.06 | 0.06 | 0.06 |
| 5 | 0.06 | 0.06 | 0.06 |

-continued

| Comp. No | MIC (μg/mL) | | |
|---|---|---|---|
| | MSSA | MRSA | MRSE |
| 6 | 0.12 | 0.12 | 0.25 |
| 8 | 0.06 | 0.06 | 0.06 |
| 9 | 0.06 | 0.06 | 0.12 |
| 11 | 0.03 | 0.06 | 0.06 |
| 12 | 0.25 | 0.25 | 0.50 |
| 14 | 0.06 | 0.06 | 0.12 |
| 15 | 0.03 | 0.03 | 0.03 |
| 18 | 0.25 | 0.25 | 0.5 |
| 20 | 0.06 | 0.06 | 0.06 |
| 21 | 0.12 | 0.12 | 0.12 |
| 22 | 0.03 | 0.03 | 0.03 |
| 24 | 0.25 | 0.25 | 0.5 |
| 25 | 0.12 | 0.12 | 0.25 |
| 26 | 0.03 | 0.03 | 0.06 |
| 28 | 0.12 | 0.12 | 0.12 |
| 29 | 0.03 | 0.03 | 0.03 |
| 30 | 0.12 | 0.12 | 0.12 |
| 33 | 0.25 | 0.25 | 0.5 |
| 37 | 0.25 | 0.25 | 0.25 |
| 38 | 0.06 | 0.06 | 0.06 |

In Vivo Efficacy in Systemic Infection Model $ED_{50}$ was determined in systemic infection model using pathogen-free CD-1 mice (males and females, 18-22 grams, 6 animals per group). Animals were administered lethal dose ($1\times10^8$ cfu/animal) of overnight grown bacterial culture Methicillin Resistant/Sensitive *S. aureus* (AUCC 448, AUCC 446 and MSSA ATCC 29213) by intra-peritoneal route in 5% hog gastric mucin. Treatment was initiated one hour post-infection by oral/i.v. route. Selected compounds of the present invention was formulated in 0.2% sodium carboxymethyl cellulose and 0.25% Tween-80 for oral dosing & 5% DMSO & 20% Hpβcd for i.v. dosing, standard antibiotics were formulated following the manufacturer's directions and were administered as b.i.d/q.d. Animals were observed for survival/mortality for five days and $ED_{50}$ value was calculated by non-linear regression method detailed herein below table.

| Comp. No | In vivo Efficacy Route and Dosing |
|---|---|
| 2 | p.o., q.d. × 1 day |
| 3 | p.o., q.d. × 1 day |
| 6 | p.o., q.d. × 1 day |
| 21 | p.o., q.d. × 1 day |
| 25 | p.o., q.d. × 1 day |

The selected compounds of the present invention display good in vivo efficacy properties ($ED_{50}$) and protected mice from mortality due to infection.

We claim:
1. A compound of formula (1)

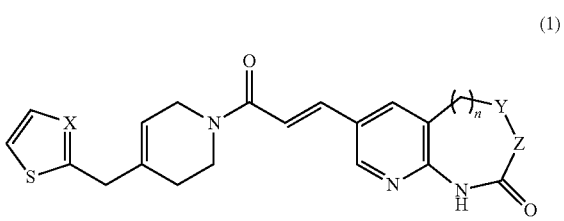

(1)

or a pharmaceutically acceptable salt or a pharmaceutically acceptable stereoisomer thereof, wherein,
X represents N or CH;
Y represents $NR_1$ or $CHR_1$;
Z represents $CR_2R_3$;
$R_1$ represents hydrogen or alkyl;
$R_2$ and $R_3$ are independently selected from hydrogen and alkyl;
alternatively, $R_2$ and $R_3$ may be taken together with the carbon atoms to which they are attached to form an optionally substituted 3-7 membered ring containing 0-3 hetero atoms or groups; wherein the optional substituent is $R_4$ and the heteroatoms are independently selected from N, O, NH and CO in any stable combination;
alternatively, $R_1$ and $R_2$ may be taken together with the carbon or nitrogen atom to which they are attached to form 5-membered fused ring;
$R_4$ at each occurrence is selected from alkyl, —$COOR_5$, —$COR_5$, —$CONR_5R_5$, —$SO_2R_5$, —$COCH_2OR_5$, —$CO(CH_2)_2COOR_5$, —$COCH_2NR_5R_5$ and cycloalkyl;
$R_5$ at each occurrence is selected from hydrogen, alkyl, cycloalkyl and heterocyclyl; and
'n' is selected from an integer 0 or 1.

2. The compound according to claim 1, wherein X is N.
3. The compound according to claim 1, wherein Y is $CHR_1$.
4. The compound according to claim 3, wherein $R_1$ is hydrogen.
5. The compound according to claim 1 is a compound of formula (1a)

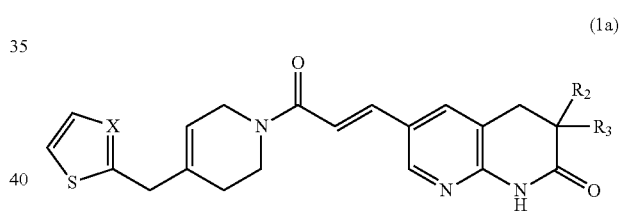

(1a)

or a pharmaceutically acceptable salt or a pharmaceutically acceptable stereoisomer thereof,
wherein;
X represents N or CH;
both $R_2$ and $R_3$ are alkyl;
or $R_2$ and $R_3$ can be taken together with the carbon atoms to which they are attached to form a 3-6 membered cycloalkyl.

6. The compound according to claim 5 is a compound of formula (1b)

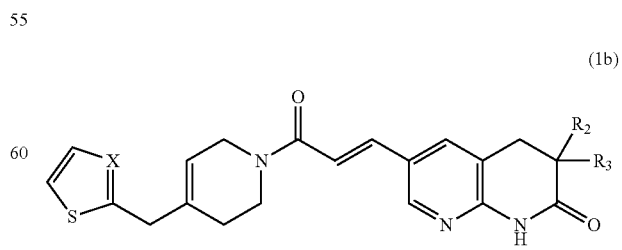

(1b)

wherein,
$R_2$ and $R_3$ are same and are as defined in claim 5.

7. The compound according to claim 1 is a compound of formula (1c)

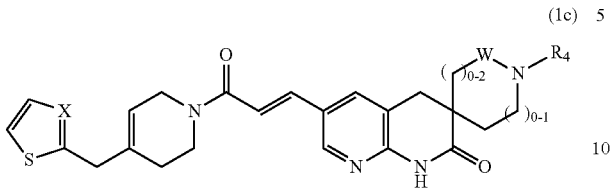

wherein, W represents CH$_2$ or C(O);
X and R$_4$ are same and are as defined in claim 1.

8. The compound according to claim 1 is a compound of formula (1d)

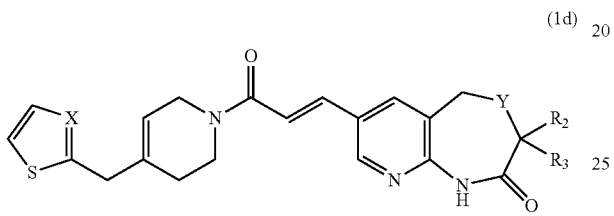

wherein, X, Y, R$_2$ and R$_3$ are same and are as defined in claim 1.

9. A compound selected from the group consisting of
(E)-tert-butyl 2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxylate (Compound-1);
(E)-6'-(3-oxo-3-(4-(thiazol-2-ylmethyl)-5,6-dihydropyridin-1(2H)-yl)prop-1-en-1-yl)-1'H-spiro[cyclopropane-1,3'-[1,8]naphthyridin]-2'(4'H)-one (Compound-2);
(E)-6'-(3-oxo-3-(4-(thiazol-2-ylmethyl)-5,6-dihydropyridin-1(2H)-yl)prop-1-en-1-yl)-1'H-spiro[cyclobutane-1,3'-[1,8]naphthyridin]-2'(4'H)-one (Compound-3);
(E)-6'-(3-oxo-3-(4-(thiazol-2-ylmethyl)-5,6-dihydropyridin-1(2H)-yl)prop-1-en-1-yl)-1'H-spiro[cyclohexane-1,3'-[1,8]naphthyridin]-2'(4'H)-one (Compound-4);
(E)-6'-(3-oxo-3-(4-(thiophen-2-ylmethyl)-5,6-dihydropyridin-1(2H)-yl)prop-1-en-1-yl)-1'H-spiro[cyclohexane-1,3'-[1,8]naphthyridin]-2'(4'H)-one (Compound-5);
(E)-6-(3-oxo-3-(4-(thiazol-2-ylmethyl)-5,6-dihydropyridin-1(2H)-yl)prop-1-en-1-yl)-2',3',5',6'-tetrahydro-1H-spiro[[1,8]naphthyridine-3,4'-pyran]-2(4H)-one (Compound-6);
(E)-6-(3-oxo-3-(4-(thiophen-2-ylmethyl)-5,6-dihydropyridin-1(2H)-yl)prop-1-en-1-yl)-2',3',5',6'-tetrahydro-1H-spiro[[1,8]naphthyridine-3,4'-pyran]-2(4H)-one (Compound-7);
(E)-6-(3-oxo-3-(4-(thiazol-2-ylmethyl)-5,6-dihydropyridin-1(2H)-yl)prop-1-en-1-yl)-1'-pivaloyl-1H-spiro[[1,8]naphthyridine-3,4'-piperidin]-2(4H)-one (Compound-8);
(E)-6-(3-oxo-3-(4-(thiophen-2-ylmethyl)-5,6-dihydropyridin-1(2H)-yl)prop-1-en-1-yl)-1'-pivaloyl-1H-spiro[[1,8]naphthyridine-3,4'-piperidin]-2(4H)-one (Compound-9);
(E)-1'-(cyclopropanecarbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound-10);

(E)-1'-(cyclopropanecarbonyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one (Compound-11);
(E)-N-(tert-butyl)-2-oxo-6-(3-oxo-3-(4-(thiazol-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide (Compound-12);
(E)-N-(tert-butyl)-2-oxo-6-(3-oxo-3-(4-(thiophen-2-ylmethyl)-5,6-dihydropyridin-1(2H)-yl)prop-1-en-1-yl)-2,4-dihydro-1H-spiro[[1,8]naphthyridine-3,4'-piperidine]-1'-carboxamide (Compound-13);
(E)-1'-(azetidine-1-carbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound-14);
(E)-1'-(azetidine-1-carbonyl)-6-(3-oxo-3-(4-(thiophen-2-ylmethyl)-5,6-dihydropyridin-1(2H)-yl)prop-1-en-1-yl)-1H-spiro[[1,8]naphthyridine-3,4'-piperidin]-2(4H)-one (Compound-15);
(E)-1'-(morpholine-4-carbonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound-16);
(E)-1'-(methylsulfonyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one (Compound-17);
(E)-tert-butyl 4-oxo-4-(2-oxo-6-(3-oxo-3-(4-(thiazol-2-ylmethyl)-5,6-dihydro pyridin-1(2H)-yl)prop-1-en-1-yl)-2,4-dihydro-1H-spiro[[1,8]naphthyridine-3,4'-piperidin]-1'-yl)butanoate (Compound-18);
(E)-6'-(3-oxo-3-(4-(thiazol-2-ylmethyl)-5,6-dihydropyridin-1(2H)-yl)prop-1-en-1-yl)-1'H-spiro[azepane-4,3'-[1,8]naphthyridine]-2',7(4'H)-dione (Compound-19);
(E)-6'-(3-oxo-3-(4-(thiophen-2-ylmethyl)-5,6-dihydropyridin-1(2H)-yl)prop-1-en-1-yl)-1'H-spiro[azepane-4,3'-[1,8]naphthyridine]-2',7(4'H)-dione (Compound-20);
(E)-3-(3-oxo-3-(4-(thiazol-2-ylmethyl)-5,6-dihydropyridin-1(2H)-yl)prop-1-en-1-yl)-6,7-dihydro-5H-pyrido[2,3-b]azepin-8(9H)-one (Compound-21);
(E)-3-(3-oxo-3-(4-(thiophen-2-ylmethyl)-5,6-dihydropyridin-1(2H)-yl)prop-1-en-1-yl)-6,7-dihydro-5H-pyrido[2,3-b]azepin-8(9H)-one (Compound-22);
(E)-7'(3-oxo-3-(4-(thiazol-2-ylmethyl)-5,6-dihydropyridin-1(2H)-yl)prop-1-en-1-yl)-4',5'-dihydrospiro[cyclopropane-1,3'-pyrido[2,3-e][1,4]diazepin]-2'(1'H)-one (Compound-23);
(E)-7'-(3-oxo-3-(4-(thiophen-2-ylmethyl)-5,6-dihydropyridin-1(2H)-yl)prop-1-en-1-yl)-4',5'-dihydrospiro[cyclopropane-1,3'-pyrido[2,3-e][1,4]diazepin]-2'(1'H)-one (Compound-24);
(E)-3,3-dimethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one (Compound-25);
(E)-3,3-dimethyl-6-(3-oxo-3-(4-(thiophen-2-ylmethyl)-5,6-dihydropyridin-1(2H)-yl)prop-1-en-1-yl)-3,4-dihydro-1,8-naphthyridin-2(1H)-one (Compound-26);
(E)-3,3-diethyl-6-(3-oxo-3-(4-(thiazol-2-ylmethyl)-5,6-dihydropyridin-1(2H)-yl)prop-1-en-1-yl)-3,4-dihydro-1,8-naphthyridin-2(1H)-one (Compound-27);
(E)-6'-(3-oxo-3-(4-(thiophen-2-ylmethyl)-5,6-dihydropyridin-1(2H)-yl)prop-1-en-1-yl)-1'H-spiro[cyclopropane-1,3'-[1,8]naphthyridin]-2'(4'H)-one (Compound-28);

(E)-6'-(3-oxo-3-(4-(thiophen-2-ylmethyl)-5,6-dihydropy-ridin-1(2H)-yl)prop-1-en-1-yl)-1'H-spiro[cyclobutane-1,3'-[1,8]naphthyridin]-2'(4'H)-one (Compound-29);

(E)-1-methyl-6'-(3-oxo-3-(4-(thiazol-2-ylmethyl)-5,6-di-hydropyridin-1(2H)-yl)prop-1-en-1-yl)-1'H-spiro [azepane-4,3'-[1,8]naphthyridine]-2',7(4'H)-dione (Compound-30);(E)-1'-(cyclopentanecarbonyl)-6-(3-oxo-3-(4-(thiazol-2-ylmethyl)-5,6-dihydropyridin-1 (2H)-yl)prop-1-en-1-yl)-1H-spiro[[1,8]naphthyridine-3,4'-piperidin]-2(4H)-one (Compound-31);

(S,E)-3-(3-oxo-3-(4-(thiazol-2-ylmethyl)-5,6-dihydropy-ridin-1(2H)-yl)prop-1-en-1-yl)-7,8,9,9a-tetrahydro-5H-pyrido[2,3-e]pyrrolo[1,2-a][1,4]diazepin-10(11H)-one (Compound-32);

(S,E)-3-(3-oxo-3-(4-(thiophen-2-ylmethyl)-5,6-dihydro-pyridin-1(2H)-yl)prop-1-en-1-yl)-7,8,9,9a-tetrahydro-5H-pyrido[2,3-e]pyrrolo[1,2-a][1,4]diazepin-10(11H)-one (Compound-33);

(E)-6-(3-oxo-3-(4-(thiazol-2-ylmethyl)-5,6-dihydropyri-din-1(2H)-yl)prop-1-en-1-yl)-1H-spiro[[1,8]naphthyri-dine-3,4'-piperidin]-2(4H)-one 2,2,2-trifluoroacetate (Compound-34);

(E)-1'-methyl-6-(3-oxo-3-(4-(thiazol-2-ylmethyl)-5,6-di-hydropyridin-1(2H)-yl)prop-1-en-1-yl)-1H-spiro[[1,8] naphthyridine-3,4'-piperidin]-2(4H)-one (Compound-35);

(E)-1'-cyclopropyl-6-(3-oxo-3-(4-(thiazol-2-ylmethyl)-5, 6-dihydropyridin-1(2H)-yl)prop-1-en-1-yl)-1H-spiro [[1,8]naphthyridine-3,4'-piperidin]-2(4H)-one (Compound-36);

(E)-1'-(2-hydroxyacetyl)-6-(3-oxo-3-(4-(thiazol-2-ylm-ethyl)-5,6-dihydropyridin-1(2H)-yl)prop-1-en-1-yl)-1H-spiro[[1,8]naphthyridine-3,4'-piperidin]-2(4H)-one (Compound-37);

(E)-1'-(furan-2-carbonyl)-6-(3-oxo-3-(4-(thiazol-2-ylm-ethyl)-5,6-dihydropyridin-1(2H)-yl)prop-1-en-1-yl)-1H-spiro[[1,8]naphthyridine-3,4'-piperidin]-2(4H)-one (Compound-38);

(E)-2-oxo-6-(3-oxo-3-(4-(thiazol-2-ylmethyl)-5,6-dihy-dropyridin-1(2H)-yl)prop-1-en-1-yl)-2,4-dihydro-1H-spiro[[1,8]naphthyridine-3,4'-piperidine]-1'-carboxam-ide (Compound-39);

(E')-4-oxo-4-(2-oxo-6-(3-oxo-3-(4-(thiazol-2-ylmethyl)-5,6-dihydropyridin-1(2H)-yl)prop-1-en-1-yl)-2,4-dihy-dro-1H-spiro[[1,8]naphthyridine-3,4'-piperidin]-1'-yl) butanoic acid (Compound-40);

(E)-1'-(2-aminoacetyl)-6-(3-oxo-3-(4-(thiazol-2-ylm-ethyl)-5,6-dihydropyridin-1(2H)-yl)prop-1-en-1-yl)-1H-spiro[[1,8]naphthyridine-3,4'-piperidin]-2(4H)-one hydrochloride (Compound-41);

(E)-1'-(2-(tert-butylamino)acetyl)-6-(3-oxo-3-(4-(thiazol-2-ylmethyl)-5,6-dihydropyridin-1(2H)-yl)prop-1-en-1-yl)-1H-spiro[[1,8]naphthyridine-3,4'-piperidin]-2(4H)-one 2,2,2-trifluoroacetate (Compound-42); and (E)-1-(2-hydroxyacetyl)-6'-(3-oxo-3-(4-(thiazol-2-ylm-ethyl)-5,6-dihydropyridin-1(2H)-yl)prop-1-en-1-yl)-l'H-spiro[azetidine-3,3'-[1,8]naphthyridin]-2'(4'H)-one (Compound-43), or a pharmaceutically acceptable salt or a pharmaceutically acceptable stereoisomer thereof.

10. A pharmaceutical composition comprising a therapeutically effective amount of a compound according to claim 1, their pharmaceutically acceptable salts and pharmaceutically acceptable stereoisomers thereof, in admixture with at least one pharmaceutically acceptable carriers, diluents or excipients, including mixtures thereof in all ratios, for use as a medicament.

11. A pharmaceutical combination comprising a compound according to claim 1, their pharmaceutically acceptable salts and pharmaceutically acceptable stereoisomers thereof, and at least one or more therapeutically further active ingredient.

12. A compound according to claim 1, their pharmaceutically acceptable salts and pharmaceutically acceptable stereoisomers thereof, for use in treating bacterial infection.

13. A compound according to claim 1, their pharmaceutically acceptable salts and pharmaceutically acceptable stereoisomers thereof, for use in treatment of bacterial infection for which FabI inhibitor is indicated.

14. A method of treating bacterial infection for which FabI is indicated in a subject in need thereof which comprises administering a therapeutically effective amount of a compound according to claim 1, their pharmaceutically acceptable salts and pharmaceutically acceptable stereoisomers thereof.

15. The method of treatment according to claim 14, wherein the subject is an animal including human.

16. A process for the preparation of compound of formula 1 as claimed in claim 1 or a pharmaceutically acceptable salt or a pharmaceutically acceptable stereoisomer thereof, which comprises:

reacting intermediate compound of formula 1.10

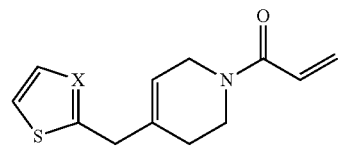

Formula 1.10 wherein, X is CH or N; with intermediate compound of formula 1.11

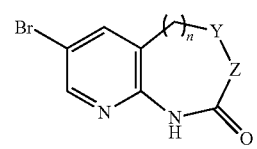

Formula 1.11 wherein, Y, Z and n are same as defined in claim 1;
by heck reaction in a solvent in the presence of a palladium catalyst, ligand and a base to give compound of formula 1.

17. The process according to claim 16, wherein the solvent used in the reaction is selected from polar solvents such as DMF, propionitrile, ACN, THF or DMSO; palladium catalyst is selected from Pd(dppf)$_2$Cl$_2$, Pd(PPh$_3$)$_4$, Pd$_2$(dba)$_3$ or Pd(OAc)$_2$ and the ligand is selected from P(o-tolyl)$_3$, P(m-tolyl)$_3$ or P(p-tolyl)$_3$.

18. A process for the preparation of compound of formula 1 as claimed in claim 1 or a pharmaceutically acceptable salt or a pharmaceutically acceptable stereoisomer thereof, which comprises:

reacting intermediate compound of formula 1.9

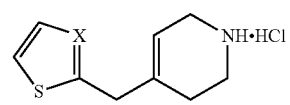

Formula 1.9 wherein, X is CH or N; with intermediate compound of formula 1.12

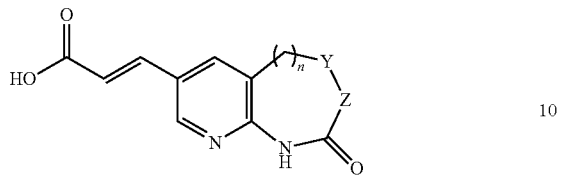

Formula 1.12 wherein, Y, Z and n are same as defined in claim 1;
by acid amine coupling in a solvent in the presence of a coupling reagent and a base to give compound of formula 1.

19. The process according to claim 18, wherein the solvent is selected from DMF, THF, DMSO or DCM; the coupling reagents is selected from benzotriazole-containing coupling reagent such as such as 1-hydroxybenzotriazole (HOBt), benzotriazole-1-yloxytris (dimethylamino)phosphonium-hexafluorophosphate or 2-(1H-benzotriazol-1-yl)-1,1,3,3-tetra methyluroniumhexafluorophosphate; azabenzotriazole-containing reagent such as O-(7-azabenzotriazole-1-yl)-N or dicarboimides containing reagent such as 1-Ethyl-3-(3-dimethylaminopropyl) carbodiimide hydrochloride, dicyclohexylcarbodiimide or HATU and the base used in the reaction is selected from TEA or DIPEA.

\* \* \* \* \*

UNITED STATES PATENT AND TRADEMARK OFFICE
CERTIFICATE OF CORRECTION

PATENT NO.         : 9,062,075 B2
APPLICATION NO.    : 14/294576
DATED              : June 23, 2015
INVENTOR(S)        : Mohamed Takhi, Subramanya Hosahalli and Sunil Kumar Panigrahi It is certified that error appears in the above-identified patent and that said Letters Patent is hereby corrected as shown below:

In the specification

Column 4, illustration (1b), delete "X" and insert --N-- therefor.

Column 22, Lines 10-20, delete "X" in both illustrations and insert --N-- therefor.

Column 37, Line 44, delete "lypethoxy" and insert --yl)ethoxy-- therefor.

Column 37, Line 57, delete "trimethylsilylethoxy" and insert --trimethylsilyl)ethoxy-- therefor.

Column 38, Line 50, delete "1-4(2-amino-5-bro-" and insert --1-(((2-amino-5-bro- -- therefor.

Column 39, Line 12, delete "1-4(2-amino-5-bromopyridin-" and insert --1-(((2-amino-5-bromopyridin- -- therefor.

Column 45, Compound 5, delete the leftmost "N" on the illustration.

Column 55, Line 10, delete "(E)-β -methyl-6-(3-oxo-3-(4-(thia-" and insert --(E)-6-(3-oxo-3-(4-(thia- -- therefor.

Column 59, Line 5, delete "en-1-1-2,4" and insert --en-1-yl)-2,4-- therefor.

Columns 59-60, illustration Compound-14.5, delete "Compound-14.5" and insert --Intermediate-14.5-- therefor.

Column 63-64, illustration Compound-13, delete "Compound-13" and insert --Intermediate-13-- therefor.

Column 65, Line 2, delete "yl)-T-oxo-2',4'" and insert --yl)-2'-oxo-2',4'-- therefor.

Signed and Sealed this
Fifteenth Day of December, 2015

Michelle K. Lee
*Director of the United States Patent and Trademark Office*

CERTIFICATE OF CORRECTION (continued)
U.S. Pat. No. 9,062,075 B2

Column 65, Line 14, delete "T-oxo-6'" and insert --2'-oxo-6'-- therefor.

Column 66, Line 10, delete "100" and insert --10μl-- therefor.

Column 66, Line 14, delete "1004" and insert --100μ L-- therefor.

In the claims

Column 68, illustration (1b), delete "X" and insert --N-- therefor.